US009868937B2

(12) United States Patent
Regnier et al.

(10) Patent No.: US 9,868,937 B2
(45) Date of Patent: Jan. 16, 2018

(54) CELL AND GENE BASED METHODS TO IMPROVE CARDIAC FUNCTION

(75) Inventors: Michael Regnier, Bellevue, WA (US); Michael Laflamme, Seattle, WA (US); Charles Murry, Seattle, WA (US); F. Steven Korte, Port Orchard, WA (US); Scott Lundy, Shoreline, WA (US); Stephen Denison Hauschka, Seattle, WA (US); Jeffrey S. Chamberlain, Seattle, WA (US); Guy Odom, Seattle, WA (US)

(73) Assignee: University of Washington, Seattle, WA (US)

( * ) Notice: Subject to any disclaimer, the term of this patent is extended or adjusted under 35 U.S.C. 154(b) by 909 days.

(21) Appl. No.: 14/122,226

(22) PCT Filed: May 29, 2012

(86) PCT No.: PCT/US2012/039897
§ 371 (c)(1),
(2), (4) Date: Apr. 21, 2014

(87) PCT Pub. No.: WO2012/162705
PCT Pub. Date: Nov. 29, 2012

(65) Prior Publication Data
US 2016/0186139 A1 Jun. 30, 2016

Related U.S. Application Data

(60) Provisional application No. 61/490,450, filed on May 26, 2011.

(51) Int. Cl.
| C12N 5/077 | (2010.01) |
| C12N 9/02 | (2006.01) |
| A01K 67/027 | (2006.01) |
| A61K 48/00 | (2006.01) |
| C07K 14/47 | (2006.01) |
| C12N 15/85 | (2006.01) |
| A61K 9/00 | (2006.01) |
| A61K 35/34 | (2015.01) |
| C12N 7/00 | (2006.01) |
| C12N 15/86 | (2006.01) |

(52) U.S. Cl.
CPC ........ *C12N 5/0657* (2013.01); *A01K 67/0275* (2013.01); *A61K 9/0019* (2013.01); *A61K 35/34* (2013.01); *A61K 48/005* (2013.01); *C07K 14/4716* (2013.01); *C12N 7/00* (2013.01); *C12N 9/0093* (2013.01); *C12N 15/8509* (2013.01); *C12N 15/86* (2013.01); *C12Y 117/04002* (2013.01); *A01K 2217/052* (2013.01); *A01K 2227/105* (2013.01); *A01K 2267/0375* (2013.01); *C12N 2750/14132* (2013.01); *C12N 2750/14143* (2013.01); *C12N 2799/022* (2013.01); *C12N 2799/025* (2013.01); *C12Y 117/04001* (2013.01)

(58) Field of Classification Search
None
See application file for complete search history.

(56) References Cited

U.S. PATENT DOCUMENTS

| 6,451,594 B1 | 9/2002 | Chien et al. |
| 6,671,558 B1 | 12/2003 | Soykan et al. |
| 2003/0204206 A1 | 10/2003 | Padua et al. |
| 2007/0117766 A1 | 5/2007 | Phillips et al. |
| 2008/0152635 A1 | 6/2008 | Lee et al. |

FOREIGN PATENT DOCUMENTS

| AU | 2012258525 | 6/2017 |
| CN | 103946230 | 2/2017 |
| DE | 10 2011 018586 | 10/2012 |
| EP | 1950301 | 7/2008 |
| JP | 6162104 | 6/2017 |
| RU | 2378375 | 1/2010 |
| RU | 2608957 | 1/2017 |
| WO | 1999-062940 | 12/1999 |
| WO | WO 2000-38518 | 7/2000 |
| WO | 2002-049714 | 6/2002 |
| WO | WO 2004-024867 | 3/2004 |
| WO | 2005-094485 | 10/2005 |

OTHER PUBLICATIONS

Zhou et al., Cancer Reasearch, 1995, vol. 55, pp. 1328-1333.*
Wang et al., Biophysical Journal, 2010, vol. 98, pp. 149a-150a.*
Beltrami et al., The New England Journal of Medicine, 2001, vol. 344, pp. 1750-1757.*
Nordlund et al., Annu. Rev. Biochem., 2006, vol. 75, pp. 681-706.*
Pacak et al., Genetic Vaccines and Therapy, 2008, vol. 6:13, pp. 1-5.*
International Preliminary Report on Patentability dated Nov. 26, 2013 as received in International Application No. PCT/US2012/039897.

(Continued)

Primary Examiner — Mindy G Brown
(74) Attorney, Agent, or Firm — Stoel Rives LLP; Zhi-Xiang (Alex) Oh

(57) ABSTRACT

Compositions and methods for improving cardiac function, myocardial contractility and relaxation in a mammal are provided. Cardiomyocytes transfected with one or more expression vectors comprising a ribonucleotide reductase subunit R1-encoding nucleic acid sequence and a ribonucleotide reductase subunit R2-encoding nucleic acid sequence operably linked to a promoter are grafted to a mammalian myocardium. Also provided are compositions and methods for delivering dATP to a myocardium through grafting of donor cells overexpressing R1 and R2. dATP is thereby produced in situ and delivered through gap junctions established between donor cells and host cardiomyocytes. Alternatively, viral vector(s) having the R1 and R2-encoding construct(s) are administered to the mammal directly. Improvement of cardiac function can also be effected by administration of vectors comprising a nucleic acid sequence encoding a L48Q, 61 Q, or L57Q cTnC variant.

18 Claims, 40 Drawing Sheets

(56) References Cited

OTHER PUBLICATIONS

International Search Report dated Dec. 18, 2012 as received in International Application No. PCT/US2012/039897.
Written Opinion dated Dec. 18, 2012 as received in International Application No. PCT/US2012/039897.
Zincarelli et al., "Comparative Cardiac Gene Delivery of Adeno-Associated Virus Serotypes 1-9 reveals that AAV6 Mediates the Most Efficient Transduction in Mouse Heart," CTS Journal.com, vol. 3, Iss. 2, DOI: 10.111/j.1752-B062.2010.00190.
Jielin, Pu, A Study on L Type Calcium Channel, Ca 2+ Handling and Na +/Ca 2+ Exchange Function of Infarcted Myocardial Cells., Chinese Circulation Journal, vol. 14, pp. 24-26.
Dan Wang et al: "Mutations that Alter cTnC Ca2+ Binding Affect Interactions with cTnI and Cardiomyocyte Contraction", Biophysical Journal, vol. 100, No. 3, Feb. 2, 2011 (Feb. 2, 2011), p. 360a, XP55178913, * abstract *.
Eric R. Feest et al: "Effect of Varying Mutant Troponin C Content on Contractile Properties of Striated Muscle", Biophysical Journal, vol. 96, No. 3, Feb. 1, 2009 (Feb. 1, 2009), p. 228a, XP55179133, DOI: doi:10.1016jj.bpj.2008.12.1120 * abstract *.
Kate O. Buckley: "Engineering Troponin C to Improve Cardiomyocyte Contraction and Relaxation Following Myocardial Infarction", Biophysical Journal, vol. 98, No. 3, Jan. 1, 2010 (Jan. 1, 2010), p. 356a, XP55180079, DOI: doi:10.1016jj.bpj.2009.12.1923 * abstract *.
Pillip Poonka: "Myofilament Targeted Gene Therapy to Treat Myocardial Infarction", May 21, 2010 (May 21, 2010), XP55180114, Retrieved from the Internet: RL:http://www.washington.edu/undergradresearch/files/2014/06/Poster-Program.pdf [retrieved on Mar. 30, 2015] * abstract *.
Pacak Christina A. et al: "Tissue specific promoters improve specificity of AAV9 mediated transgene expression following intravascular gene delivery in neonatal mice" Genetic Vaccines and Therapy, Biomed Central, London, GB, vol. 6, No. 1, Sep. 23, 2008 (Sep. 23, 2008), p. 13, XP021044007, ISSN: 1479-0556, DOI: 10.1186/1479-0556-6-13 * figure 1 *.
Kareen L. Kreutziger et al: "Calcium binding kinetics of troponin C strongly modulate cooperative activation and tension kinetics in cardiac muscle", Journal of Molecular and Cellular Cardiology, Academic Press, GB, vol. 50, No. 1, Oct. 18, 2010 (Oct. 18, 2010), pp. 165-174, XP028129367, ISSN: 0022-2828, DOI: 10.1016/J.YJMCC.2010.10.025 [retrieved on Oct. 28, 2010].
Korte F. Steven et al: "Broad Transgenic, and Cardiac-Specific Viral Mediated, Over-Expression of Ribonucleotide Reductase Increases In Vivo Cardiac Contractility", Biophysical Journal, vol. 102, No. 3, Feb. 29, 2812 (2812-82-29), XP828892859, ISSN: 8886-3495, DOI: 18.1816/J.BPJ.2811.11.3351 * abstract *.
"Abstracts presented at the 39th European Muscle Conference of the European Society for Muscle Research", Journal of Muscle Research and Cell Motility, vol. 32, No. 2, Sep. 1, 2811 (2811-89-81), pp. 111-167, XP55188856, ISSN: 8142-4319, DOI: 18.1887fsl8974-811-9257-6 * First abstract on p. 128 *.
Scott D. Lundy et al: "Cell-based delivery of dATP via gap junctions enhances cardiac contractility", Journal of Molecular and Cellular Cardiology, vol. 72, Jul. 1, 2014 (Jul. 1, 2014), pp. 350-359, XP55178798, ISSN: 0022-2828, DOI: 10.1016fj.yjmcc.2014.04.010.
Erik R. Feest et al: "Thin filament incorporation of an engineered cardiac troponin C variant (L48Q) enhances contractility in intact cardiomyocytes from healthy and infarcted hearts", Journal of Molecular and Cellular Cardiology, vol. 72, Jul. 1, 2014 (Jul. 1, 2014), pp. 219-227, XP55178772, ISSN: 0022-2828, DOI:10.1016/j.yjmcc.2014.03.015.
Shettigar Vikram et al: "Incorporation of Troponin C with Modified Ca2+Binding into the Heart through the use of Adena-Associated Virus Leads to Altered Heart Function", Biophysical Journal, vol. 106, No. 2, Feb. 17, 2014 (Feb. 17, 2014), XP028823632, ISSN: 0006-3495, DOI:10.1016/J.BPJ.2013.11.1967.
Korte et al., Targeting Myofilaments to Improve Cardiomyocyte Contractile Properties in Heart Disease., Molecular Therapy, May 2009, vol. 17, Supplement 1, p. S349, 914.
Ma et al., Cell-specific expression of SERCA, the exogenous $Ca^{2+}$ transport ATPase, in cardiac myocytes., American Journal of Physiology, 2004, vol. 286, No. 3, p. C556-C564.
Regnier et al.: '2-Deoxy-ATP Enhances Contractility of Rat Cardiac Muscle' Circ Res. vol. 86, No. 12, 2000, pp. 1211-1217.
Zhou et al.: 'Overexpression of Ribonucleotide Reductase in Transfected Human KB Cells Increases Their Resistance to Hydroxyurea: M2 but not MI Is Sufficient to Increase Resistance to Hydroxyurea in Transfected Cells' Cancer Research vol. 55, 1995, pp. 1328-1333.
H. Su et al: "Adena-associated viral vector delivers cardiac-specific and hypoxia-inducible VEGF expression in ischemic mouse hearts", Proceedings of the National Academy of Sciences, vol. 101, No. 46, Nov. 16, 2004 (Nov. 16, 2004), pp. 16280-16285.
Brenda Schoffstall et al: "Increased intracellular [dATP] enhances cardiac contraction in embryonic chick cardiomyocytes", Journal of Cellular Biochemistry, vol. 104, No. 6, May 1, 2008 (May 1, 2008), pp. 2217-2227.
K-M R Prasad et al: "Robust cardiomyocyte-specific gene expression following systemic injection of AAV: in vivo gene delivery follows a Poisson distribution", Gene Therapy, vol. 18, No. 1, Aug. 12, 2010 (Aug. 12, 2010), pp. 43-52.
Pacak Christina A et al: "Tissue specific promoters improve specificity of AAV9 mediated transgene expression following intravascular gene delivery in neonatal mice" Genetic Vaccines and Therapy, Biomed Central, London, GB, vol. 6, No. 1, Sep. 23, 2008 (Sep. 23, 2008), p. 13.
Korte F S et al: "Upregulation of cardiomyocyte ribonucleotide reductase increases intracellular 2 deoxy-ATP, contractility, and relaxation", Journal of Molecular and Cellular Cardiology, Academic Press, GB, vol. 51, No. 6, Aug. 25, 2011.
Gay Elizabeth et al: "AAV6-Mediated Overexpression of Ribonucleotide Reductase (R1R2) Enhances 2-Deoxy-ATP Concentration in Vivo and Improves Cardiac Function", Biophysical Journal, vol. 106, No. 2, Oct. 31, 2014.
S. G. Nowakowski et al: "Transgenic overexpression of ribonucleotide reductase improves cardiac performance", Proceedings of the National Academy of Sciences, vol. 110, No. 15, Apr. 9, 2013.

* cited by examiner

Brightfield 400x    GFP 400X

```
hum-cTnT455 sequence (SEQ ID NO:1):
ctgctcccagctggccctcccaggcctgggttgctggcctctgcttt
atcaggattctcaagagggacagctggtttatgttgcatgactgttc
cctgcatatctgctctggttttaaatagcttatctgctagcctgctc
ccagctggccctcccaggcctgggttgctggcctctgctttatcagg
attctcaagagggacagctggtttatgttgcatgactgttccctgca
tatctgctctggttttaaatagcttatctgagcagctggaggaccac
atgggcttatatggggcacctgccaaaatagcagccaacaccccccc
ctgtcgcacattcctccctggctcaccaggccccagcccacatgcct
gcttaaagccctctccatcctctgcctcacccagtccccgctgagac
tgagcagacgcctccaggatctgtcggcagct
```

FIG. 40

SEQUENCE LISTING

```
<160> NUMBER OF SEQ ID NOS: 1

<210> SEQ ID NO 1
<211> LENGTH: 455
<212> TYPE: DNA
<213> ORGANISM: Artificial Sequence
<220> FEATURE:
<223> OTHER INFORMATION: cTnT455 cardiac-specific promoter

<400> SEQUENCE: 1
ctgctcccag ctggccctcc caggcctggg ttgctggcct ctgctttatc aggattctca      60
agagggacag ctggtttatg ttgcatgact gttccctgca tatctgctct ggtttaaat     120 agcttatctg ctagcctgct cccagctggc cctccaggc ctgggttgct ggcctctgct     180
ttatcaggat tctcaagagg gacagctggt ttatgttgca tgactgttcc ctgcatatct     240
gctctggttt taaatagctt atctgagcag ctggaggacc acatgggctt atatggggca     300
cctgccaaaa tagcagccaa caccccccc tgtcgcacat tcctccctgg ctcaccaggc     360
cccagcccac atgcctgctt aaagccctct ccatcctctg cctcacccag tccccgctga     420
gactgagcag acgcctccag gatctgtcgg cagct                                455
```

CELL AND GENE BASED METHODS TO IMPROVE CARDIAC FUNCTION

CROSS-REFERENCE TO RELATED APPLICATIONS

This application claims benefit under 35 U.S.C. §119(e) to U.S. Provisional Application No. 61/490,450 filed on May 26, 2011, entirely incorporated herein by reference.

STATEMENT AS TO RIGHTS TO INVENTIONS MADE UNDER FEDERALLY SPONSORED RESEARCH OR DEVELOPMENT

This invention was made with government support under Grant Nos. HL61683, R21 HL091368, HL07828, HL65497, R01 HL64387, R01 HL084642, and P01 HL004374 awarded by the National Institutes of Health. The Government has certain rights in this invention.

BACKGROUND OF THE INVENTION

Heart disease is the leading cause of mortality and morbidity in the United States and has been rising dramatically around the world[8]. Cardiac diseases of the sarcomere, such as HCM and DCM, involve amino acid mutations in one of several myofilament proteins commonly leading to heart failure, and in some cases sudden cardiac death[1,2,9]. As the number of identified mutants with functional characterization has grown, some patterns have emerged that demonstrate potential similarities in altered contractile properties. For example, most HCM mutations result in increased $Ca^{2+}$ sensitivity of contractile force in demembranated cardiac muscle[1,10-17], while most DCM variants result in decreased $Ca^{2+}$ sensitivity of force[1,18-23]. However, the extent of which these alterations in myofilament $Ca^{2+}$ sensitivity are involved in progression of the diseases is not known. Potential and important interactions between altered myofilament $Ca^{2+}$ binding and SR function have not been systematically investigated, nor have interactions with other intracellular $Ca^{2+}$ buffers (e.g., mitochondria) or gene regulation.

Many cardiopathologies, as well as ischemia-reperfusion injury and myocardial infarct result in reduced systolic function due to damage and/or death to a portion of the myocardium that significantly compromises cardiac function. Infarcted hearts often do not meet the cardiovascular demands of the body and attempt to compensate by increasing β-adrenergic activation. Chronic β-adrenergic stimulation, however, exhausts contractile reserves, can elevate diastolic $Ca^{2+}$ levels, and eventually results in down-regulation of adrenergic responsiveness leading to end-stage heart failure[8-10]*. Importantly, a number of studies in both animal models and patients have noted alterations in both myofilament[11-16] and sarcoplasmic reticulum (SR) and sarcolemmal[17-18]* protein content and phosphorylation following infarction, which would alter myofilament $Ca^{2+}$ sensitivity of force and $Ca^{2+}$ transient release/reuptake. Similar changes have been observed in hearts expressing mutations associated with DCM and HCM[35]. Although global alterations in hormone levels (such as 3-adrenergic agonists) have often been implicated in these adaptations, the mechanism(s) may be due (at least in part) to intracellular interplay between SR and myofilament proteins.

Cardiac function is compromised in a number of cardiovascular diseases including myocardial infarction, ischemia/reperfusion injury, diabetes, high blood pressure and hypertrophic and dilated cardiomyopathy. These pathophysiological conditions often alter the $Ca^{2+}$ cycle[1], β-adrenergic responsiveness[2], and/or the contractile apparatus of cardiomyocytes. To date, therapeutic efforts have focused primarily on increasing $[Ca^{2+}]_i$, which tend to exert a pro-arrhythmogenic effect, impair ventricular filling by slowing diastolic relaxations, and cause SR $Ca^{2+}$ overload initiating triggered activity[19]*. Other approaches involving adrenergic agents can have undesirable long-term side-effects, e.g. significant drug actions in non-target areas, pro-arrythmogenic triggered activity, and potential for accelerated progression into heart failure[2]. Thus, new approaches to combat cardiac dysfunction are desirable.

An alternative approach involves the use of $Ca^{2+}$ sensitizing compounds that enhance $Ca^{2+}$ binding to cardiac troponin C (cTnC) and increase contractile strength[4]. Considerable effort has been made to develop pharmaceutical agents such as calmidazolium, bepridil and levosimenden that increase $Ca^{2+}$ binding to the N-terminus (site II, the 'trigger site') of cTnC and enhance contractile activation. Some drawbacks associated which such compounds include their non-specificity to cTnC and deleterious effects on proteins involved in $Ca^{2+}$ handling[21,22] and other aspects of the excitation-contraction coupling pathway[5].

In view of the drawbacks associated with various conventional pharmacological and surgical approaches, which are generally aimed at slowing progression of heart failure as opposed to recovery of function, novel methods of improving cardiac function are needed. The present invention provides more targeted approaches for enhancing cardiac contraction without affecting EC coupling[6], i.e. generation of recombinant novel cTnC variants with altered $Ca^{2+}$ binding properties or in situ production or administration of dATP by ribonucleotide reductase for use as a replacement substrate in cardiac contraction.

SUMMARY OF THE INVENTION

One aspect of the invention is based on the surprising discovery that even modest increases in overall cellular levels of dATP (as low as 1.0%-2% of total adenine nucleotide pool) yield substantial improvements in cardiac contractility. Increase in dATP levels is achieved by methods of the present invention using vectors expressing promoter-driven Rrm1 (ribonucleotide reductase subunit 1) or Rrm2 (ribonucleotide reductase subunit 2), administered to the individual or through grafting of donor cells transduced with the vectors to the host myocardium. Also unexpected was the ability of the presently disclosed methods to improve contractility, and seemingly increase calcium sensitivity, without corresponding adverse effects on cardiac relaxation or $Ca^{2+}$ transients. On the contrary, cardiac relaxation was appreciably faster as a result of increased dATP levels. Improvement in cardiac function was evidenced by increase in left ventricular fractional shortening and increased extent and rate of shortening and relaxation of isolated cardiomyocytes, as observed through echoradiography and IonOptix system video microscopy. Benefits of the present invention were confirmed in mouse and rat studies having normal or infarcted hearts. Increased dATP levels had the effect of increasing pre-load responsiveness in Langendorf-working heart studies and rescuing heart failure. The autoregulatory mechanism of ribonucleotide reductase, i.e. allosteric activation by ATP and inhibition by dATP, also provides another remarkable advantage by preventing dATP levels from reaching toxic levels with the overexpression of RR. As such, the present invention provides a novel therapeutic approach without various drawbacks, e.g. arrhythmogenesis, impairment of ventricular filling by slowed diastolic relaxation, side-effects in non-target areas, and potentially accelerated progression into heart failure, associated with conventional therapeutic approaches manipulating Ca$^{2+}$ levels or adrenergic signaling.

Another aspect of the invention is based on the discovery of the effects which altered myofilament Ca2+ binding (and associated changes in contractile properties) has on 1) cardiac sarcoplasmic reticulum (SR) function and 2) cardiac performance in normal and diseased cardiac muscle. For these studies, we have produced several cTnC variants with increased or decreased Ca2+ binding affinity. When exchanged into chemically demembranated cardiac muscle, or cardiac myofibrils, these cTnC variants increased and decreased the Ca2+ sensitivity of force, respectively[6]. Adenoviral vectors containing cDNA encoding these cTnC variants (with a C-terminal His-tag)+GFP and transfected cultured adult rat cardiomyocytes were produced for studies of stimulated contraction, with the L48Q cTnC variant demonstrating increased Ca2+ binding affinity (vs. WT cTnC), greatly increased magnitude and rate of shortening[7], and little or no effect on Ca2+ transients (measured by ratiometric fura-2 fluorescence). Significantly, L48Q cTnC expression rescued the loss of both contractility and Ca2+ transient amplitude characteristic of cells from infarcted hearts. On the other hand, I61Q cTnC variant demonstrated decreased Ca2+ binding affinity, decreased shortening magnitude (>60%) and rate and also, surprisingly, reduced amplitude (>20%) and rising rate of the Ca2+ transient. These data indicate an interplay between myofilament Ca2+ binding and SR Ca2+ release. Remarkably, it is shown herein that systemic injection of AAV6-L48Q cTnC increased cardiac ejection fraction of normal mice by 20% at 2 weeks and 30-40% at 3 weeks (FIG. 12).

In one aspect of the invention, methods and compositions for improving cardiac function, myocardial contractility and myocardial relaxation, in a mammal, e.g. human, are provided. Cardiomyocytes containing a first expression vector comprising a first nucleic acid sequence encoding ribonucleotide reductase subunit R1 and a second expression vector comprising a second nucleic acid sequence encoding ribonucleotide reductase subunit R2 are grafted to the myocardium of the mammal in need of treatment, e.g. a mammal having an infarcted myocardium. The first nucleic acid sequence and second nucleic acid sequence are operably linked to a promoter which induces overexpression of R1 and R2. In some embodiments, the R1 and R2-encoding constructs are part of the same expression vector or on different expression vectors. The promoter may, in some instances, be selected from a cardiac-specific promoter, e.g. cTnT455, for selective expression in the heart. Those of skill in the art would appreciate that other promoters suitable for inducing expression in eukaryotic, e.g. mammalian, cells may be employed. In specific embodiments, overexpression is driven by a CK7 promoter or a CMV promoter.

Cellular production of dATP normally proceeds in mammalian cells by action of the ribonucleotide reductase (R1R2) enzyme, which removes a hydroxyl moiety from the 2-position on the ribose ring of ADP to produce dADP. dADP is then rapidly converted to dATP. Advantages of the present invention can be achieved by overexpression of R1 and R2, which form the ribonucleotide reductase complex, resulting ultimately in the production of dATP in situ.

In some embodiments, the expression vector is a viral vector, such as an adeno-associated viral vector, e.g. an AAV6, AAV2, rAAV2/1, rAAV2/2, rAAV2/3, rAAV2/4, rAAV2/5, rAAV2/6, rAAV2/7 rAAV2/8, rAAV2/9, rAAV2/10, rAAVM41, dsAAV, etc. In various embodiments, the expression vector further comprises a transduction reporter. The cardiomyocytes may be derived from embryonic stem cells (ESC), induced pluripotent stem cells (iPSC), or mesenchymal stem cells, of mammalian origin. In some embodiments, the method employs cardiomyocytes derived from human stem cells. iPSCs may be derived from a cell, e.g. fibroblast, harvested from the mammal to be treated.

In some embodiments, the method involves prior to grafting of the cardiomyocytes, transducing said cardiomyocytes with the R1 and R2-encoding first and second expression vectors ex vivo. The grafting of cardiomyocytes may be effected via delivery through a catheter. In embodiments involving treatment of an infarcted myocardium, the cardiomyocytes may be delivered to a region of the myocardium containing live cells, e.g. a non-infarct zone of the myocardium.

Alternatively, improvement in cardiac function and myocardial contractility and relaxation in a mammal, e.g. human, may be effected by administration of a first viral vector comprising a first nucleic acid sequence encoding ribonucleotide reductase subunit R1 and a second viral vector comprising a second nucleic acid sequence encoding ribonucleotide reductase subunit R2, said first nucleic acid sequence and second nucleic acid sequence being operably linked to a cardiac-specific promoter, e.g. cTnT455. The R1 and R2-encoding constructs may be part of the same viral vector or on different viral vectors. In some embodiments, the viral vector(s) are adeno-associated viral vectors. The viral vector(s) may be administered systemically, e.g. intravenously, or locally, e.g. via intra-myocardial injection. The viral vector(s) may further encode a targeting agent that specifically binds to a cardiac-specific marker. In some embodiments, the viral vector(s) further comprise a transduction reporter. In still other embodiments, the method further includes administration of a viral vector comprising a nucleic acid sequence encoding a L48Q cTnC variant, wherein the cTnC variant exhibits an increased binding affinity for Ca$^{2+}$ and the nucleic acid sequence is operably linked to a cardiac-specific promoter.

In another aspect of the invention, methods of delivering dATP to a myocardium of a mammalian host, e.g. human host, are provided. Donor cells which overexpress ribonucleotide reductase subunit R1 and ribonucleotide reductase subunit R2 are grafted to the myocardium. In certain embodiments, the donor cells contain a first expression vector comprising a first nucleic acid sequence encoding ribonucleotide reductase subunit R1 and a second expression vector comprising a second nucleic acid sequence encoding ribonucleotide reductase subunit R2, said first nucleic acid sequence and second nucleic acid sequence being operably linked to a promoter that induces overexpression of R1 and R2. Those of skill in the art would appreciate that the R1 and R2-encoding constructs may be part of the same expression vector.

dATP is produced by the ribonucleotide reductase complex in situ and transferred to cardiomyocytes of the mammalian host through gap junctions established between the donor cells and host cardiomyocytes. In some embodiments, dATP is delivered to an infarcted myocardium. In preferred embodiments, the dATP is delivered to a region of the myocardium containing live cells, e.g. a non-infarct zone. Grafting of the donor cells, e.g. cardiomyocytes, fibroblasts, may be affected via delivery by catheter. As those of skill in the art would appreciate, the cardiomyocytes may be derived from stem cells, e.g. pluripotent ESC, iPSC, mesenchymal stem cells, selected from an origin compatible with the host organism. For instance, the iPSCs are derived from a cell, e.g. fibroblast, harvested from the mammalian host.

In still another aspect of the invention, methods of improving cardiac function in an individual by administration of a L48Q cTnC variant-encoding viral vector are provided, wherein the nucleic acid sequence encoding the cTnC variant is operably linked to a cardiac-specific promoter. L48Q cTnC variants exhibit increased site II Ca2+ binding affinity. In some embodiments, the individual has a heart condition resulting in reduced contraction. These methods may be applied to individuals diagnosed with cardiomyopathies, e.g. ischemic heart disease, cardiomyopathy, myocardial infarction, or as characterized by reduced systolic function. Exemplary cardiopathologies include, without limitation, primary cardiomyopathy, genetic cardiomyopathy, and dilated cardiomyopathy. In some embodiments, the individual in need of therapy has one or more genetic mutation(s) associated with decreased Ca2+ sensitivity of myofibril contraction and/or dilated cardiomyopathy phenotypes. Examples of such genetic mutations include, without limitation, missense mutations Ser532Pro and Phe764Leu, deletion in cTnT (deltaLys210), or mutations in genes MYH7, MYBPC3, TNNT2, TNNI3, TPM1, ACTC, MYL2, MYL3, or combinations thereof as documented in the literature.

Alternatively, cardiac function can be improved in individuals having one or more genetic mutation(s) in a sarcomeric protein selected from beta-cardiac myosin heavy chain, cardiac actin, cardiac troponin T, alpha-tropomyosin, cardiac troponin I, cardiac myosin-binding protein C, and myosin light chain, which is associated with increased $Ca^{2+}$ sensitivity of myofibril contraction and/or hypertrophic cardiomyopathy phenotypes. Examples of such genetic mutations include, without limitation, mutations at residue 92 of cTnT, e.g. R92W, R92Q, and R92L cTnT, or mutations at MYH7, MYBPC3, TNNT2, TNNI3, TPM1, ACTC, MYL2, MYL3, and combinations thereof as documented in the literature. The method of improving cardiac function involves administering said individuals having the $Ca^{2+}$ sensitized genetic mutation(s) a viral vector comprising a nucleic acid sequence encoding a L57Q or I61Q cTnC variant, said nucleic acid sequence being operably linked to a cardiac-specific promoter. L57Q and I61Q cTnC variants exhibit decreased site II Ca2+ binding affinity and can be used to treat individuals diagnosed with a hypertrophic cardiomyopathy. In some embodiments, the L48Q, L57Q or I61Q cTnC variant-encoding viral vectors are administered by, e.g. lipofection, coating on a stent, or direct injection such as vai a catheter. The viral vectors may be selected from adeno-associated viral vectors.

In yet another aspect of the invention, pharmaceutical compositions for improvement of cardiac function, and/or myocardial contractility and/or myocardial relaxation are provided. The pharmaceutical compositions may contain a first viral vector comprising a first nucleic acid sequence encoding ribonucleotide reductase subunit R1 and a second viral vector comprising a second nucleic acid sequence encoding ribonucleotide reductase subunit R2, said first nucleic acid sequence and second nucleic acid sequence being operably linked to a cardiac-specific promoter. In some embodiments, the R1 and R2-encoding constructs are on the same viral vector or on different viral vectors. Alternatively, the pharmaceutical compositions contain cardiomyocytes that have been transduced with the R1 and R2-encoding viral vector(s). Other pharmaceutical compositions described herein comprises a viral vector having a L48Q cTnC variant-encoding, and/or a I61Q cTnC variant-encoding, and/or a L57Q cTnC variant-encoding nucleic acid sequence. The viral vectors may be selected from adeno-associated viral vectors, e.g. AAV6, AAV2, rAAV2/1, rAAV2/2, rAAV2/3, rAAV2/4, rAAV2/5, rAAV2/6, rAAV2/7 rAAV2/8, rAAV2/9, rAAV2/10, rAAVM41, dsAAV, etc. In some embodiments, viral vector(s) further comprise a CMV promoter operably linked to the nucleic acid sequence encoding the cTnC variant. It is envisioned that the vector may further include a nucleic acid sequence encoding a targeting agent as deemed appropriate by one of skill in the art.

GFP transduced myocytes, stimulated at 0.5 Hz, as compared to non-treated myocytes. $V_{short}$=velocity of shortening; FS=fractional shortening; $V_{rel}$=maximal relaxation velocity; $RT_{50,90}$=time to 50% and 90% relaxation, respectively; FL=fluorescence; $DT_{50,90}$=time to 50% and 90% Ca2+ decay, respectively. *p<0.05 as compared to No Treatment.

Figure 7:
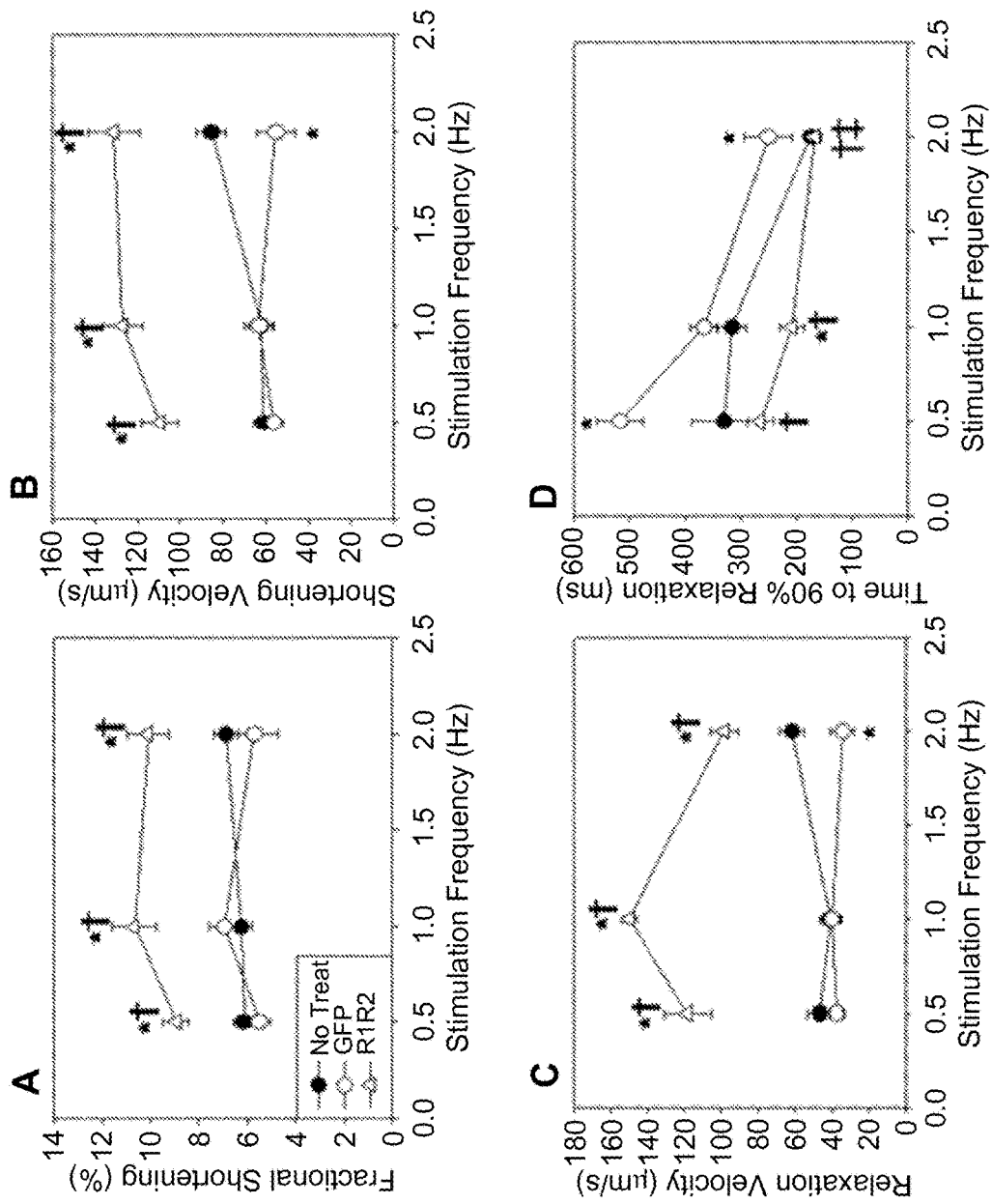

FIG. 7. Effect of stimulation frequency on contractile properties. Rrm1+Rrm2 transduced myocytes (open triangles) respond similarly to stimulation frequency as GFP-only transduce open circles) and non treated myocytes (closed circles) but show elevated fractional shortening (A) and shortening velocity (B) at all frequencies. Relaxation velocity (C) and time to 90% relaxation (D) are also similar between groups, with time to relaxation shortening as stimulation frequency increases. *=p<0.05 as compared to No Treat, †=p<0.05 as compared to GFP, ‡=p<0.05 as compared to 0.5 Hz for all groups.

Figure 8:
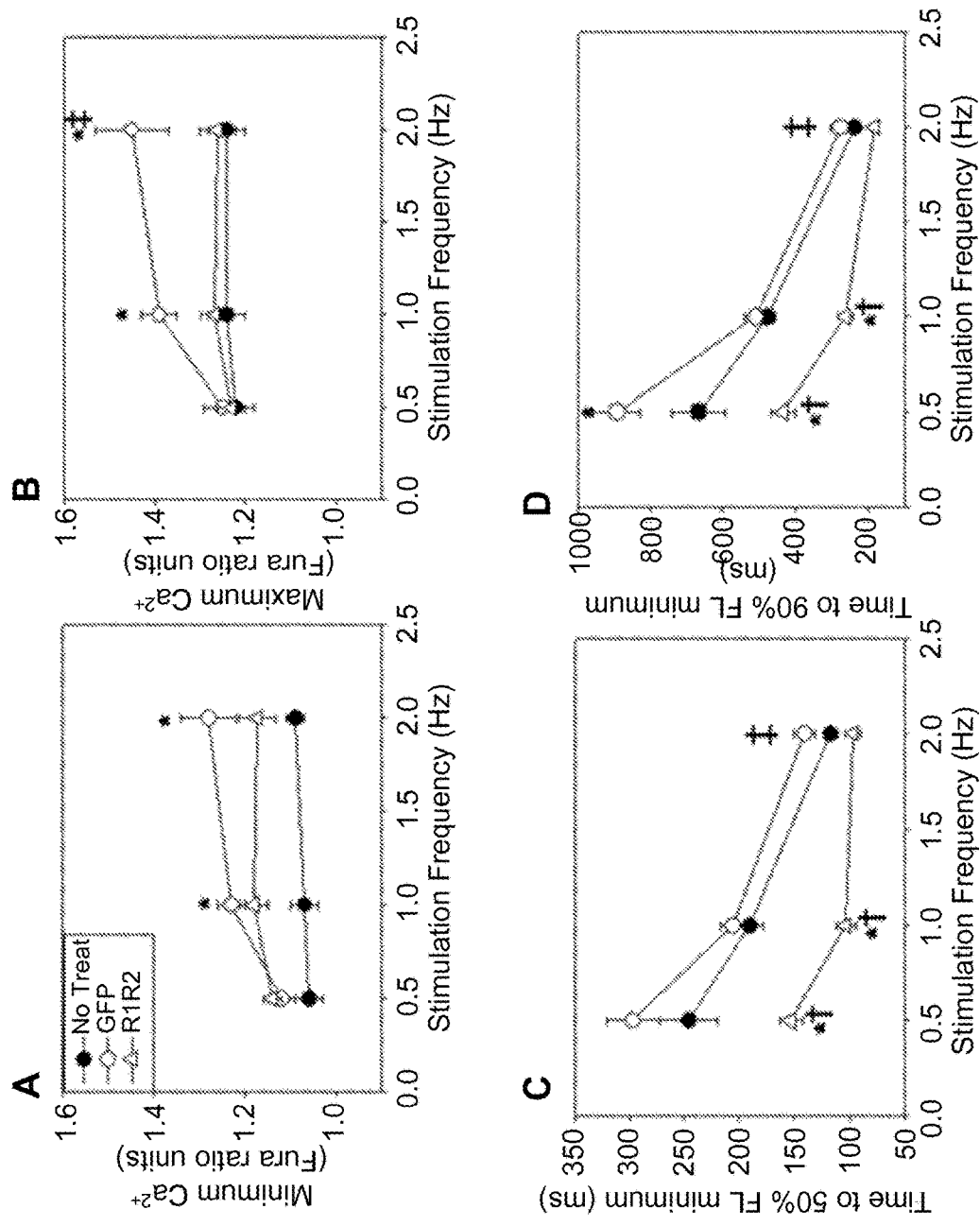

FIG. 8. Effect of stimulation frequency on Ca2+ handling properties. Rrm1+Rrm2 transduced myocytes (open triangles) respond similarly to stimulation frequency as non-treated myocytes (closed circles) in minimal (A) and maximal (B) fluorescence, while GFP-only transduced myocytes (closed circles) showed a greater increase in both as frequency increased. As with cardiomyocyte relaxation, Ca2+ transient decay time (DT) to 50% (C) and 90% (D) is shortened with increased stimulation frequency, but both are dramatically shortened in R1R2 transduced cardiomyocytes. *=p<0.05 as compared to No Treat, †=p<0.05 as compared to GFP, ‡=p<0.05 as compared to 0.5 Hz for all groups.

Figure 9:
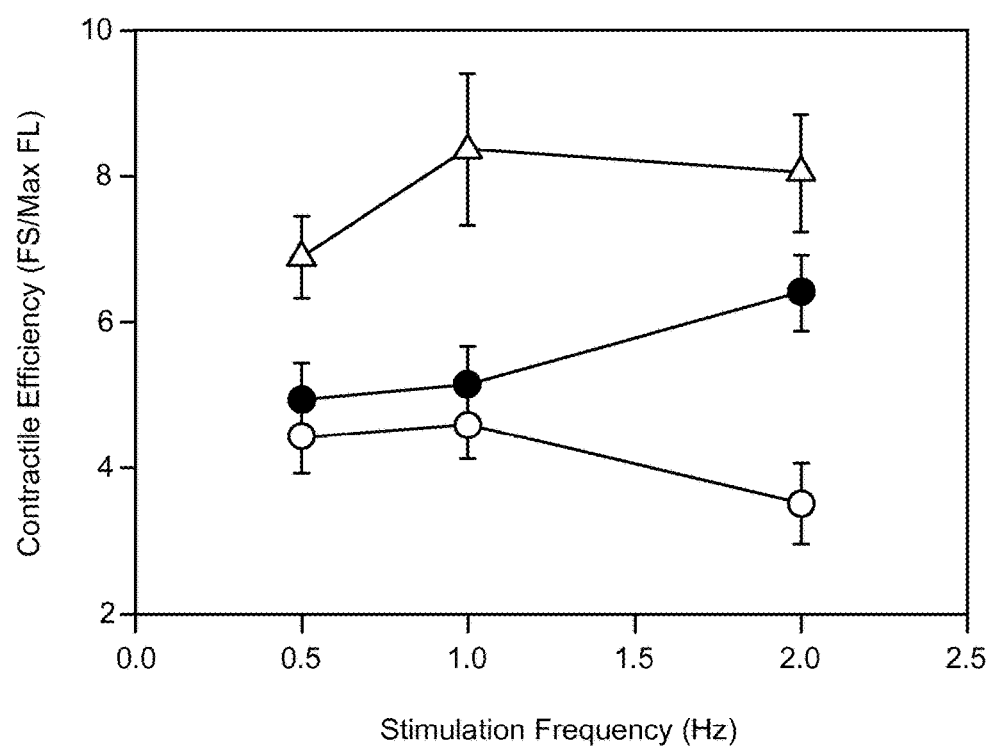

FIG. 9. Contractile efficiency as assessed as fractional shortening divided by maximal fura fluorescence (peak Ca2+) indicates Rrm1+Rrm2 transduced cardiomyocytes (open triangles) are significantly more responsive to Ca2+ at all stimulation frequencies, while GFP-only transduced cardiomyocytes (open circles) are less responsive to Ca2+ only at 2 Hz stimulation frequency as compared to non-treated cardiomyocytes (closed circles). *=p<0.05 as compared to No Treat, †=p<0.05 as compared to GFP.

Figure 10:
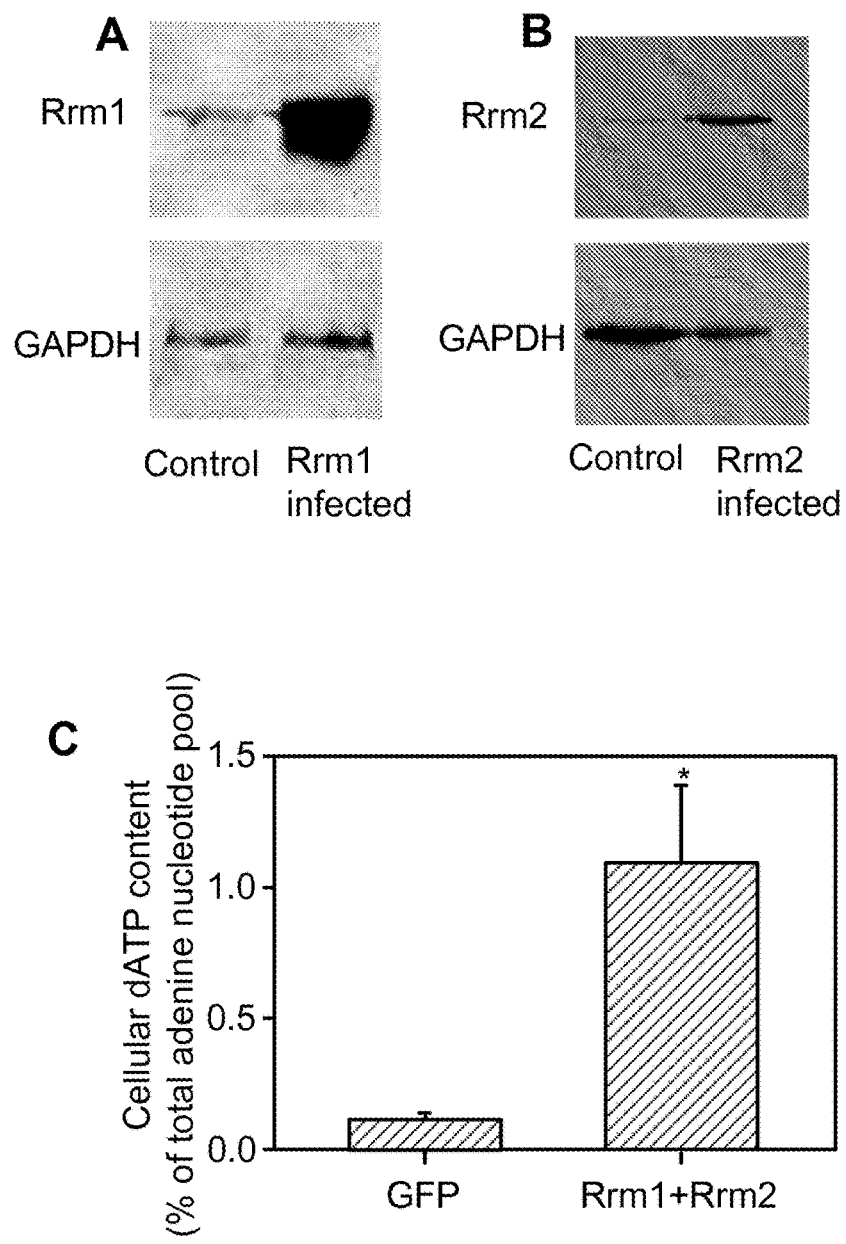

FIG. 10. (A) Western blot of Rrm1 transfected neonatal rat cardiomyocytes probed with anti-Rrm1 antibody indicates a >24-fold increase in Rrm1. (B) Western blot of Rrm2 transfected neonatal rat cardiomyocytes probed with anti-Rrm2 antibody indicates a >46-fold increase in Rrm2. Rrm1+Rrm2 overexpression significantly increased intracellular [dATP] by >10-fold in neonatal rat cardiomyocytes as assessed by HPLC analysis. *=p<0.05 as compared to GFP transduced cardiomyocytes.

Figure 11:
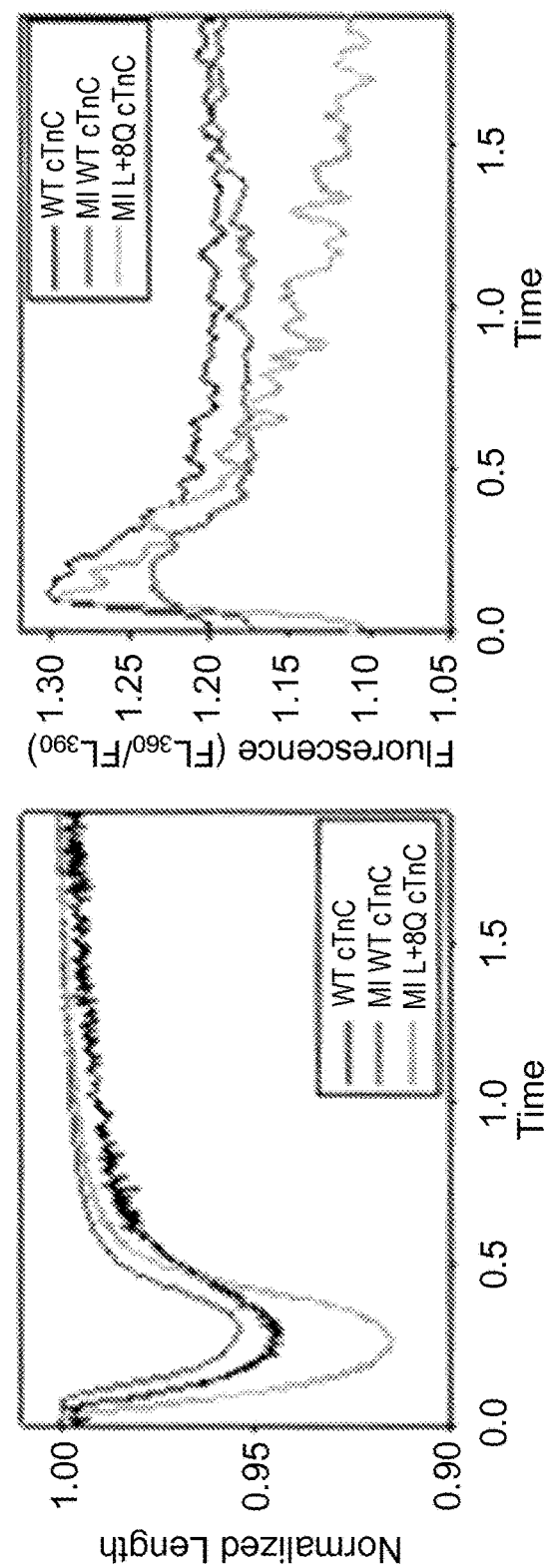

FIG. 11. Shortening (A) and $Ca^{2+}$ (B) traces from AV-cTnC transfected myocytes: non-infarcted (WT cTnC, black), infarcted control (WT cTnC, red), and infarcted (L48Q cTnC, green).

Figure 12:
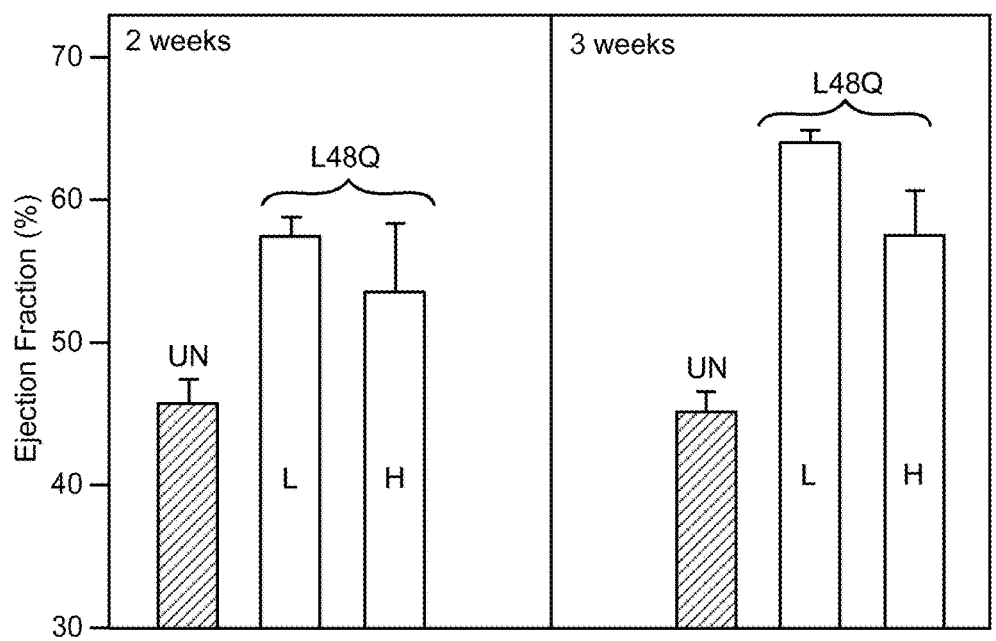

FIG. 12. LV ejection fraction at 2 wks (left) and 3 wks (right) for untreated (UN; n=5) vs. low (L; n=3) or high (H; n=3) dose of AAV6-L48Q.

Figure 13:
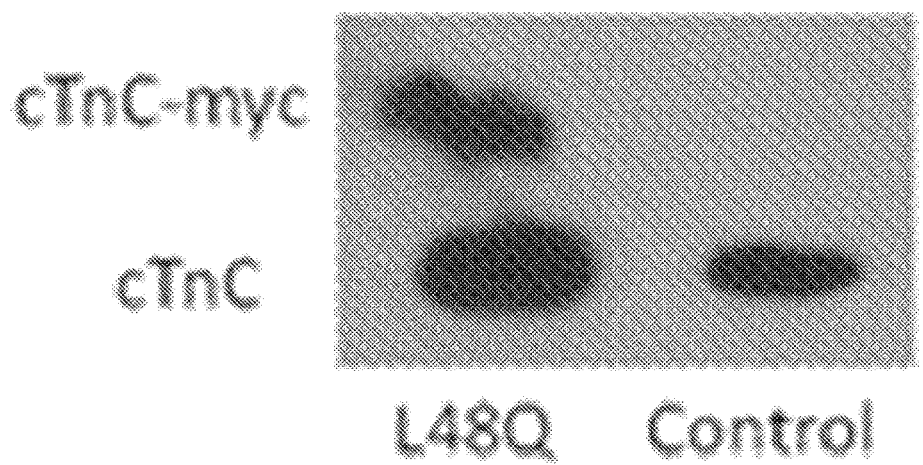

FIG. 13. Anti-cTnC western blot for AAV6 L48Q cTnC injected mouse cardiac tissue (left) and uninjected control (right).

Figure 14:
Figure 14:
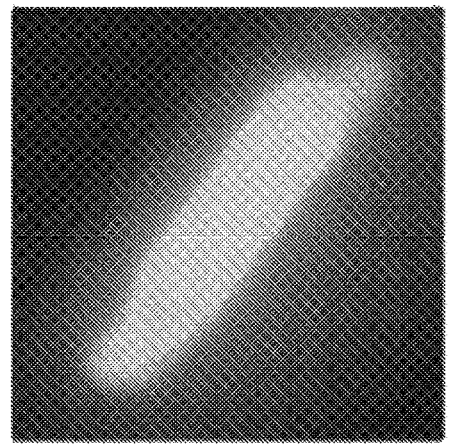

FIG. 14. Brightfield (left) and fluorescent (right) images of an AV transfected cell.

Figure 15:
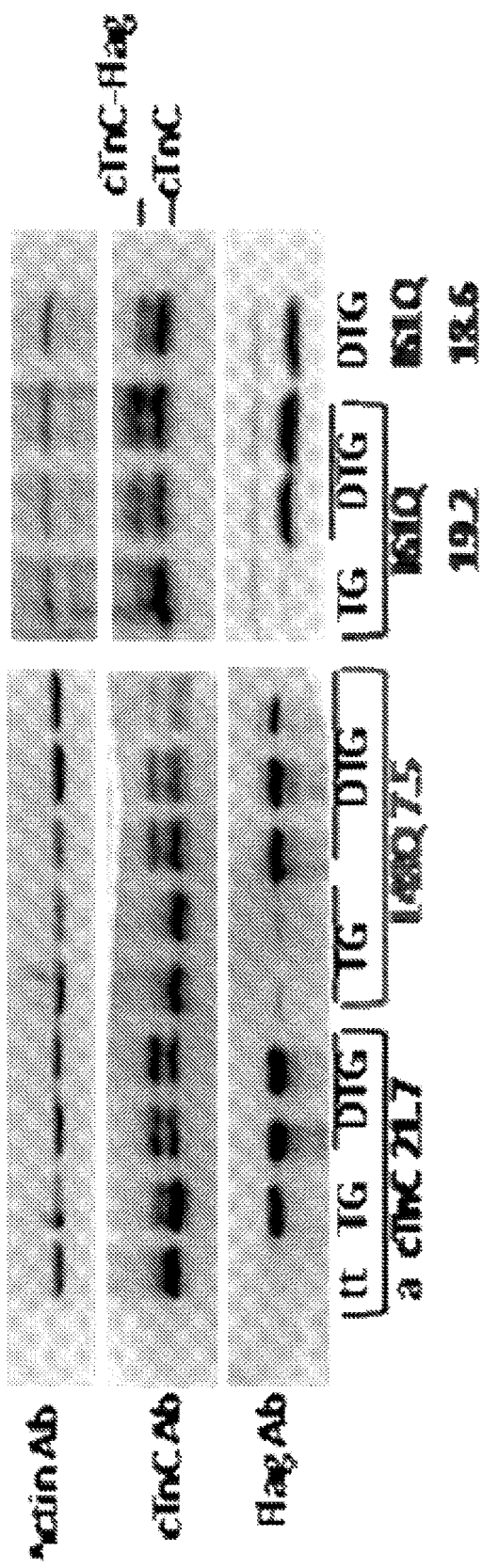

FIG. 15. Western blot analysis of myocardial tissue from transgenic animals (as labeled). Flag tagged cTnC shows as higher molecular weight, and densitometric analysis of flag-tagged vs. untagged cTnC indicates 40-50% replacement of native cTnC in Tg animals.

Figure 16:
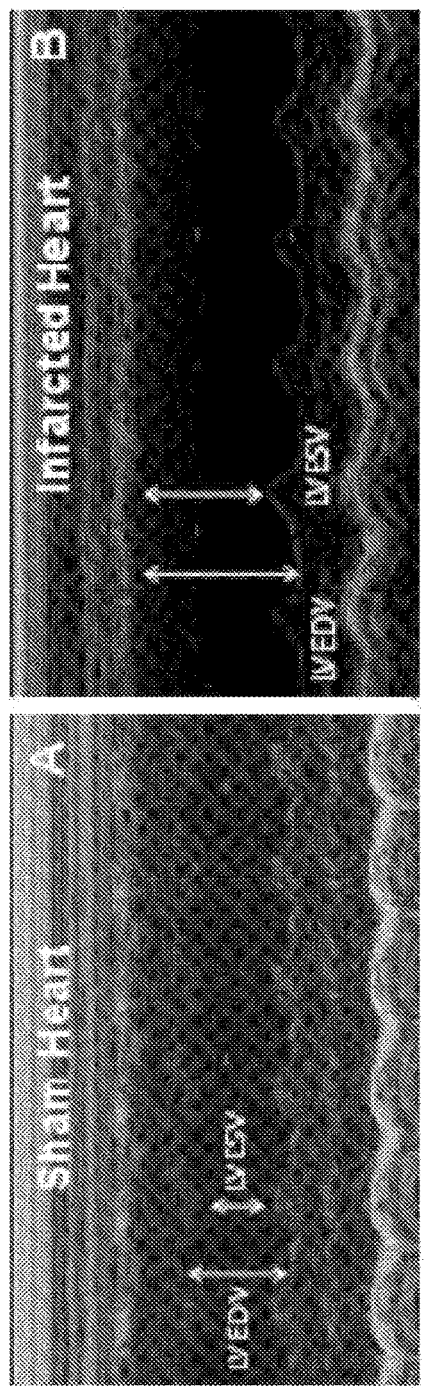
Figure 16:
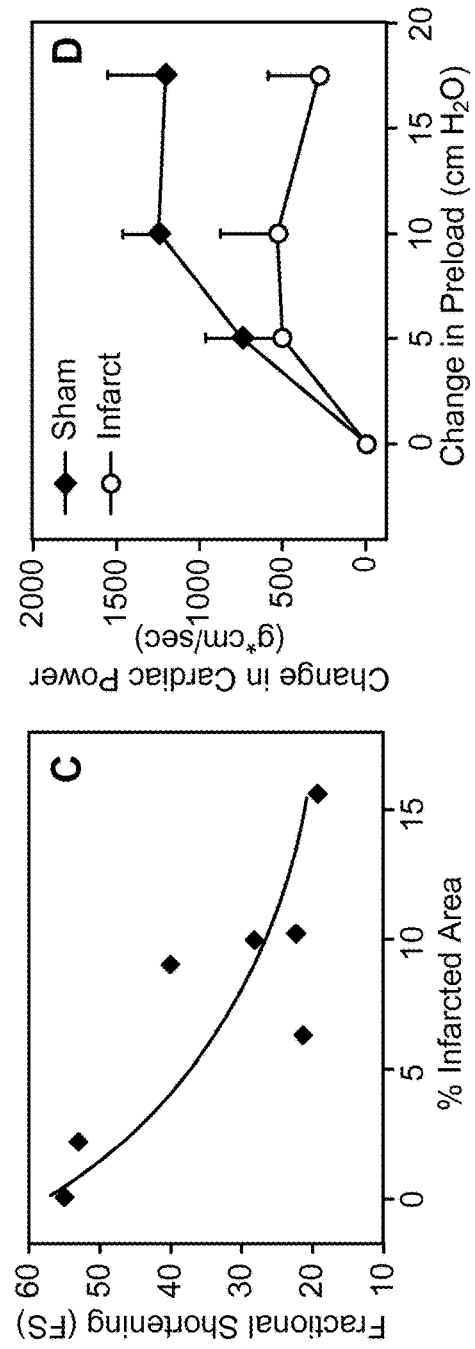

FIG. 16. Echocardiography (A-C) and working heart (D) measures of LV function demonstrating loss of function following infarct.

Figure 17:
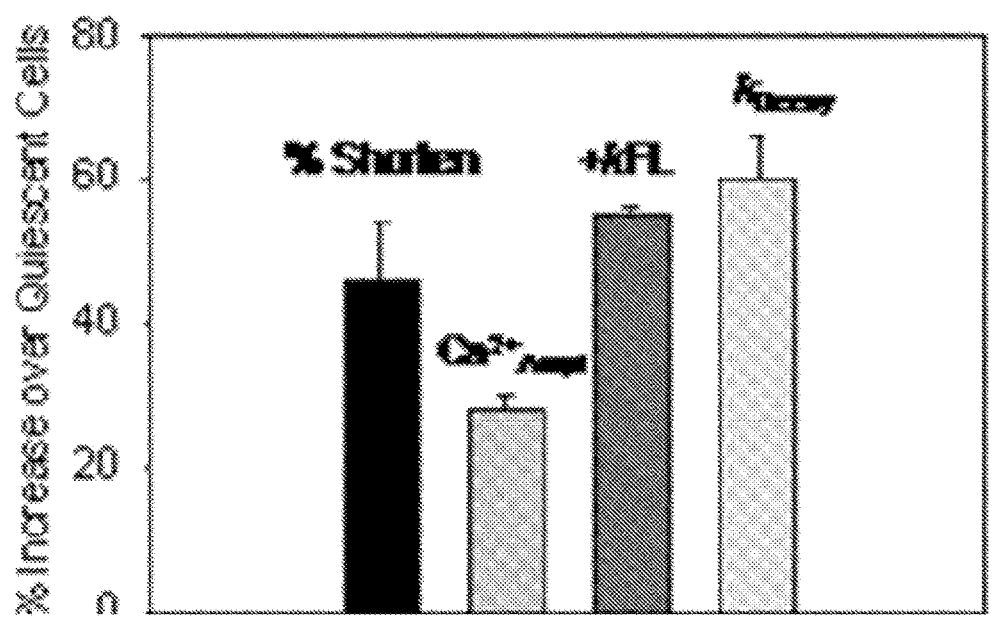

FIG. 17. Percent increased contraction and Ca2+ transient properties of cells with 1 Hz (30 hrs.) vs. no stimulation.

Figure 18:
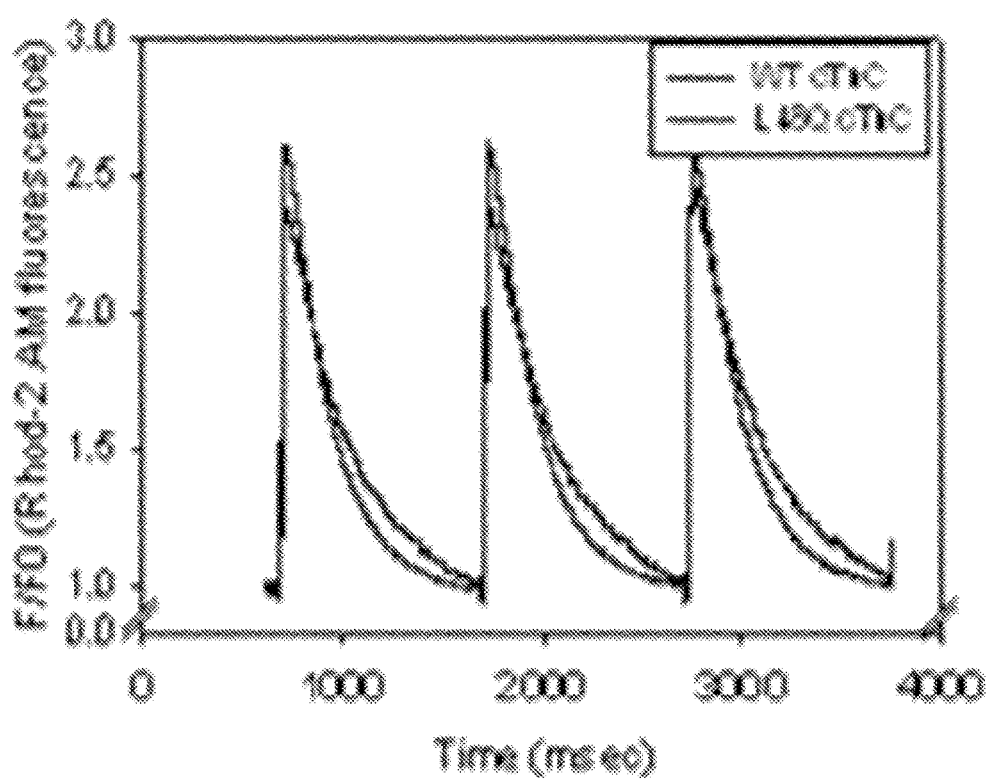

FIG. 18. Ca2+ transients (rhod-2) show faster decay with L48Q (blue) vs. WT (black) cTnC.

Figure 19:
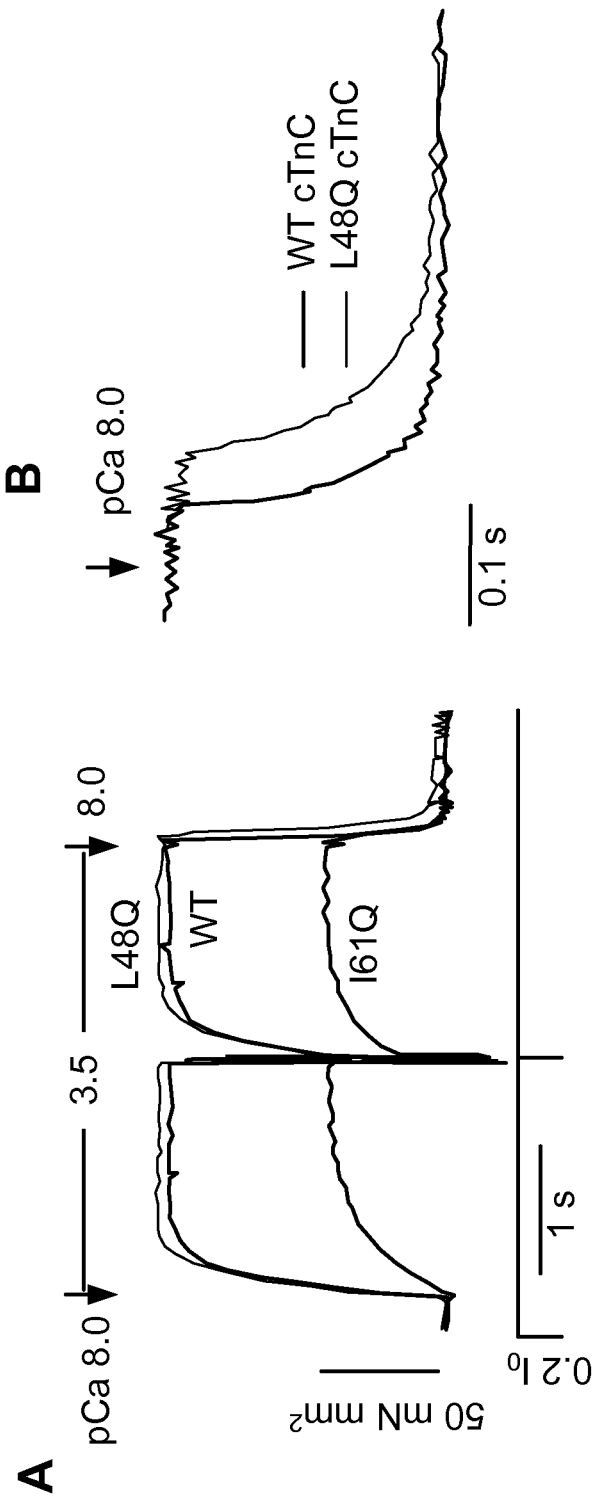

FIG. 19. (A) Cardiac myofibril activation and relaxation kinetics with rapid solution switching from pCa 8 to 3.5 to 8 following exchange with WT, I61Q (blue) or L48Q (red) cTnC. (B) Higher resolution relaxation traces for L48Q vs. WT cTnC.

Figure 20:
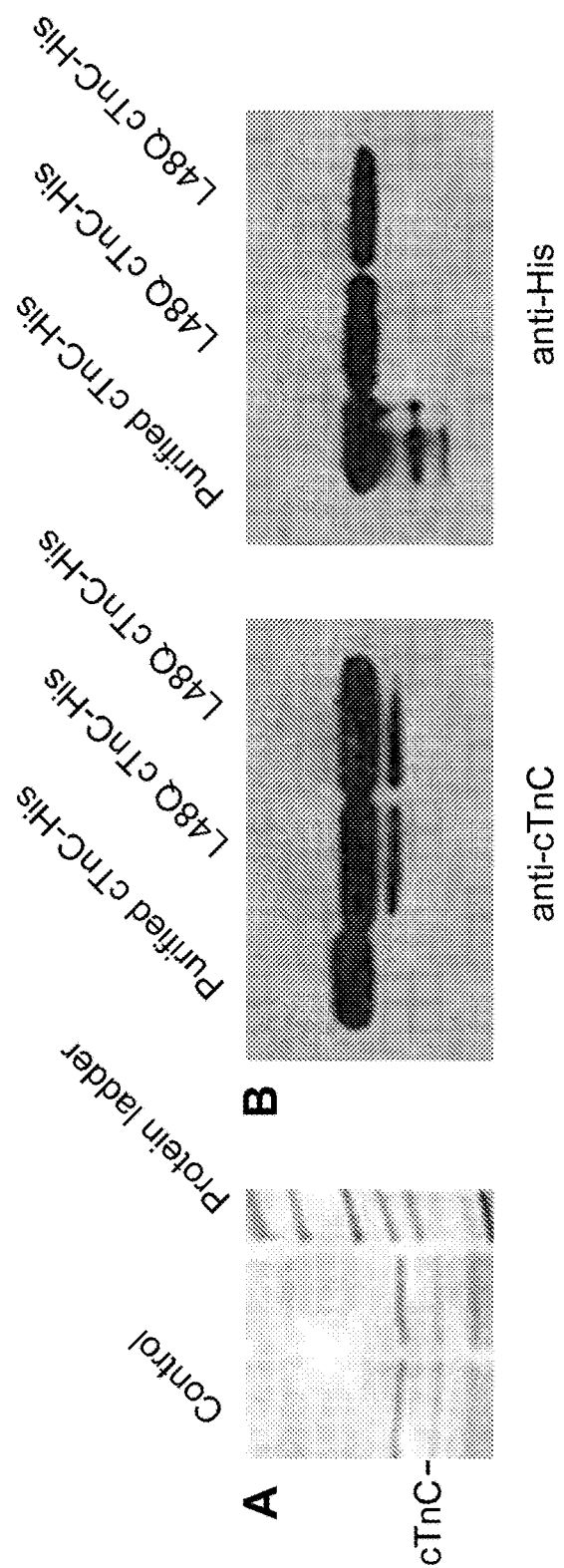

FIG. 20. (A) Silver stain of untreated and L48Q cTnC-His transduced cardiomyocyte myofilaments demonstrating maintenance of thin filament protein stoichiometry. (B) Western blots with anti-cTnC (left panel) show total cTnC myofilament content, those with anti-His (right panel) show 58±7% L48Q cTnC incorporation into thin filaments via densitometry.

Figure 21:
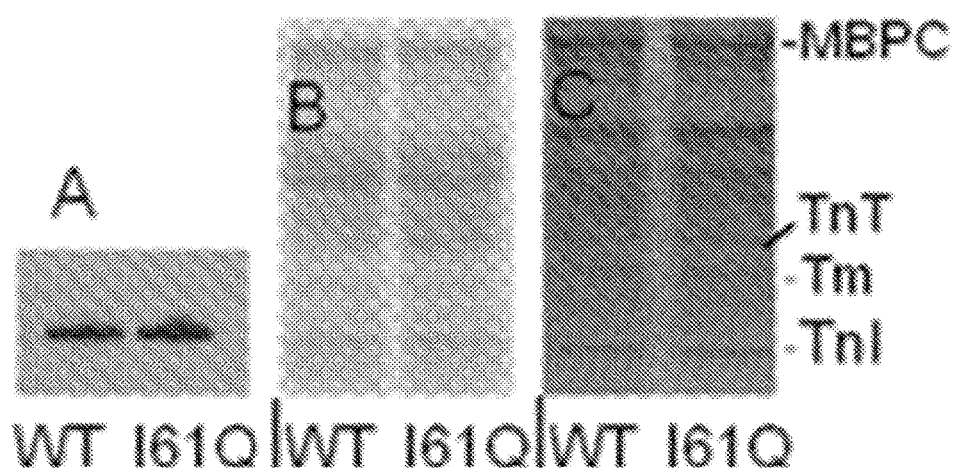

FIG. 21. Myofibril phosphorylation profile for WT vs. I61Q cTnC transfected cardiomyocytes. (A) Anti-phosphoserine western blot. (B) SDS Coomassie blue stain showing total protein. (C) Pro-Q diamond showing phosphorylation. No differences observed.

Figure 22:
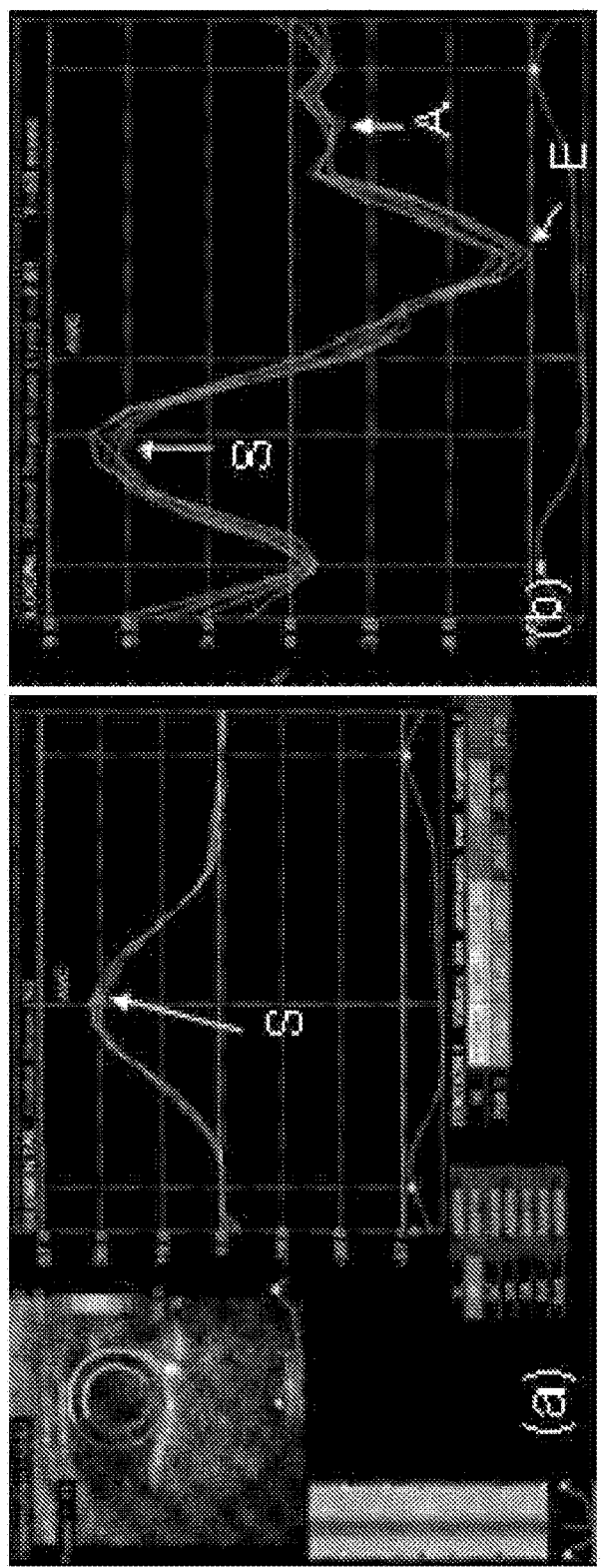

FIG. 22. Radial strain and strain rate using speckle tracking echo-cardiography. (a) mid-ventricular short axis view with color coded regions representing anterior, lateral, posterior, inferior, and septal heart segments for analysis for radial strain (upper left, arrow indicates systolic peak (S); each line corresponds to color-coded segments). (b) radial strain rate at systole and two diastolic periods—early (E) and late(A) diastole.

Figure 23:
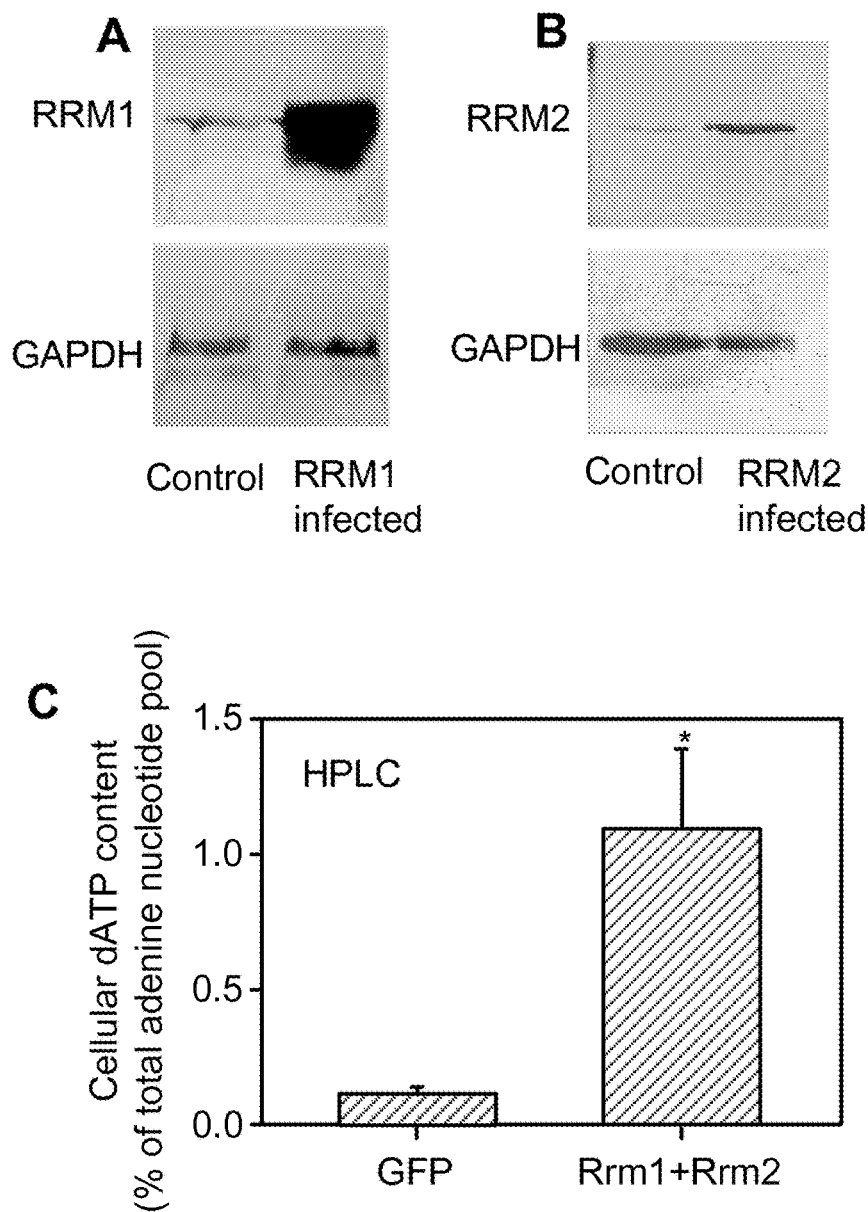

FIG. 23. Western blot for R1 (A) and R2 (B) with GAPDH as loading control. HPLC (C) of transfected cardiomyocytes [dATP].

Figure 24:
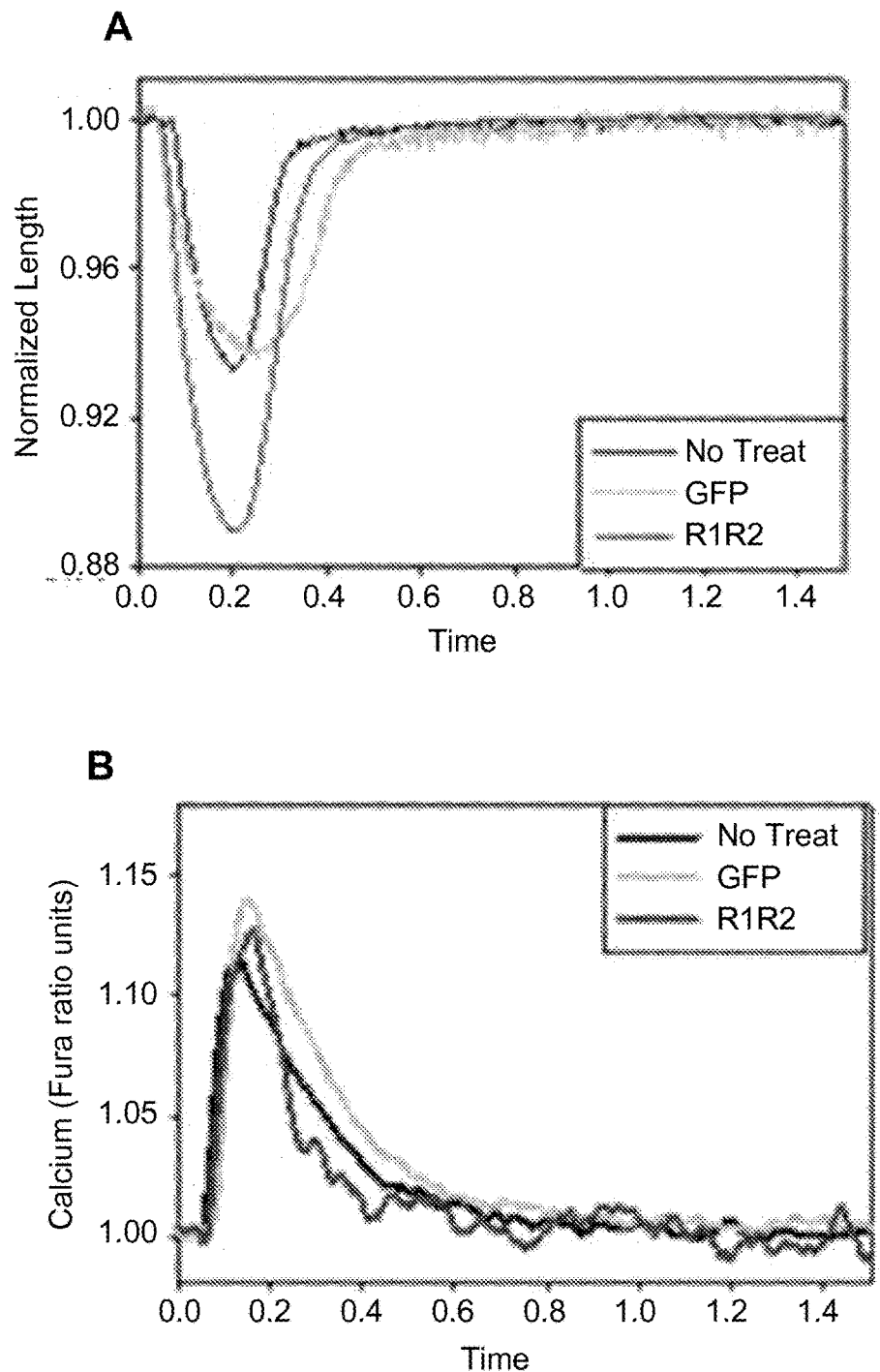

FIG. 24. Length (A) and $Ca^{2+}$ (B) transients indicates increased shortening with no change in $Ca^{2+}$ for R1R2 transfected cells vs. GFP and non-treated controls.

Figure 25:
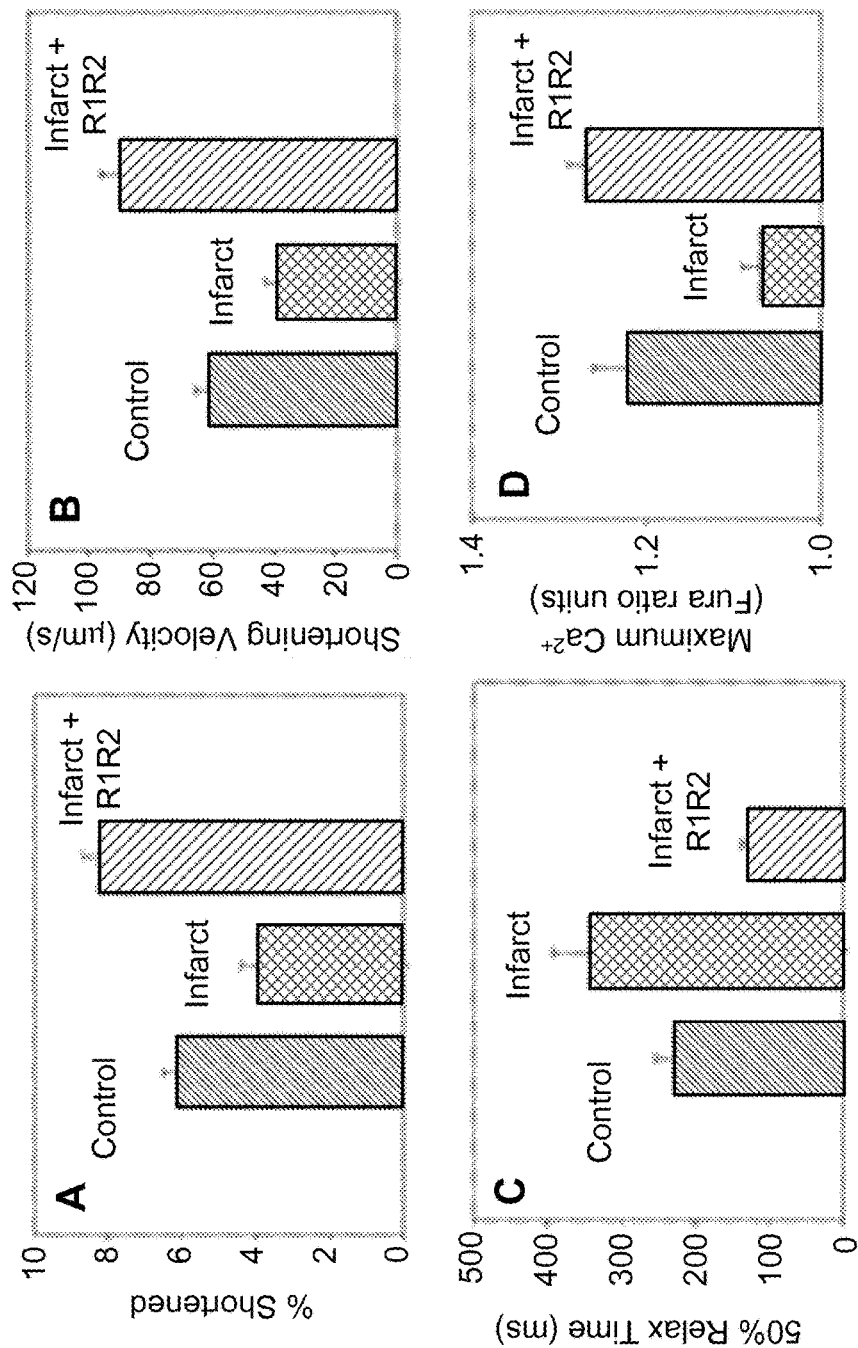

FIG. 25. Extent (A) and rate (B) of shortening, time to 50% relaxation (C) and maximal Ca2+ release (D) are all depressed in cardiomyocytes from infarcted hearts, but are rescued or improved over controls by AV-R1R2 transduction.

FIG. 26. (A) shows the increase in left ventricular fractional shortening for AV-R1R2 tail vein and direct cardiac injected mice as compared with control at 4 days post-injection; (B) Injected LV, demonstrating localized infection area, indicated by bright green fluorescence (from GFP).

Figure 27:
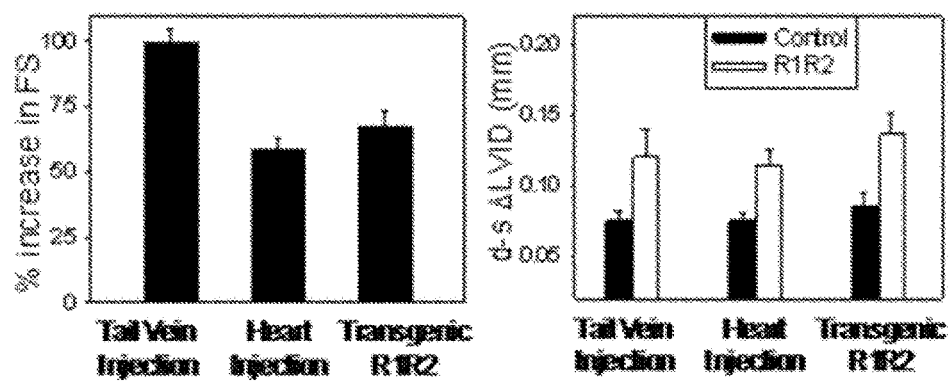

FIG. 27. Percentage fractional shortening increase (A) and change in left ventricular inner diameter (B) in R1R2 over-expressing mice vs. control littermates. d-diastole, s-systole.

Figure 28:
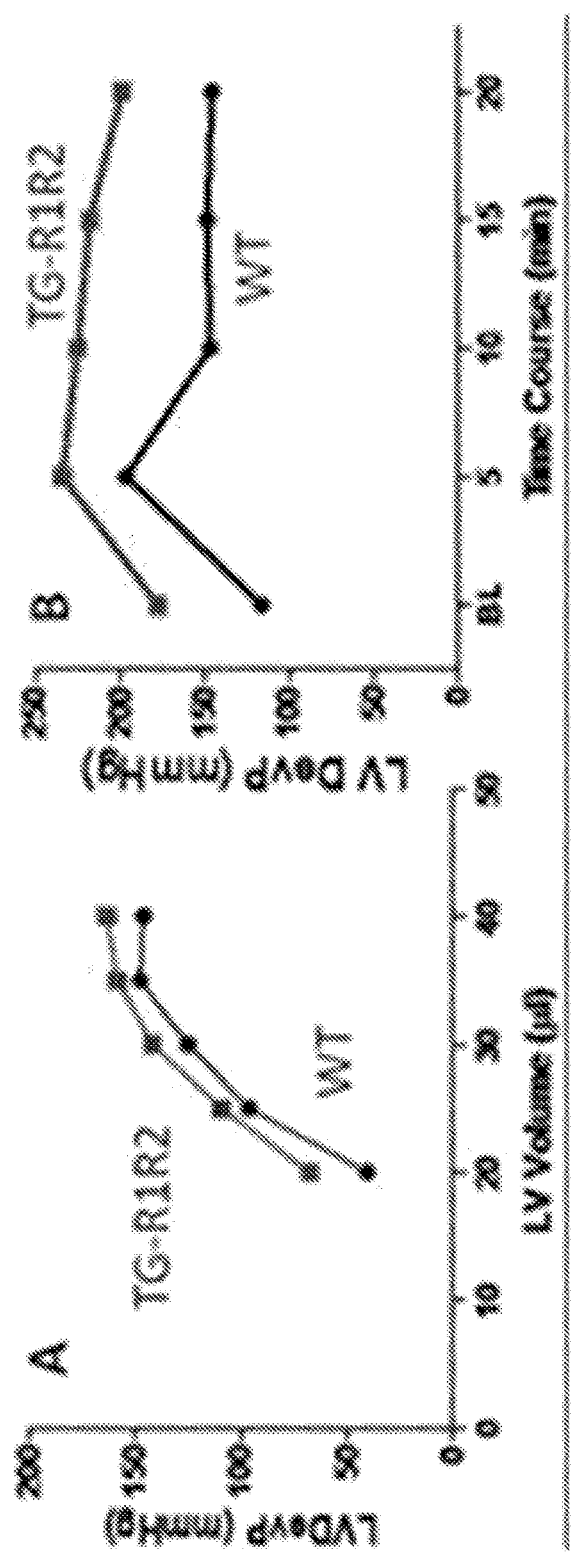

FIG. 28. LV pressure-volume relationship (A) and LV pressure response to high [$Ca^{2+}$] challenge (B).

Figure 29:
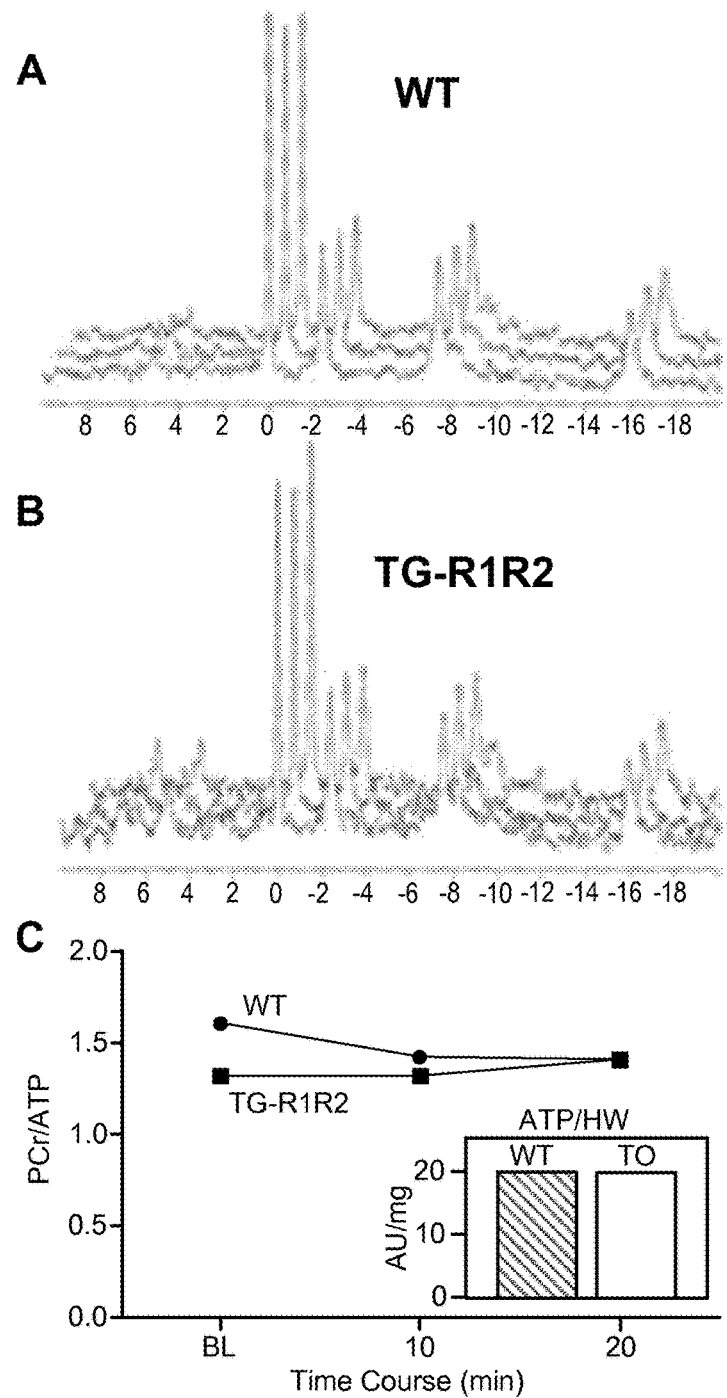

FIG. 29. NMR spectra for a WT (A) and a TG-R1R2 (B) hearts, and PCr/ATP ratio (C) at baseline and after high [Ca2+] challenge. ATP/HW ratio at baseline (inset).

Figure 30:
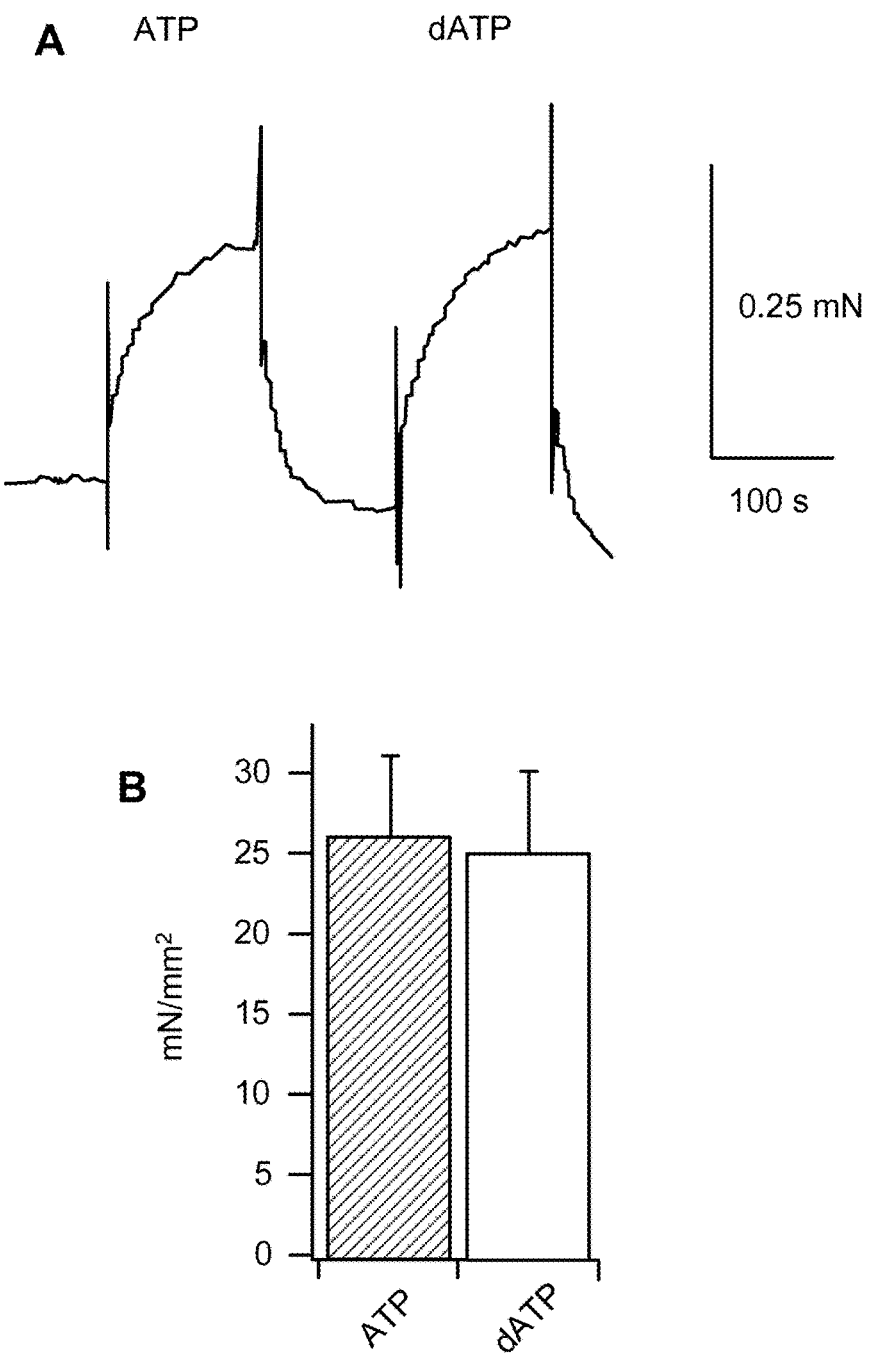

FIG. 30. Mouse aortic smooth muscle contraction traces with ATP and dATP (A) and summarized data (B).

Figure 31:
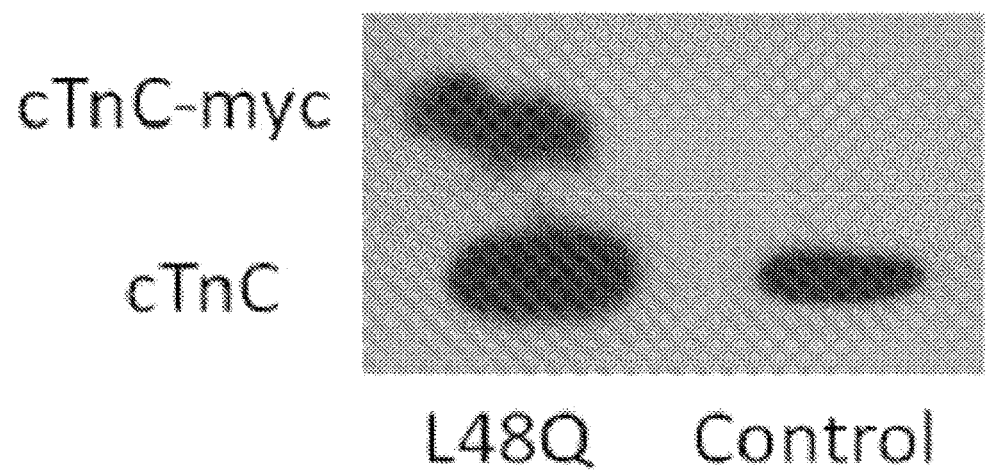

FIG. 31. Anti-cTnC western blot for AAV6 L48Q cTnC injected mouse cardiac tissue (left) and uninjected control (right).

Figure 32:
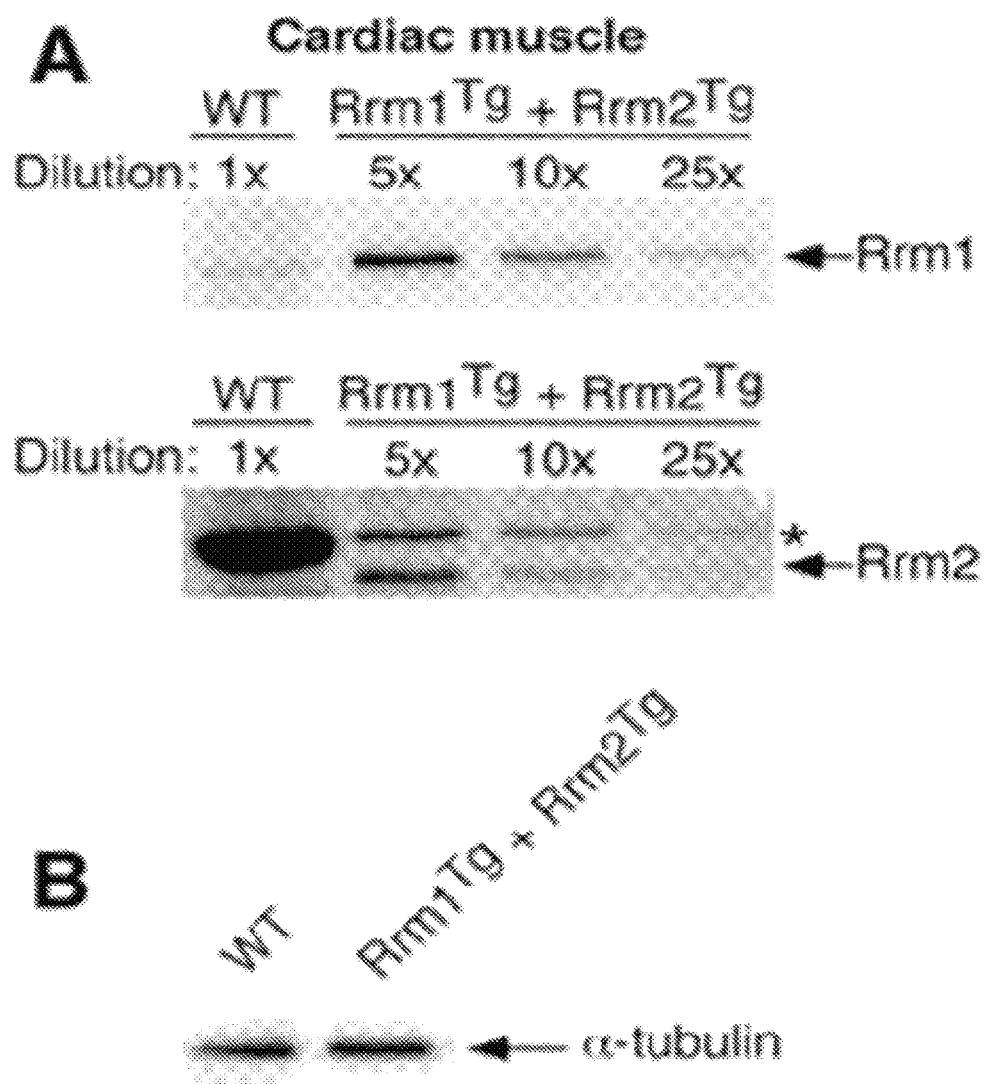

FIG. 32. Western blots for (A) R1 and R2 and (B) α-tubulin as loading control.

Figure 33:
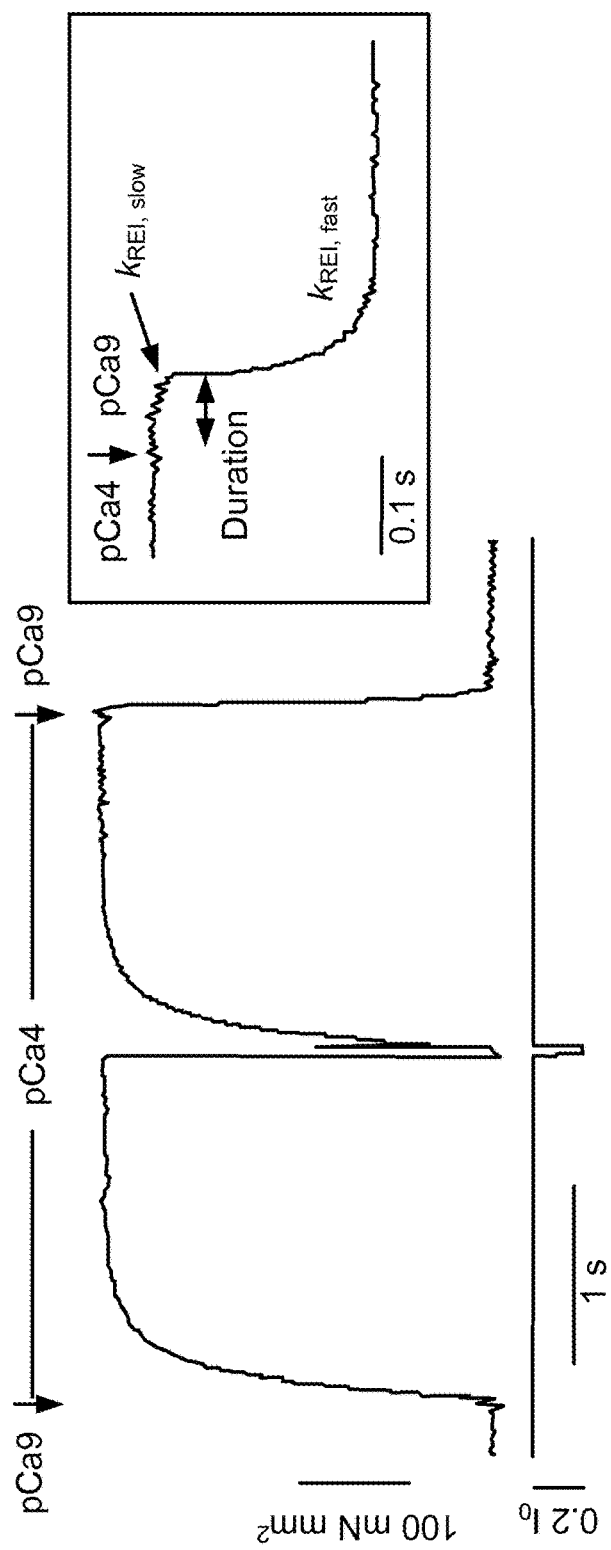

FIG. 33. Sample cardiac myofibril activation and relaxation trace (left). Magnified slow phase of relaxation (right).

Rate of tension rise ($k_{ACT}$). Slow phase of relaxation ($k_{REL, slow}$). Fast phase of relaxation ($k_{REL, fast}$). Slow phase duration ($t_{REL, slow}$).

Figure 34:
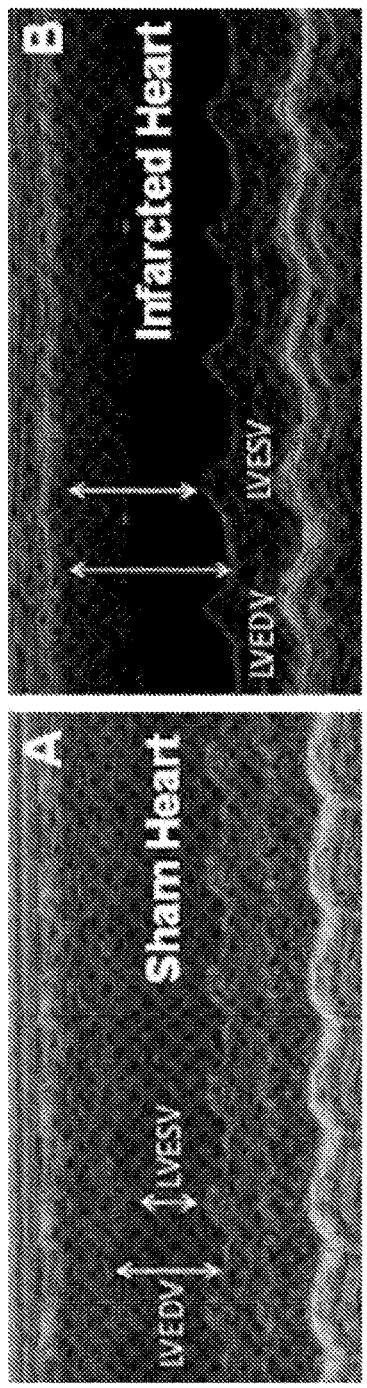
Figure 34:
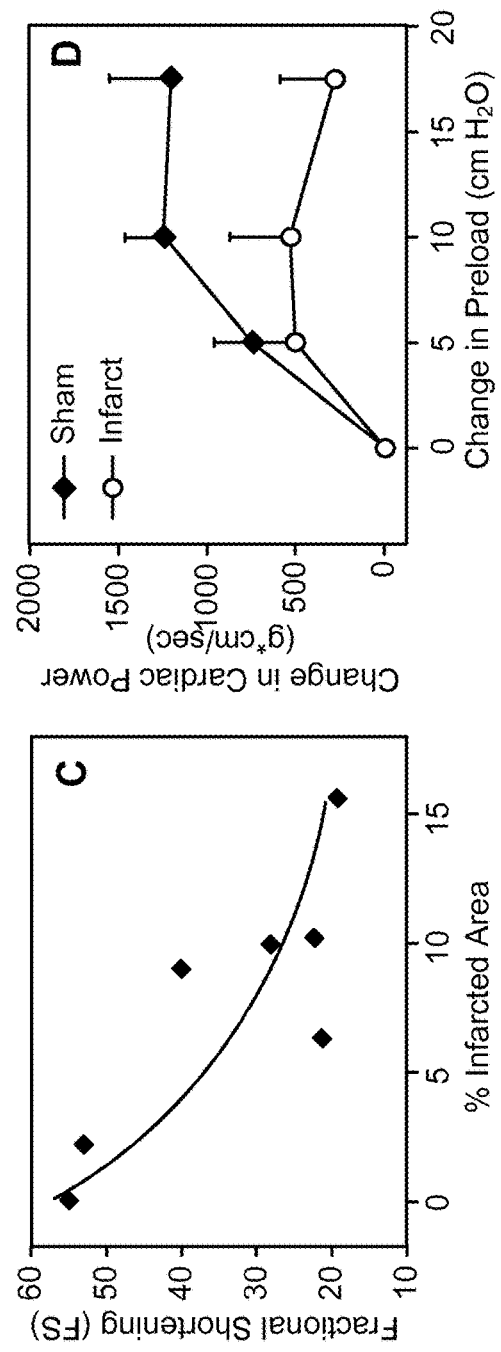

FIG. 34. Echocardiography (A-C) and working heart (D) measures of LV function demonstrating loss of function following infarct.

Figure 35:
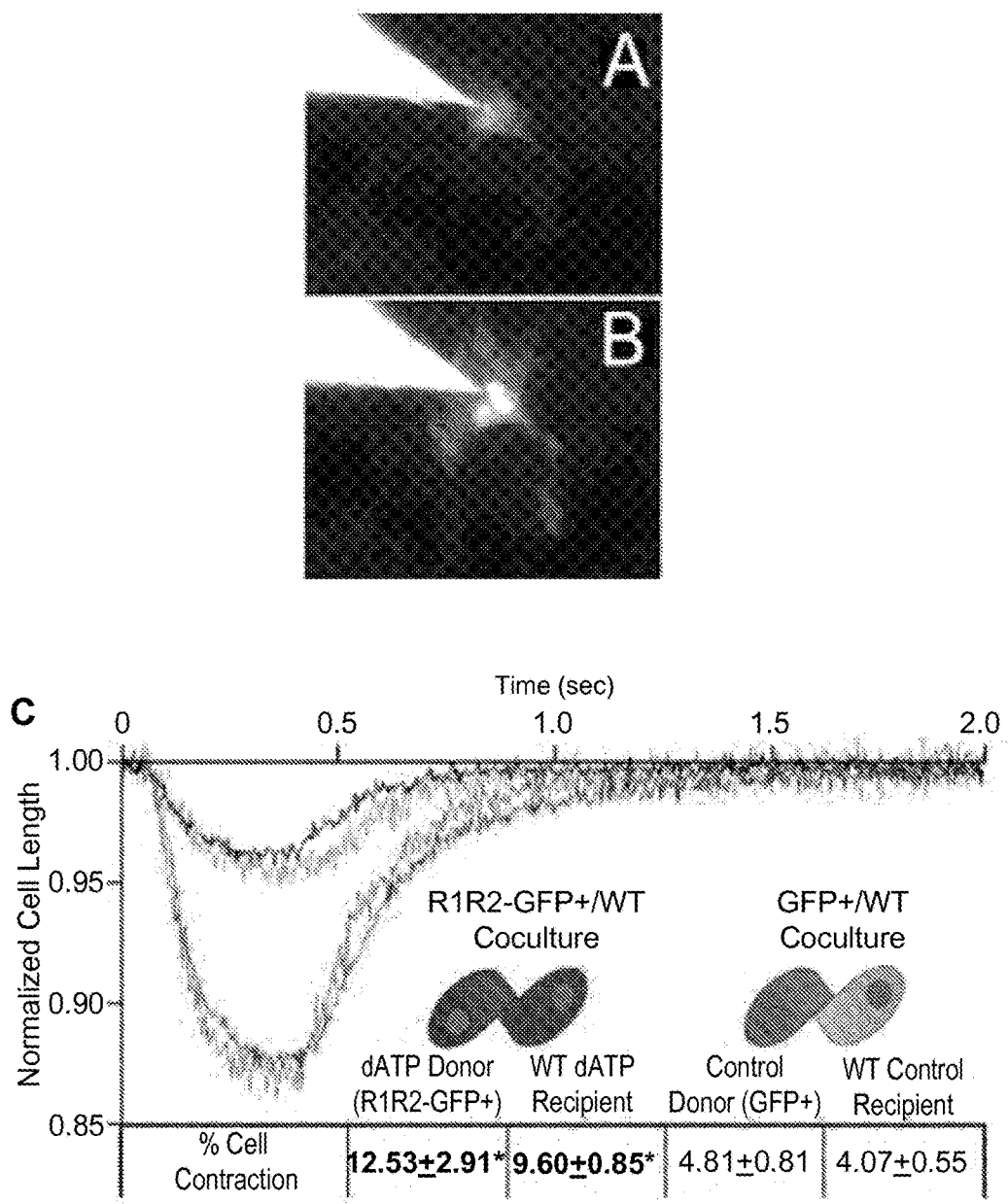

FIG. 35. Cell injection of labeled dATP into cultured hESC cardiomyocytes at 10 s (A) and 4 min(B). Co-culture with R1R2-overexpressing cardiomyocytes enhances the contractil properties of wildtype (recipient) myocytes (C). hESC-CMs were transduced with either AV-R1R2 or AV-GFP and these transduced myocytes were co-cultured with wildtype (WT), non-transduced Hesc-cmS. Both partners in co-cultures of AV-R1R2+GFP− transduced myocytes ("dATP donor cells", blue trace) and non-transduced myocytes (WT dATP recipients, red) showed greater contractility than their corresponding controls, i.e. AV-GFP transduced ("control donor" cells, green) or the latter's WT recipients (black). *p<0.05 vs controls.

Figure 36:
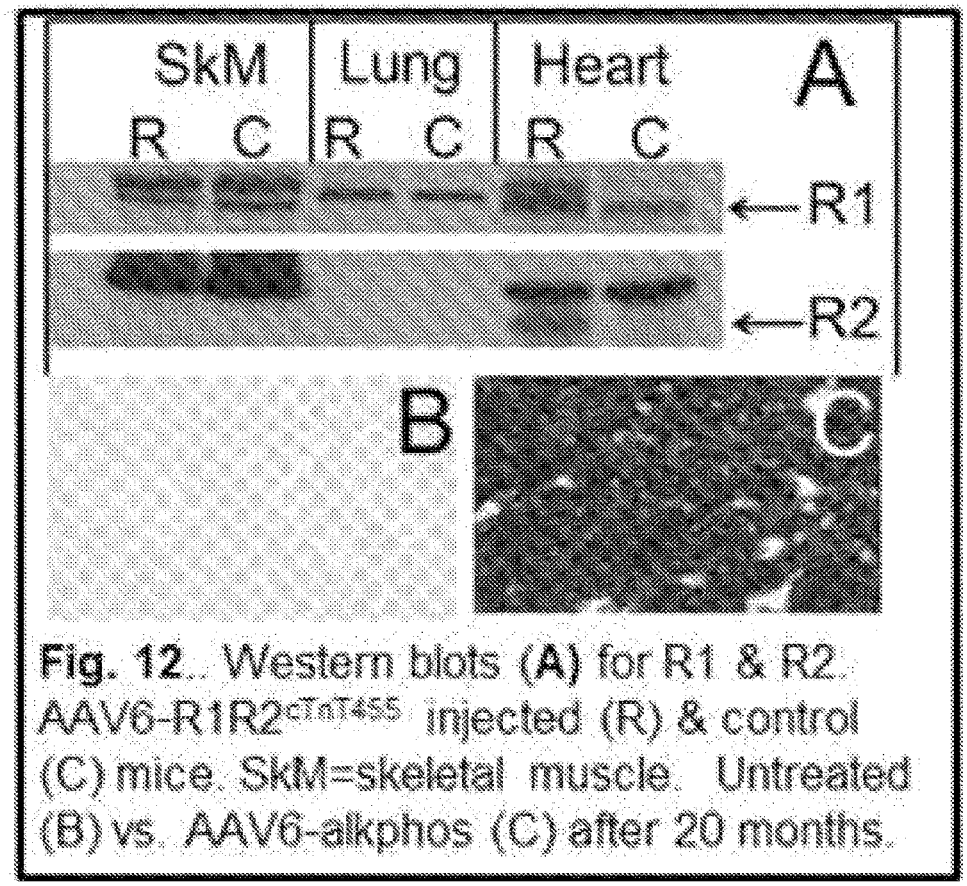

FIG. 36. FIG. 36A shows preliminary western blot evidence for the expression levels of R1 and R2 subunits in the skeletal muscle, lung, and heart of AAV6-R1R2$^{cTnT455}$ injected (4.5 e$^{13}$) mice and control mice. FIG. 36 also provides data for heart tissue from non-injected (B) vs. AAV6-alkaline phosphatase (purple; C) injected mice$^{36}$ after 20 months, suggesting AAV6-R1R2$^{cTnT455}$ should provide stable, long-term R1R2 over-expression.

Figure 37:
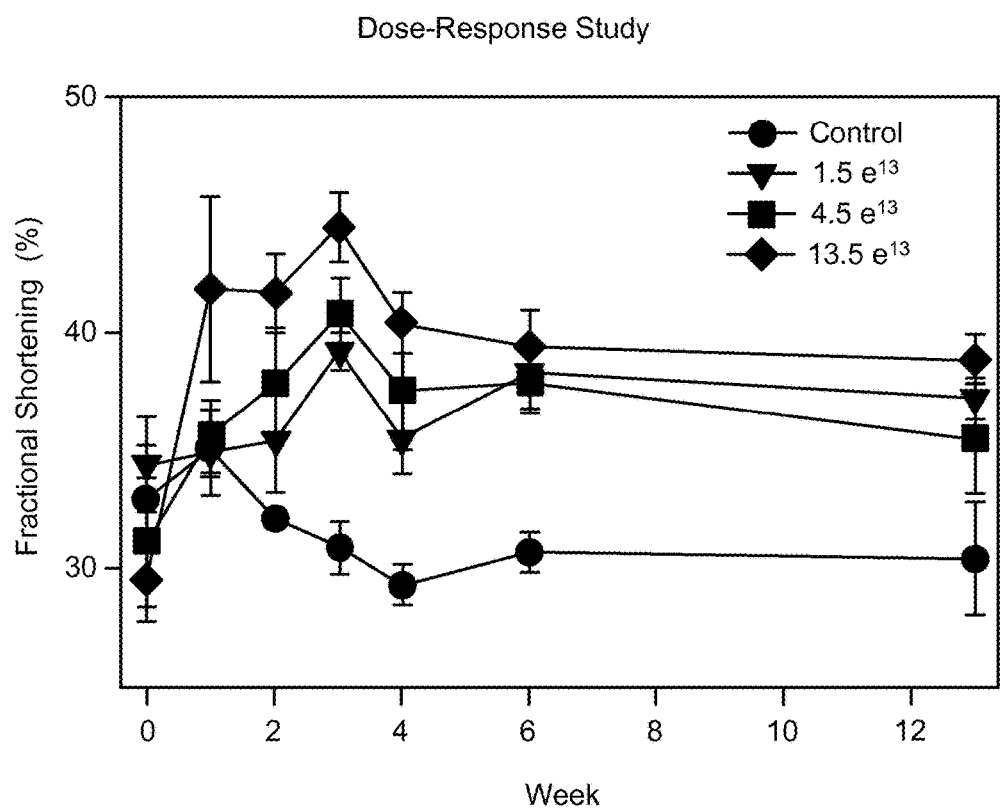

FIG. 37 shows the effect of 1.5 e$^{13}$, 4.5 e$^{13}$, 1.35 e$^{14}$ AAV6-R1R2$^{cTnT455}$ vector genomes or saline (control) injected systemically over an approximate 10-fold range into 3 month old mice (n=6 per group) on LV function.

Figure 38:
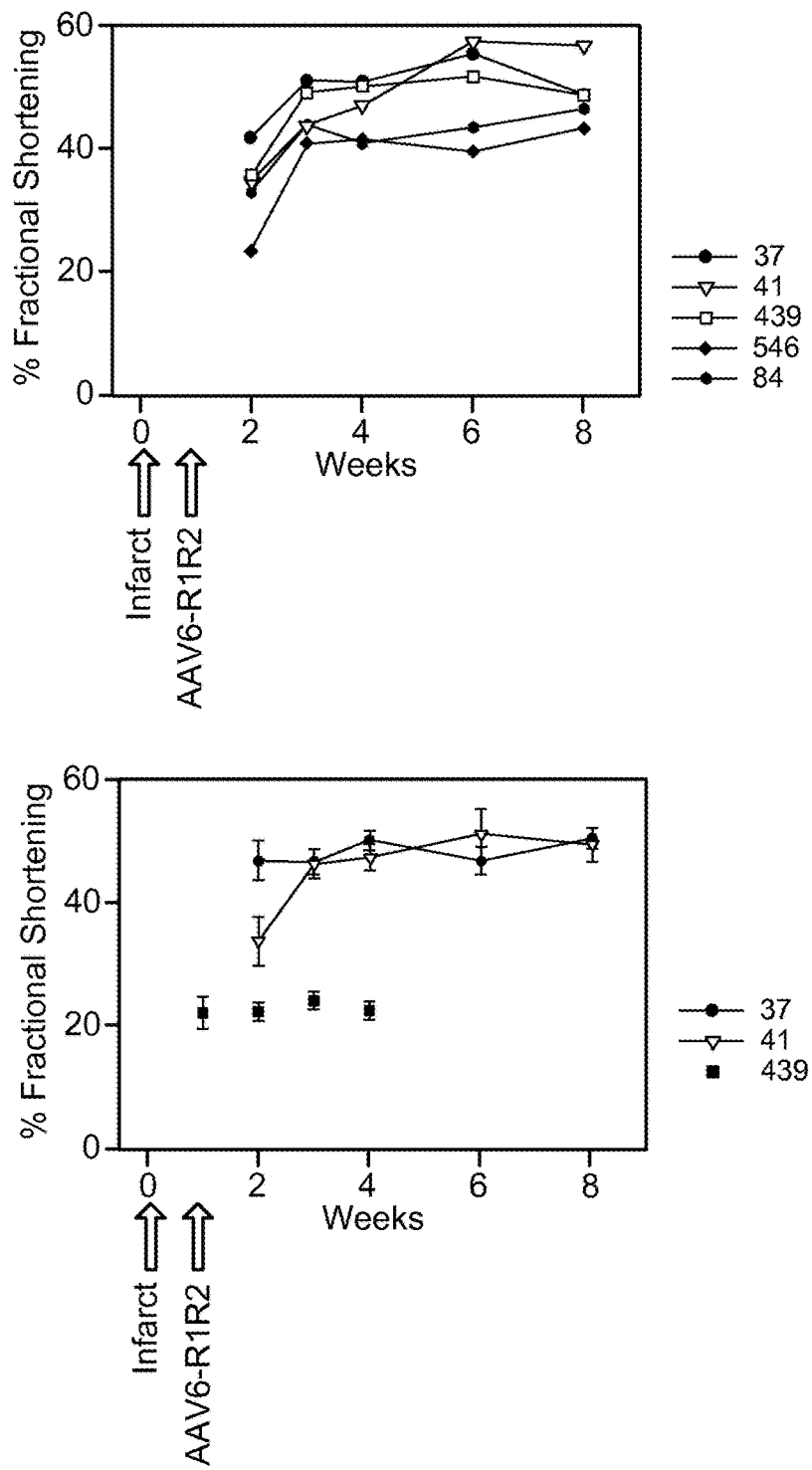

FIG. 38 shows the change in fractional shortening in rats given direct cardiac injections of AAV6-R1R2 on the fifth day post-infarct as measured by echocardiography in comparison with untreated infarct rats and untreated sham-operated rats.

Figure 39:
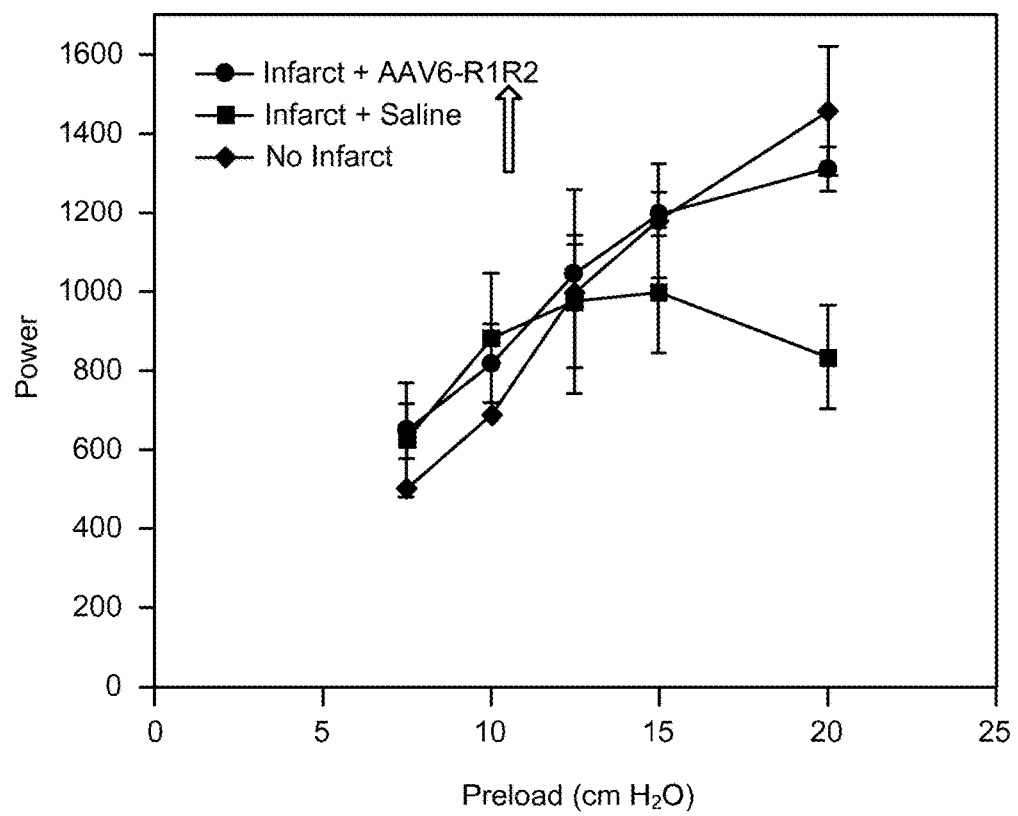

FIG. 39 shows the in vitro Neely working heart measurements of the rat hearts assessed in FIG. 38. Power on the y-axis is given in units of g·cm/min. A loss of pre-load responsiveness of hearts (heart failure) that have been infarcted (no treatment) and a recovery of pre-load responsiveness of the infarcted hearts receiving the vectors to the level of control, uninfarcted hearts were observed, thereby demonstrating a restoration of cardiac function.

FIG. 40 provides a nucleic acid sequence for the cTnT455 cardiac-specific promoter used in exemplary embodiments of the present invention.

DETAILED DESCRIPTION OF THE INVENTION

I. Introduction

Many current pharmaceutical therapies for heart failure target intracellular [Ca$^{2+}$]([Ca$^{2+}$]$_i$) metabolism, which can have significant side-effects such as arrhythmogenesis, or adverse affects on diastolic function. In one aspect, the present invention provides a method for directly targeted cardiac thin filaments to enhance intact cardiomyocyte contraction independent of [Ca$^{2+}$]$_i$. Specifically, it is shown herein that cardiac thin filament activation was enhanced through adenovirally-mediated over-expression of a cardiac troponin C (cTnC) variant designed to have increased Ca$^{2+}$ binding affinity, conferred by single amino acid substitution (L48Q). In skinned cardiac trabeculae and myofibrils we and others have shown that substitution of L48Q cTnC for native cTnC increases Ca$^{2+}$ sensitivity of force and the maximal rate of force development. Thus, in one embodiment, a method for enhancing intact cardiomyocyte contraction is provided by directly targeting cardiac thin filaments.

In one aspect, the present invention provides a novel therapeutic approach that combines cell- and gene therapy and is intended to improve cardiac performance, for example, in heart failure patients. Short of whole-organ transplantation, existing therapies for heart failure are aimed at either attenuating adverse ventricular remodeling or enhancing the force generation of remaining cardiomyocytes, usually via the pharmacological manipulation of intracellular calcium signaling. The former approach is typically only helpful to patients early in the disease process, while the latter approach is complicated by off-target effects (e.g., increased arrhythmias). In recent years, there has been considerable interest in cell transplantation as an alternative means of achieving cardiac repair, but such efforts to-date have been limited by the low cardiac potential of the cells employed and/or the relatively small amount of the graft myocardium formed. Cardiomyocytes from pluripotent human embryonic stem cells (ESCs) or the related induced pluripotent stem cells (iPSCs) have shown considerable promise in preclinical studies, and they form implants of human myocardium that are at least partially integrated with host muscle. However, here again, the grafts formed are generally quite small and unlikely to contribute enough force generating units to significantly improve cardiac output.

In one embodiment, the present invention provides a novel approach to heart failure that may overcome many of these shortcomings. As shown herein, elevated cytosolic levels of 2 deoxy-ATP (dATP) increase crossbridge binding and cyclic kinetics, resulting in greatly increased contractile properties without perturbations in intracellular calcium. dATP concentration can be increased in failing cardiomyocytes by the forced overexpression of ribonucleotide reductase (RR), the rate-limiting enzyme in its production, using gene therapy approaches. As demonstrated herein, transfection limited to a small area of the left ventricular (LV) wall (by direct viral vector injection) results in a substantial increase in LV function.

In another embodiment, because dATP readily passes through gap junctions and only low concentrations are required for enhanced force (≤1% of the cellular adenine nucleotide pool), the present invention provides a method for delivering dATP to failing myocardium by transplanting a second cell type that has been genetically modified to overexpress RR and is capable of forming gap junction connections with the target host myocardium. Because of their amenability to such genetic modification, tremendous capacity for expansion, and ability to form stable intracardiac implants that express the appropriate connexin isoforms, cardiomyocytes derived from human ESCs or iPSCs represent an ideal dATP donor. For example, in one embodiment, skin fibroblasts are obtained from a heart failure patient, reprogramed into iPSCs, and then modified by inserting a construct in which a cardiac-specific promoter drives expression of RR. In one embodiment, this method uses zinc finger nuclease-mediated transgenesis (which allows targeting of a well-characterized, "safe-harbor" locus in the genome) to insert the construct. After screening and expansion of the appropriately targeted iPSC clones, these cells are differentiated into cardiomyocytes and then implanted (e.g., by use a catheter) into the failing heart. Advantageously, this strategy does not require the formation of a large cardiac graft, nor does the graft need to be implanted within the hostile environment of an infarct scar. Instead, because the purpose of the graft is to deliver dATP, and not to produce force, a modest graft implanted in the well-vascularized distant myocardium might suffice. This is just one of many potential approaches and in no way limits the scope of the present invention. For example, in certain embodiments, other donor cell types (e.g., mesenchymal stem cells) may be used in the methods provided herein. Similarly, in certain embodiments, other methods of transgenesis (e.g., transposon, plasmid, or viral delivery) may be used.

In another aspect, the present invention provides adenoviral vectors expressing cytomegalovirus (CMV) promoter driven Rrm1 or Rrm2. In one embodiment, the vectors further encode for green fluorescent protein (GFP) as a transduction reporter. Cultured adult rat cardiomyocytes were transduced with these vectors, and the rate and extent of myocyte contraction and relaxation and Ca2+ transient rise and decay (Fura2 fluorescence) were monitored by video microscopy following a 48 hour viral incubation period. It is shown herein that these treatments significantly increased cellular [dATP], rate and extent of shortening, and rate of relaxation, with minimal effects on Ca2+ transients, at 0.5 Hz, 1 Hz and 2 Hz stimulation. Accordingly, in one embodiment, the present invention provides a method for enhancing cardiac contractility without impairing diastolic function by altering the cardiac intracellular RR and/or dATP pool, which can significantly alter the actin-myosin crossbridge cycle.

In another aspect, the present invention provides the first use of nucleotide manipulation to improve in vivo contractility. The use of dATP as a contractile substrate was first studied by Dr. Regnier over 15 years ago as a method for investigating myofilament chemo-mechanical transduction. However, application of dATP to improve cardiomyocyte function has the potential to open up many new avenues of research including, but not limited to, the effects on Ca2+ handling, metabolic pathways, and heart disease amelioration. Also provided is a targeted delivery method that is minimally invasive and can be expanded to larger animal models and humans.

Initial studies on the effect of dATP were performed on demembranated skeletal muscle, which resulted in a significant increase in Ca2+ sensitivity, but no change in maximal Ca2+ activated force. Subsequent studies in cardiac muscle were more dramatic, where dATP not only increased Ca2+ sensitivity of force, but also increased the magnitude of maximal Ca2+ activated force by ~40%. These results suggested that regulation of cardiac muscle contraction is more susceptible to alterations in acto-myosin activity, providing a cardiac specific differential benefit for myofilament targeted approaches. As such, we sought to up-regulate dATP production in cardiomyocytes. The challenge for intact cell and in situ studies was to increase intracellular [dATP] enough to produce increased contraction. This challenge was overcome by over-expressing a naturally occurring enzyme (Ribonucleotide Reductase; R1R2) that converts ADP to dADP, which is then rapidly phosphorylated by phosphocreatine kinase to dATP. Schoffstall et al. (2006) reported that as little as 10% [dATP](90% [ATP]) increased contraction of demembranated cardiac tissue and isolated contractile proteins[23]*, suggesting modest levels of dATP could increase contraction in intact cardiomyocytes. Unexpectedly, it is shown herein that significantly less dATP is required for functional potentiation in cardiomyocytes and the heart.

II. Experimental Findings

A. Expression of L48Q cTnC Enhances Cardiac Contractility

Using video-microscopy to monitor cell length (CL) and $Ca^{2+}$ (Fura2 transients), expression of L48Q cTnC (identified by co-expression with GFP) significantly increased the rate and extent of shortening (by 33% and 48%, respectively) without altering the $Ca^{2+}$ transient as compared to non-transduced adult rat cardiomyocytes. These differences were even more dramatic when compared to WT cTnC transduced cardiomyocytes. Importantly, the rate of relaxation was unaffected by the presence of L48Q cTnC, compared to all other groups. Expression and incorporation of L48Q cTnC into thin filaments was confirmed by western blot analysis of myofibrils from transduced cardiomyocytes, which indicated stoichiometric replacement of ~58% of native cTnC with L48Q cTnC.

These experiments demonstrate the feasibility of directly targeting cardiac thin filament proteins to enhance cardiac contractility without altering impairing relaxation.

One objective of this study was to determine if L48Q cTnC could be expressed in intact cardiomyocytes and incorporated into myofilaments to increase contractility without adversely affecting cardiomyocyte relaxation or Ca2+ transient properties. As shown in Examples 1 to 6, overexpression L48Q cTnC resulted in replacement of 58±7% of native cTnC with L48Q cTnC, and this dramatically increased the extent and rate of myocyte shortening and rate of myocyte relaxation, while having no apparent effect Ca2+ transient properties. We observed a low of 42% and a high of 70% replacement, but observed no significant differences in function between these levels of incorporation.

Previous experiments using skinned cardiac trabeculae showed that passive exchange of native cTnC with L48Q cTnC increased the magnitude and rate of force development and shortening at all levels of $Ca^{2+}$ activation, excluding saturating $[Ca^{2+}]$ (pCa 4.0), but these studies were performed with 100% replacement native cTnC in muscle preparations. In the current study using intact cardiomyocytes we did not expect expression of L48Q cTnC to result in 100% replacement of native cTnC. However, we did anticipate needing to increase L48Q cTnC levels to approach replacement of ~15-25% native cTnC to see a gain of function, as this was the proportion of TnC (M80Q sTnCF27W) we previously determined to be necessary to see a significant increase in $Ca^{2+}$ sensitivity of force in rabbit psoas muscle fibers[16]. The fact that we greatly exceeded this minima was unexpected and is intriguing in that it suggests the amount of virus needed to obtain significantly increased function may be less than what was applied in this study. It seems likely that less robust gene transfer using different viral constructs such as lentivirus or AAV6, or lower multiplicities of infection, could still achieve significant functional improvements. It would be advantageous to avoid the potential for negative side effects such as tissue inflammation. Future studies should focus on the minimal amount of L48Q cTnC required to produce significant functional improvement, and what is the viral particle load required to meet this minima. Additionally, other cTnC mutants have been shown to alter $Ca^{2+}$ binding affinity and increase $Ca^{2+}$ sensitivity of force and the rate of force development at submaximal $[Ca^{2+}]$[17], and thus may also have therapeutic potential for a variety of pathological conditions.

The potential for L48Q cTnC as a therapeutic tool are encouraging in that there was no significant effect on $Ca^{2+}$ transient behavior (or autorythmicity), especially considering other studies have shown that myofilament $Ca^{2+}$ sensitization through protein[18] or pharmacological[19,20] means have resulted in altered action potential behavior and increased risk of arrythmogenesis. This was unexpected in light of small differences (significant at 1 Hz) in minimal and maximal $Ca^{2+}$ in WT cTnC+GFP transduced cardiomyocytes. Whether this effect as due to WT cTnC or GFP was not specifically tested in this study, but results from separate studies have shown that GFP-only transfection of adult rat cardiomyocytes significantly increases minimal and maximal $Ca^{2+}$, especially at higher stimulation frequencies[21]. Thus, this effect may primarily be due to GFP, which is partially abrogated by overexpression of cTnC. In either case, expression of L48Q cTnC resulted in minimal and maximal $[Ca^{2+}]$ that were no different from non-transduced cardiomyocytes. Therefore, the effect of L48Q cTnC expression may be underestimated. If so, L48Q cTnC expression in the absence of GFP would tend to 1) lower minimal $[Ca^{2+}]$, leading to enhanced relaxation, and 2) lower maximal $[Ca^{2+}]$. This would increase the measure of contractile efficiency by shortening more for a given amount of $Ca^{2+}$ release. Interestingly, Lim et al., showed that adult rat cardiomyocytes overexpressing mutant TnC (E59D, D75Y) associated with idiopathic dilated cardiomyopathy markedly decreased contractility while having no affect on intracellular $Ca^{2+}$ homeostasis[22], demonstrating it is possible to manipulate thin filament Ca2+ binding affinity without affecting $Ca^{2+}$ transient behavior.

An apparent advantage of the use of the L48Q cTnC variant is that, while contraction was improved, myocyte relaxation was unaffected and was even enhanced at higher stimulation frequencies. It has been shown that increased $Ca^{2+}$ binding affinity could lead to prolonged thin-filament activation and thus prolonged crossbridge attachment, which hindered relaxation[23]. Prolonging systole and slowing diastolic relaxation would have severe in vivo functional consequences, reducing diastolic filling and, subsequently, cardiac output. For example, we reported that the rate of cardiac myofibril relaxation was slightly increased following ~100% exchange of L48Q cTnC (compared to WT cTnC exchange). This was due to a slightly prolonged duration of the slow phase thought to depend on crossbridge detachment[9]. However, these studies were done under isometric conditions, while intact myocytes in this study were allowed to shorten freely. Under these conditions, relaxation rate is also influenced by the restoring force supplied by titin, which increases in a linear manner as sarcomeres shorten[24]. Relaxation rates observed in the present study do roughly correlate with cellular fractional shortening. This would also seem to indicate that L48Q cTnC is not prolonging crossbridge attachment, as relaxation rates with L48Q cTnC were faster as would be expected with increased shortening. It is also possible that the 42-70% replacement of endogenous cTnC with L48Q cTnC was sufficient to improved shortening without affecting relaxation, while greater replacement may begin to adversely affect relaxation. Additionally, any effect of L48Q cTnC on relaxation may be reduced or eliminated at submaximal $[Ca^{2+}]$ levels that occur in intact myocardium, and effects may also differ under loaded conditions (strain) such as those encountered in vivo.

In conclusion, these experiments demonstrate the potential of directly targeting cardiac thin filament proteins to enhance cardiac contractility without altering diastolic function or $Ca^{2+}$ transient behavior. In one aspect, the strategy outlined above may be used to treat cardiomyocytes from functionally deficient or diseased myocardium.

B. Expression of Exogenous RR Complex Enhances Cardiac Contractility

It is shown herein that mouse tail vein or direct cardiac injections of an adenovirus vector (AV-R1R2) over-expressing R1 and R2 increased [dATP] significantly increases (40-50%) left ventricular (LV) fractional shortening and ejection fraction (FIG. 27) within 3-4 days. Interestingly, echocardiography of 8 month old transgenic mice that over-express R1R2 demonstrated similar LV functional potentiation compared to WT littermates (FIG. 27), with no apparent cardiac pathology, suggesting tolerance of this approach. This potentiation was further supported by preliminary hemodynamic (Millar) and Langendorff perfused heart experiments. Importantly, preliminary NMR measurements suggest increased performance does not come at the expense of energetic reserves, even with high [Ca2+] or Dobutamine challenge. Finally, dATP did not alter contraction of mouse aortic smooth muscle (compared with ATP; (FIG. 30) suggesting alterations of vascular tone are not likely to underlie any potential changes in hemodynamic parameters.

Cell length and ratiometric (fura2) Ca2+ fluorescence were monitored by video microscopy. At 0.5 Hz stimulation, the extent of shortening was increased ~40% and maximal rate of shortening was increased ~80% in cardiomyocytes over-expressing Rrm1+Rrm2 as compared to non-treated cardiomyocytes. The maximal rate of relaxation was also increased ~150% with Rrm1+Rrm2 (+GFP) overexpression, resulting in decreased time to 50% relaxation over non-treated cardiomyocytes. These differences were even more dramatic when compared to GFP-only transduced cardiomyocytes. Interestingly, Rrm1+Rrm2 overexpression had no effect on minimal or maximal intracellular [Ca2+] (Fura2 fluorescence), indicating increased contractility is primarily due to increased myofilament activity without altering Ca2+ release from the sarcoplasmic reticulum. Additionally, functional potentiation was maintained with Rrm1+Rrm2 overexpression as stimulation frequency was increased (1 Hz and 2 Hz). HPLC analysis indicated that cellular [dATP] was increased by approximately 10-fold following transfection, becoming slightly greater than 1% of the adenine nucleotide pool.

These experiments demonstrate the feasibility of directly targeting the actin-myosin crossbridge to enhance cardiac contractility and relaxation without affecting minimal or maximal $Ca^{2+}$.

One objective of this study was to determine if overexpression of ribonucleotide reductase (Rrm1+Rrm2) increases cellular [dATP] and, in turn, increases contractility in intact cardiomyocytes without adversely affecting cardiomyocyte relaxation. Overexpression of Rrm1+Rrm2 resulted in increased cellular [dATP] to ~1.0-1.5% of the total adenine nucleotide pool, and this dramatically increased the extent and rate of myocyte shortening and rate of myocyte relaxation, while having no apparent effect $Ca^{2+}$ transient properties.

Previous experiments using skinned cardiac trabeculae showed dATP increased isometric force and the rate of force development and shortening at all levels of $Ca^{2+}$ activation, including saturating $[Ca^{2+}]$(pCa 4.0), but these studies were performed with 100% replacement of 5 mM ATP with 5 mM dATP in bathing solutions[7,8,20]. For the current study in intact cardiomyocytes, over-expression of Rrm1+Rrm2 was not expected to result in high (mM) levels of dATP. However, we did anticipate needing to increase dATP levels to approach ~10% of the [ATP] to see a gain of function, as this was the proportion of dATP to ATP needed to see a functional difference in demembranated myocardium[21]. In fact, previous experiments on chick embryonic cardiomyocytes suggested replacement of ~1/3 of ATP with dATP may be required to achieve significant contractile enhancement[22]. Surprisingly, the observed large increases in contractility occurred with a relatively small increase in cardiomyocyte [dATP]. This suggests the amount of virus needed to obtain significantly increased function may be less than what was applied in this study. An advantage of this is that overexpressing less Rrm1+Rrm2 may reduce the potential for negative side effects[22,23]. It is possible there was a small population of contaminating cells (e.g., fibroblasts) that were either not as easily transfected or overexpressed less Rrm1+Rrm2, which would lead to underestimation of cardiomyocyte [dATP] from the HPLC analysis. However, considering the relative scarcity of non-cardiomyocyte cells in the culture, this confounding effect should be minimal.

Without being bound by theory, it is interesting to speculate on how the relatively small amount of total dATP can have such a dramatic effect on cardiomyocyte function. Contractile efficiency estimations (FIG. 9) indicates that increased contractility in Rrm1+Rrm2 transduced myocytes is primarily myofilament based, thus dATP likely has its effect primarily by improving crossbridge cycling. This is similar to experiments where faster (alpha) myosin has been expressed in cardiomyocytes that normally express slower (beta) myosin, resulting in functional potentiation with no effect on $Ca^{2+}$ transient amplitude. The mechanism behind increased myofilament activity with increased [dATP] that occurred in this study is perplexing, as concentrations were still only ~1% compared to ATP.

In studies with skeletal myosin, we have shown that the γ-phosphate cleavage equilibrium by myosin is similar for ATP and dATP, but post-hydrolysis crossbride binding and the rate of crossbridge detachment is increased with dATP[24]. This can explain an increase in the $Ca^{2+}$ sensitivity of tension development, and a faster rate of tension development and shortening velocity in skinned skeletal muscle[24-26]. While we have not performed a detailed chemo-mechanical analysis with dATP in cardiac muscle, we have shown that it increases maximal crossbridge binding (as indicated from stiffness measurements) and isometric force by ≥40%, in addition to increasing $k_{tr}$ and unloaded shortening velocity[20]. We have also shown that dATP significantly isometric force and $k_{tr}$ in cardiac muscle at all levels of $Ca^{2+}$, whether the demembranated cardiac muscle was expressing primarily α- or β-myosin heavy chain[8]. This is important because, unlike skeletal muscle, the intracellular [$Ca^{2+}$] during a cardiac muscle twitch only reaches a level that is approximately within the half-maximally activating range. For the current experiments with cultured cardiomyocytes, it may be that a small increase binding of myosin S1 heads containing dADP.Pi was enough to cooperatively increase thin filament activation, resulting in the increased the magnitude and rate of shortening.

Figure 6:
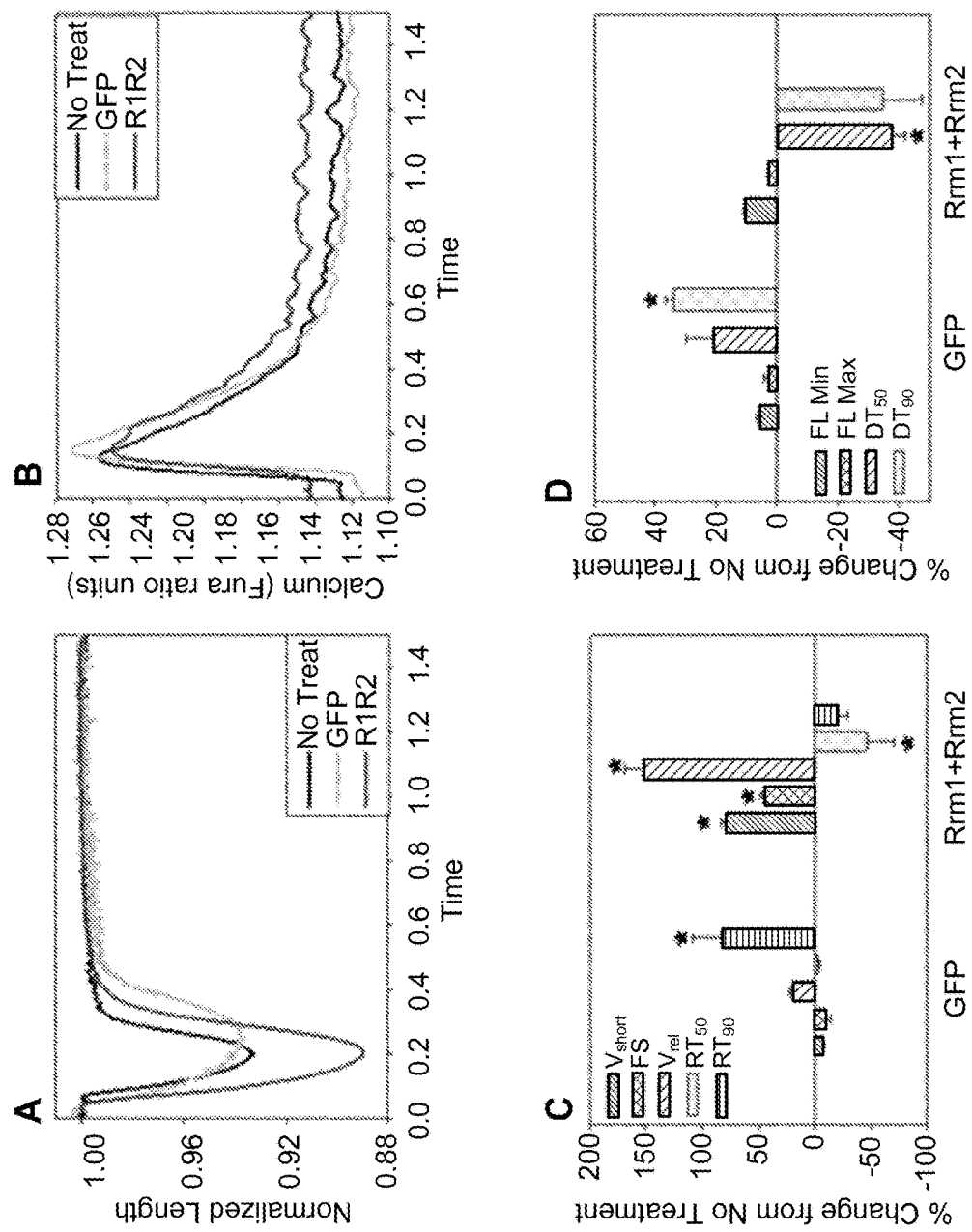
FIG. 6. Representative cell length traces (a) and $Ca^{2+}$ transients (b, Fura-2 fluorescence) of non-treated (black), GFP-only (green), and Rrm1+Rrm2+GFP (red) transduced cardiomyocytes. Percentage change in contractile (c) and $Ca^{2+}$ transient (d) properties of GFP-only and Rrm1+Rrm2+

There was no adverse affect on relaxation with overexpression of Rrm1+Rrm2 (and the subsequent increase in [dATP]), in fact myocyte relaxation was enhanced. It is possible that this resulted, at least in part, from a faster decay of the $Ca^{2+}$ transient. dATP could be used by other ATPases (besides myosin) such as the sarcoplasmic $Ca^{2+}$ ATPase (SERCA), the plasma membrane $Ca^{2+}$ ATPase (PMCA), and the sodium/calcium exchanger (NCX). An increase in SERCA activity could explain the increased decay rate of the $Ca^{2+}$ transient, especially at 0.5 and 1.0 Hz stimulation. However, increased SERCA activity is known to increase SR $Ca^{2+}$ stores[27], making more $Ca^{2+}$ available for release during activation, which was not observed in Rrm1+Rrm2 transduced cardiomyocytes (FIG. 6d). Furthermore, increased PMCA and NCX activity should result in a $Ca^{2+}$ transient decay over time by extruding $Ca^{2+}$ out of the cell. Because ~95% of activating $Ca^{2+}$ is released from the SR in rat cardiomyocytes[28,29], $Ca^{2+}$ extrusion from the cell would lead to progressively decreased $Ca^{2+}$ transient amplitudes and contraction, which was not observed over the duration of these experiments. However, the specific mechanism behind increased $Ca^{2+}$ transient decay rate warrants future investigation.

Since dATP increases the rate of crossbridge detachment[20,25] this may also explain a faster rate of relaxation in the current experiments with cultured cardiomyocytes. Although specific mechanisms that govern relaxation in intact cardiac muscle are not known, early phase relaxation in cardiac and skeletal myofibrils has been shown to be governed by the rate of crossbridge dissociation[30-33]. This would also be consistent with the present finding that cardiomyocyte contractility was increased with Rrm1+Rrm2, because shortening rate in unloaded cells (as in culture) is primarily determined by crossbridge detachment rates[34,35]. It is also possible that increased crossbridge detachment rate with dATP accelerates cooperative thin filament inactivation, by more rapidly decreasing the bound crossbridge population as thin filament $Ca^{2+}$ binding decreases during relaxation.

Accordingly, in one aspect the present invention provides methods wherein dATP may provide the dual benefit of positive inotropy and lusitropy, with little alteration of $Ca^{2+}$ transient properties, thus providing potential as an alternative to current pharmaceutical therapeutic approaches.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims. In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

III. Abbreviations cTnC cardiac troponin C
cTnT cardiac troponin T
$k_{off}$ rate of calcium dissociation
NRC neonatal rat cardiomyocyte
ARC adult rat cardiomyocyte
GFP green fluorescent protein
$RT_{50}$, $RT_{90}$ time to 50% and 90% relaxation
$DT_{50}$, $DT_{90}$ time to 50% and 90% $Ca^{2+}$ decay
WT wild-type
Rrm1 or R1 muscle ribonucleotide reductase 1
Rrm2 or R1 muscle ribonucleotide reductase 2

IV. Definitions

"Cardiac function," in the context of the present invention, refers to the function of the heart as reflected by one or more measurable parameters, e.g. myocardial contractility, change in fractional shortening, maximal rate of shortening, myocardial relaxation, maximal rate of myocardial relaxation, relaxation time, effects on $Ca^{2+}$ transients, heart rate, end-systolic pressure, end diastolic pressure, end-systolic volume, end-diastolic volume, cardiac output, stroke work, stroke volume, cardiac index, etc. Said parameters may be determined by hemodynamic and/or echocardiographic measurements and/or any other methods known to those of skill in the art. Whether an improvement in cardiac function has taken place is determined on an individual basis. For instance, for an individual in need of a positive inotropic effect, an improvement in myocardial contractility signifies an increase in myocardial contractility. Alternatively, for an individual in need of a positive lusitropic effect, an improvement in myocardial relaxation signifies an increase in myocardial relaxation, e.g. as reflected by increased rate of relaxation.

"Myocardial contractility," used interchangeably herein with the term "inotropy," refers to the strength of a ventricular contraction during which blood is ejected from the heart. Improvement of myocardial contractility is determined on an individual basis using one or more measurable inotropy parameters. For an individual or patient in need of a positive inotropic effect, an improvement in myocardial contractility entails an increase in myocardial contractility as measured using echocardiography. For an individual or patient in need of a negative inotropic effect, an improvement in myocardial contractility entails a decrease in myocardial contractility. Examples of measurable inotropy parameters include OP/Ot, percent thickening, percent shortening, fractional shortening, and ejection fraction "Myocardial relaxation," used interchangeably herein with the term "lusitropy," refers to the ability of the heart to relax following excitation contraction coupling. Improvement of myocardial relaxation is determined on an individual basis using one or more measurable lusitropy parameters. For an individual or patient is in need of a positive lusitropic effect, an improvement in myocardial relaxation entails an increase in the rate of relaxation. For an individual or patient is need of a negative lusitropic effect, an improvement in myocardial contractility entails a decrease in the rate of relaxation. Examples of measurable lusitropy parameters include a rate of pressure decline (−dP/dtmin) during diastole as determined from pressure sensor measurements, a rate of force/strain decline (−dF/dt) as determined from force sensor measurements, and isovolumic relaxation time (IVRT) as determined from cardiac impedance measurements or from detected heart sounds. For instance, the measuring device may be programmed to compare the lusitropy parameter to a specified threshold in order to determine if diastolic relaxation is impaired and operate the neural stimulation circuitry to deliver sympathetic stimulation to the heart in response to thereto.

"Grafting" as used herein refers to the placement of cells into a subject. Cells can be autogeneic (i.e., from the subject to be treated), isogeneic (i.e., a genetically identical but different subject, e.g., from an identical twin), allogeneic (i.e., from a non-genetically identical member of the same species) and/or xenogeneic (i.e., from a member of a different species). Cells may be obtained from a donor (either living or cadaveric) or derived from an established cell line. To obtain cells from a donor (e.g., a potential recipient of a bioscaffold graft), standard biopsy techniques known in the art may be employed. Representative techniques are described, for example, in U.S. Pat. No. 6,536,567.

The terms "therapy," "treatment," and "amelioration" refer to any reduction in the severity of symptoms or amount of amyloid aggregation, or improvement in cognitive function. As used herein, the terms "treat" and "prevent" are not intended to be absolute terms. Treatment can refer to any delay in onset, amelioration of symptoms, improvement in patient survival, increase in survival time or rate, etc. The effect of treatment can be compared to an individual or pool of individuals not receiving the treatment.

By "cardiomyocyte" is meant a cardiac contractile cell, which is a cardiac muscle cell. The cardiomyocyte cell may be isolated and cultured in vitro or be part of the myocardium of a host.

The term "embryonic stem cells" (ES cells) refers to cells derived from the inner cell mass of blastocysts or morulae that have been serially passaged as cell lines. The ES cells may be derived from fertilization of an egg cell with sperm or DNA, nuclear transfer, parthenogenesis, or by means to generate hES cells with homozygosity in the MHC region. The term "human embryonic stem cells" (hES cells) refers to cells derived from the inner cell mass of human blastocysts or morulae that have been serially passaged as cell lines. The hES cells may be derived from fertilization of an egg cell with sperm or DNA, nuclear transfer, parthenogenesis, or by means to generate hES cells with homozygosity in the HLA region.

The term "induced pluripotent stem cells" or "iPSCs, as used herein, refers to a pluripotent stem cell derived from a postnatal somatic cell by any combination of forced expression of reprogramming factors alone or in combination with one or more reprogramming agents.

The term "mesenchymal stem cell," as used herein, refers to a cell capable of giving rise to differentiated cells in multiple mesenchymal lineages, specifically to osteoblasts, adipocytes, myoblasts and chondroblasts. Generally, mesenchymal stem cells also have one or more of the following properties: an ability to undergo asynchronous, or symmetric replication, that is where the two daughter cells after division can have different phenotypes; extensive self-renewal capacity; and clonal regeneration of the tissue in which they exist, for example, the non-hematopoietic cells of bone marrow.

The terms "patient", "host" and "individual" are used interchangeably herein to refer to any mammalian subject for whom diagnosis or therapy is desired, e.g. primate species, such as humans and chimpanzees; cattle, dogs, cats, guinea pigs, rabbits, rats, mice, horses, and so on. In preferred embodiments, the species is human. Of particular interest are subjects having a myocardial associated disorder that is amenable to treatment (e.g., to mitigate symptoms associated with the disorder) by the grafting of cells, e.g. cardiomyocytes, fibroblasts, etc.) which express both subunits of a ribonucleotide reductase (i.e., R1, R2) into the subject. In many embodiments, the hosts are humans.

"Donor cells," in the context of the present invention, refer to cells derived from a mammalian origin, e.g. primate species, such as humans and chimpanzees; cattle, dogs, cats, guinea pigs, rabbits, rats, mice, horses, etc., which have the capacity to form or establish gap junctions with cardiomyocytes of a host when grafted to the host myocardium. Examples of donor cells include, without limitation, fibroblasts and cardiomyocytes. The donor cells can be autogeneic (i.e., from the host to be treated), isogeneic (i.e., a genetically identical but different subject, e.g., from an identical twin), allogeneic (i.e., from a non-genetically identical member of the same species) and/or xenogeneic (i.e., from a member of a different species). Cells may be obtained from a donor (either living or cadaveric) or derived from an established cell line. To obtain cells from a donor, standard biopsy techniques known in the art may be employed.

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art. In some embodiments, the expression vector is a viral vector, e.g. an adeno-associated viral vector.

The term "adeno-associated viral vector," as used herein, encompasses both wild-type and recombinant adeno-associated viral vectors, which are nonpathogenic, nonenveloped, DNA virus containing a linear single-stranded genome of about 4.6-4.8 kb that requires coinfection with a helper virus for viral replication. Examples of adeno-associated viral vectors useful in the present invention include, without limitation, an AAV6, AAV2, rAAV2/1, rAAV2/2, rAAV2/3, rAAV2/4, rAAV2/5, rAAV2/6, rAAV2/7 rAAV2/8, rAAV2/9, rAAV2/10, rAAVM41, dsAAV, etc. Adeno-associated viral vectors and their use in gene transfer applications are reviewed in: Pacak et al. (2011) Molecular Therapy 19(9): 1582-1590; Hansruedi Biieler, Biol. Chem. (June 1999) 380:612 622; Robbins et al., TIBTECH (January 1998) 16:35 40; and Patjin & Kay, Semin. Liver. Dis. (1999) 19: 61 69. Other references of interest include: Burton, et al., Proc Natl Acad Sci USA (1999) 96: 12725 12730; Fan, et al., Hum. Gene Ther. (1998) 9: 2527 2535; Miao et al., Nat. Genet. (May 1998) 19: 13 15; Nakai et al., J. Virol. (July 1999) 73: 5438 5447; and Rendahl, et al., Nat Biotechnol (1998) 16, 757 761; Gregorevic et al. (2004) Systemic delivery of genes to striated muscles using adeno-associated viral vectors. Nature Med 10:828-834; Blankinship et al. (2004) Efficient transduction of skeletal muscle using vectors based on adeno-associated virus serotype 6. Mol Ther 10:671-678; Blankinship et al (2006) Gene therapy strategies for Duchenne muscular dystrophy utilizing recombinant adeno-associated virus vectors. Mol Ther 13:241-249. and Salva et al. (2007) Design of tissue-specific regulatory cassettes for high-level rAAV-mediated expression in skeletal and cardiac muscle. Mol Ther 15:320-329.

As an illustration, gene therapy vectors based on AAV6 can be generated by cloning a DNA expression cassette (e.g. a promoter/enhancer regulating gene expression linked to a complementary DNA (cDNA) sequence encoding a therapeutic protein or RNA, followed by a transcription terminating signal such as a poly-adenylation sequence; in some cases, the cDNA and promoter are separated by an intron) in between two copies of an adeno-associated virus (AAV) inverted terminal repeat (ITR). This ITR-Expression cassette-ITR genome is referred to as a recombinant AAV (rAAV) genome. The AAV ITR sequences provide a packaging signal for encapsidation into a recombinant AAV particle. The ITR also provides an origin of replication for producing multiple copies of the recombinant AAV genome. DNA containing this recombinant genome can then be co-transfected into a packaging cell line expressing various adenoviral helper proteins (commonly HEK293 cells) along with plasmid(s) containing the Rep/Cap genes from a wild-type AAV genome as well as additional adenoviral helper functions. AAV does not replicate autonomously, but rather requires the co-infection of a second virus, such as adenovirus, to supply critical helper functions in trans. The AAV ITRs can be derived from a number of different serotypes of wild type AAVs. For example, commonly used ITRs are from AAV serotype 2. When generating recombinant AAV6 vectors (rAAV6), the Cap gene from AAV serotype 6 is used in the co-transfection step. Thus, the "AAV6" is a recombinant adeno-associated viral vector carrying AAV2 ITRs flanking an expression cassette, and encapsidated by the AAV6 capsid proteins.

By "promoter" is meant a minimal sequence sufficient to direct transcription in a recombinant cell. "Promoter" is also meant to encompass those elements sufficient for promoter-dependent gene expression controllable for cell-type specific, tissue-specific or inducible by external signals or agents; such elements may be located in the 5' or 3' regions of the native gene (e.g., enhancer elements). Examples of promoters include, without limitation, the CK7 promoter, and CMV promoter.

A "cardiac-specific promoter," in the context of the present invention, refers to a wild-type or recombinant promoter that selectively drives expression of a gene under its control in cardiac cells. Examples of cardiac-specific promoters include the $\alpha$-MHCs$_{5.5}$ promoter, $\alpha$-MHC$_{86}$ promoter, human cardiac actin promoter, and the cTnT455 promoter described herein.

By "operably linked" or "operatively linked" is meant that a DNA sequence and a regulatory sequence(s) are connected in such a way as to permit expression when the appropriate molecules (e.g., transcriptional activator proteins) are bound to the regulatory sequence(s).

"Percent sequence identity," "percent amino acid sequence identity," "percent gene sequence identity," and/or "percent nucleic acid/polynucleotide sequence identity," with respect to two amino acids, polynucleotide and/or gene sequences (as appropriate), refer to the percentage of residues that are identical in the two sequences when the sequences are optimally aligned. Thus, 80% amino acid sequence identity means that 80% of the amino acids in two optimally aligned polypeptide sequences are identical.

By "transformation", "transduction" or "transfection" is meant a permanent or transient genetic change, preferably a permanent genetic change, induced in a cell following incorporation of new nucleic acid (e.g., DNA or RNA exogenous to the cell). Genetic change can be accomplished either by incorporation of the new nucleic acid into the genome of the host cell, or by transient or stable maintenance of the new DNA as an episomal element.

By "transformed cell", "transfected cell" or "transduced cell" is meant a cell into which (or into an ancestor of which) has been introduced, by means of recombinant DNA techniques, a DNA molecule encoding a protein of interest.

By "overexpressing" or "overexpression" of a gene product (such as a R1 or R2) is meant an increased level of protein expression over a normal level of protein expression for a particular cell or cell type at, for example, a particular developmental stage or stage of differentiation. In certain instances, overexpressing can be a cumulative effect of protein expression from endogenous and recombinant genes or essentially protein expression from a recombinant gene. Overexpression of R1 or R2 is meant to refer to the expression of the respective ribonucleotide reductase protein subunit within a particular cell which is above the expression level normally associated with a normal or wild-type cell at a particular stage of differentiation. In certain embodiments overexpression of a gene product is meant an increase in expression by a factor of at least about 2 fold, in other embodiments at least about 5 fold and yet in still other embodiments, at least about 10 fold.

By "construct" is meant a recombinant nucleic acid, generally recombinant DNA, that has been generated for the purpose of the expression of a specific nucleotide sequence(s), or is to be used in the construction of other recombinant nucleotide sequences.

As used herein, "polypeptide" refers to an amino acid sequence of a recombinant or non-recombinant polypeptide having an amino acid sequence of i) a native polypeptide, ii) a biologically active fragment of an polypeptide, iii) biologically active polypeptide analogs of an polypeptide, or iv) a biologically active variant of an polypeptide. Polypeptides useful in the invention can be obtained from any species, e.g., mammalian or non-mammalian (e.g., reptiles, amphibians, avian (e.g., chicken)), particularly mammalian, including human, rodenti (e.g., murine or rat), bovine, ovine, porcine, murine, or equine, preferably rat or human, from any source whether natural, synthetic, semi-synthetic or recombinant. For example, an "R1 polypeptide" refers to the amino acid sequences of isolated human R1 polypeptide obtained from a human, and is meant to include all naturally-occurring allelic variants, and is not meant to limit the amino acid sequence to the complete, native amino acid sequence associated with the recited protein molecule.

A "variant" of a polypeptide is defined as an amino acid sequence that is altered by one or more amino acids (e.g., by deletion, addition, insertion and/or substitution). Generally, "addition" refers to nucleotide or amino acid residues added to an end of the molecule, while "insertion" refers to nucleotide or amino acid residues between residues of a naturally-occurring molecule. The variant can have "conservative" changes, wherein a substituted amino acid has similar structural or chemical properties, e.g., replacement of leucine with isoleucine. More rarely, a variant can have "nonconservative" changes, e.g., replacement of a glycine with a tryptophan. Similar minor variations can also include amino acid deletions or insertions, or both. Guidance in determining which and how many amino acid residues may be substituted, added, inserted or deleted without abolishing biological or immunological activity can be found using computer programs well known in the art, for example, DNAStar software.

The term "targeting agent" refers to a compound that exhibits selectivity for a particular target organ, tissue, or cell-type. A targeting agent is capable of directing a composition, with which it is operatively associated, to a particular target organ or tissue. A targeting agent can be operatively associated with at least one cationic polymeric carrier and/or other agent.

The term "myocardial infarction," as used herein, means a process by which ischemic disease results in a region of the myocardium being replaced by scar tissue.

The term, "ischemic heart disease," as used herein, means any disorder resulting from an imbalance between the myocardial need for oxygen and the adequacy of the oxygen supply. Most cases of ischemic heart disease result from narrowing of the coronary arteries, as occurs in atherosclerosis or other vascular disorders.

The term "heart failure," as used herein, means impaired cardiac function that renders the heart unable to maintain the normal blood output at rest or with exercise, or to maintain a normal cardiac output in the setting of normal cardiac filling pressure. A left ventricular ejection fraction of about 40% or less is indicative of heart failure (by way of comparison, an ejection fraction of about 55% to 60% percent is normal). Patients with heart failure display well-known clinical symptoms and signs, such as tachypnea, pleural effusions, fatigue at rest or with exercise, contractile dysfunction, and edema. Relative severity and disease progression are assessed using well known methods, such as physical examination, echocardiography, radionuclide imaging, invasive hemodynamic monitoring, magnetic resonance angiography, and exercise treadmill testing coupled with oxygen uptake studies.

The term "cardiomyopathy," as used herein, refers to a cardiovascular disorder. In some embodiments, the cardiomyopathy is selected from a primary cardiopathology or a secondary cardiopathology. The cardiomyopathy may be selected from a genetic cardiopathology, a hypertrophic cardiomyopathy, an ischemic cardiomyopathy, a restrictive cardiomyopathy, and a dilated cardiomyopathy. In embodiments involving the improvement of cardiac function in an individual with hypertrophic cardiomyopathy, the cardiomyopathy may have resulted from: (a) post-myocardial infarction remodeling, (b) cardiac valve disease; (c) sustained cardiac afterload; (d) myocarditis; or (e) familial hypertrophic cardiomyopathy.

As used herein, the term "Cardiac Troponin C" or "cTnC" refers to a polypeptide of the troponin complex having multiple calcium-binding sites. In a preferred embodiment, cTnC refers to human cTnC (Entrez Ref: NP_003271), encoded by the TNNC1 gene (Entrez Ref: NM_003280.2), or conservative variants, splice variants, or tagged variants thereof.

As used herein, the term "Ribonucleotide Reductase Complex," "RR," or "RNR" refers to a heterodimeric tetrameric polypeptide complex containing the RNR1 (or "R1") and RNR2 (or "R2") subunits. In a preferred embodiment, the R1 subunit refers to the human ribonucleotide reductase M1 subunit (Entrez Ref: AAD37491.1), encoded by the RRM1 gene (Entrez Ref: AF107045.1) or conservative variants, splice variants, or tagged variants thereof. The R2 subunit may refer to either the ribonucleotide reductase M2 subunit or the ribonucleotide reductase M2 B subunit. In one preferred embodiment, R2 refers to the human ribonucleotide reductase M2 subunit (Entrez Ref: AAK51163), encoded by the RRM2 gene (Entrez Ref: AY032750.1). In other preferred embodiments, R2 refers to the human ribonucleotide reductase M2 B subunit isoform 1 (Entrez Ref: NP_056528.2), encoded by the RRM2B gene (Entrez Ref: NM_015713.4); the human ribonucleotide reductase M2 B subunit isoform 2 (Entrez Ref: NP_001165948.1), encoded by the RRM2B gene (Entrez Ref: NM_001172477); or the human ribonucleotide reductase M2 B subunit isoform 3 (Entrez Ref: NP001165949), encoded by the RRM2B gene (Entrez Ref: NM_001172478.1); or conservative variants, splice variants, or tagged variants thereof.

V. Embodiments

In one aspect, the present invention provides methods for treating cardiac function comprising the administration of engineered cTnC variants that have not been clinically identified as HCM/DCM mutations, but produce similar increases or decreases in $Ca^{2+}$ sensitivity of contraction.

In one aspect, the present invention provides a method for improving cardiac function in an individual in need thereof, comprising administering a vector encoding a cTnC variant having increased site II Ca2+ binding affinity to a cardiac tissue of the individual. In a specific embodiment, the cTnC variant comprises an L48Q amino acid substitution.

In a certain embodiment, the individual has a heart condition resulting in reduced contraction. In a specific embodiment, the individual has an infarcted heart.

In one aspect, the present invention provides a method for improving cardiac function in an individual in need thereof, comprising administering a vector encoding a cTnC variant having decreased site II Ca2+ binding affinity to a cardiac tissue of the individual. In one embodiment, the cTnC variant comprises an L57Q amino acid substitution. In another embodiment, the cTnC variant comprises an I61Q amino acid substitution.

In certain embodiments, it is provided a method to improve cardiac function in an individual having a genetic predisposition to heart disease. More specifically, the genetic predisposition is due to one or more genetic mutation(s) in a sarcomeric protein selected from beta-cardiac myosin heavy chain, cardiac actin, cardiac troponin T, alpha-tropomyosin, cardiac troponin I, cardiac myosin-binding protein C, and myosin light chain. In some embodiments, the genetic mutation(s) is associated with increased $Ca^{2+}$ sensitivity of myofibril contraction and/or hypertrophic cardiomyopathy phenotypes. Examples of such genetic mutations include, without limitation, mutations at residue 92 of cTnT, e.g. R92W, R92Q, and R92L cTnT, or mutations at MYH7, MYBPC3, TNNT2, TNNI3, TPM1, ACTC, MYL2, MYL3, or combinations thereof. The method of improving cardiac function in these individuals involves administering such individuals a viral vector comprising a nucleic acid sequence encoding a L57Q or I61Q cTnC variant, said nucleic acid sequence being operably linked to a cardiac-specific promoter. In other embodiments, the genetic mutation(s) is associated with decreased $Ca^{2+}$ sensitivity of myofibril contraction and/or dilated cardiomyopathy phenotypes. Examples of such genetic mutations include, without limitation, missense mutations Ser532Pro and Phe764Leu, deletion in cTnT (deltaLys210), or mutations in genes MYH7, MYBPC3, TNNT2, TNNI3, TPM1, ACTC, MYL2, MYL3, or combinations thereof. The method of improving cardiac function in such individuals involves administering said individuals having the Ca2+ desensitizing genetic mutation(s) a viral vector comprising a nucleic acid sequence encoding a L48Q cTnC variant, said nucleic acid sequence being operably linked to a cardiac-specific promoter.

In certain methods provided herein the vector is administered by lipofection, coating on a stent, or direct injection (i.e., via a catheter). In one embodiment, the vector comprises a transposon, a plasmid, or a viral vector. In one embodiment, the vector comprises an adenoviral vector harboring a nucleic acid encoding for the cTnC variant. In a specific embodiment, the nucleic acid encoding the cTnC variant further comprises a CMV promoter operably linked to the nucleotide sequence encoding the cTnC variant.

In a particular embodiment, the method of the invention employs a non-viral vector for effecting transfer of the cTnC gene to cells, e.g. by liposome fusion, calcium phosphate, microinjection, electroporation, polycations, particle bombardment, and receptor-mediated methods. In a certain embodiment, the vector comprises a nanoparticle associated with a nucleic acid encoding the cTnC variant. In a specific embodiment, the nanoparticle comprises a liposome encapsulating the nucleic acid encoding the cTnC variant. In some embodiments, the vector further encodes a targeting agent having affinity for a cardiac tissue-specific marker. In one embodiment, the targeting agent is selected from the group consisting of an antibody, an antibody fragment, and an aptamer.

In another aspect, the present invention provides a method for improving cardiac function in an individual in need thereof, comprising administering a vector encoding a ribonucleotide reductase (RR) complex to a cardiac tissue of the individual. In one embodiment, the individual has a heart condition resulting in reduced contraction. In a specific embodiment, the individual has an infarcted heart.

In certain methods provided herein the vector is administered by lipofection, coating on a stent, or direct injection (i.e., via a catheter). In one embodiment, the vector comprises a transposon, a plasmid, or a viral vector.

In a specific embodiment, the vector comprises a cell harboring a nucleic acid encoding R1 and R2 subunits of the RR complex. In one embodiment, the cell is a cardiomyocyte. In a specific embodiment, the cardiomyocyte is derived from a pluripotent embroynic step cell (ESC), an induced pluripotent stem cell (iPSC), or a mesenchymal stem cell. In one embodiment, the (iPSC) is derived from a cell harvested from the individual. In a specific embodiment, the cell harvested from the individual is a skin fibroblast. In certain embodiments of the methods provided herein, the nucleic acid encoding R1 and R2 subunits of the RR complex further comprises a cardiac-specific promoter operably linked to the nucleotide sequence encoding the R1 and/or R2 subunits.

In a particular embodiment, the vector comprises a nanoparticle associated with a nucleic acid encoding R1 and R2 subunits of the RR complex. In one embodiment, the vector further comprises a sequence encoding a targeting agent having affinity for a cardiac tissue-specific marker. In a specific embodiment, the targeting agent is selected from the group consisting of an antibody, an antibody fragment, and an aptamer. In a more specific embodiment, the nanoparticle comprises a liposome encapsulating the nucleic acid encoding the cTnC variant.

In another aspect, the present invention provides a method for improving cardiac function in an individual in need thereof, comprising administering: (i) a vector encoding a cTnC variant having increased site II Ca2+ binding affinity to a cardiac tissue of the individual; and (ii) a vector encoding a ribonucleotide reductase (RR) complex to a cardiac tissue of the individual.

In yet another aspect, the present invention provides a pharmaceutical composition for improving the cardiac function in an individual in need thereof, comprising a vector encoding a cTnC variant having increased site II Ca2+ binding affinity. In one embodiment, the cTnC variant comprises an L48Q amino acid substitution.

In yet another aspect, the present invention provides a pharmaceutical composition for improving the cardiac function in an individual in need thereof, comprising a vector encoding a cTnC variant having decreased site II Ca2+ binding affinity. In one embodiment, the cTnC variant comprises an L57Q and/or I61Q amino acid substitution.

In certain embodiments of the pharmaceutical compositions provided herein, the vector comprises an adenoviral vector harboring a nucleic acid encoding for the cTnC variant. In a specific embodiment, the nucleic acid encoding the cTnC variant further comprises a CMV promoter operably linked to the nucleotide sequence encoding the cTnC variant.

In one aspect, the present invention provides a pharmaceutical composition for improving the cardiac function in an individual in need thereof, comprising a vector encoding a ribonucleotide reductase (RR) complex. In one embodiment, the vector comprises a cell harboring a nucleic acid encoding R1 and R2 subunits of the RR complex.

In certain embodiments of the pharmaceutical compositions provided herein, the cell is a cardiomyocyte. In a specific embodiment, the cardiomyocyte is derived from a pluripotent embroynic stem cell (ESC), an induced pluripotent stem cell (iPSC), or a mesenchymal stem cell. In a more specific embodiment, the (iPSC) is derived from a cell harvested from the individual, for example, a skin fibroblast.

In certain embodiments of the pharmaceutical compositions provided herein, the nucleic acid encoding R1 and R2 subunits of the RR complex further comprises a cardiac-specific promoter operably linked to the nucleotide sequence encoding the R1 and/or R2 subunits.

In one aspect, the present invention provides a method for improving cardiac function in an individual in need thereof, comprising administering a vector encoding a cTnC variant having increased site II Ca2+ binding affinity to a cardiac tissue of the individual. In a particular embodiment, the cTnC variant comprises an L48Q amino acid substitution.

In certain embodiments of the methods provided above, the individual has a heart condition resulting in reduced contraction. In one embodiment, the individual has been diagnosed with ischemic heart disease, a cardiomyopathy, or a myocardial infarction. In one embodiment, the cardiomyopathy is a primary cardiomyopathy, a genetic cardiomyopathy, a dilated cardiomyopathy, or a hypertrophic cardiomyopathy. In one embodiment, the individual has been diagnosed with reduced systolic function.

In one aspect, the present invention provides a method for improving cardiac function in an individual in need thereof. More specifically, the individual has a Ca2+ sensitizing or hypertrophic cardiomyopathy phenotype due to one or more genetic mutation(s) in a sarcomeric protein selected from beta-cardiac myosin heavy chain, cardiac actin, cardiac troponin T, alpha-tropomyosin, cardiac troponin I, cardiac myosin-binding protein C, and myosin light chain. Examples of such genetic mutations include, without limitation, mutations at residue 92 of cTnT, e.g. R92W, R92Q, and R92L cTnT, or mutations at MYH7, MYBPC3, TNNT2, TNNI3, TPM1, ACTC, MYL2, MYL3, or combinations thereof. The method of improving cardiac function in such individuals involves administering said individuals having the Ca2+ sensitizing genetic mutation(s) a viral vector comprising a nucleic acid sequence encoding a L57Q or I61Q cTnC variant, said nucleic acid sequence being operably linked to a cardiac-specific promoter.

In another aspect, the present invention provides a method of improving cardiac function in an individual having a Ca2+ desensitizing or dilated cardiomyopathy phenotype associated with one or more genetic mutations in a sarcomeric protein selected from beta-cardiac myosin heavy chain, cardiac actin, cardiac troponin T, alpha-tropomyosin, cardiac troponin I, cardiac myosin-binding protein C, and myosin light chain. Examples of such genetic mutations include, without limitation, missense mutations Ser532Pro and Phe764Leu, deletion in cTnT (deltaLys210), or mutations in genes MYH7, MYBPC3, TNNT2, TNNI3, TPM1, ACTC, MYL2, MYL3, or combinations thereof. The method of improving cardiac function involves administering said individuals having the Ca2+ desensitizing genetic mutation(s) a viral vector comprising a nucleic acid sequence encoding a L48Q cTnC variant, said nucleic acid sequence being operably linked to a cardiac-specific promoter.

In certain embodiments of the methods provided above, the vector is administered by lipofection, coating on a stent, or direct injection (i.e., via a catheter). In one embodiment, the vector comprises a transposon, a plasmid, or a viral vector. In a specific embodiment, the vector comprises an adenoviral vector harboring a nucleic acid encoding for the cTnC variant. In one embodiment, the nucleic acid encoding the cTnC variant further comprises a CMV promoter, a CK7 promoter, a α-MHC$_{5.5}$ promoter, a α-MHC$_{86}$ promoter, a cardiac actin promoter, a cTnT455 promoter, or other cardiac-specific promoter operably linked to the nucleotide sequence encoding the cTnC variant. In one embodiment, the vector comprises a nanoparticle associated with a nucleic acid encoding the cTnC variant. In one embodiment, the vector further encodes a targeting agent having affinity for a cardiac tissue-specific marker. In one embodiment, the targeting agent is selected from the group consisting of an antibody, an antibody fragment, and an aptamer. In one embodiment, the nanoparticle comprises a liposome encapsulating the nucleic acid encoding the cTnC variant.

In one aspect, the present invention provides a method for improving cardiac function in an individual in need thereof, comprising administering a vector encoding a ribonucleotide reductase (RR) complex to a cardiac tissue of the individual.

In certain embodiments of the methods provided above, the individual has a heart condition resulting in reduced contraction. In one embodiment, the individual has an infarcted heart.

In certain embodiments of the methods provided above, the vector is administered by lipofection, coating on a stent, or direct injection (i.e., via a catheter). In one embodiment, the vector comprises a transposon, a plasmid, or a viral vector. In one embodiment, the vector comprises a cell harboring a nucleic acid encoding R1 and R2 subunits of the RR complex. In one embodiment, the cell is a cardiomyocyte. In one embodiment, the cardiomyocyte is derived from a pluripotent embroynic step cell (ESC), an induced pluripotent stem cell (iPSC), or a mesenchymal stem cell. In one embodiment, the (iPSC) is derived from a cell harvested from the individual. In one embodiment, the cell harvested from the individual is a skin fibroblast.

In certain embodiments of the methods provided above, the nucleic acid encoding R1 and R2 subunits of the RR complex further comprises a cardiac-specific promoter operably linked to the nucleotide sequence encoding the R1 and/or R2 subunits.

In certain embodiments of the methods provided above, the vector comprises a nanoparticle associated with a nucleic acid encoding R1 and R2 subunits of the RR complex. In one embodiment, the vector further encodes a targeting agent having affinity for a cardiac tissue-specific marker. In one embodiment, the targeting agent is selected from the group consisting of an antibody, an antibody fragment, and an aptamer. In one embodiment, the nanoparticle comprises a liposome encapsulating the nucleic acid encoding the cTnC variant.

In one aspect, the present invention provides a method for improving cardiac function in an individual in need thereof, comprising administering: (i) a vector encoding a cTnC variant having increased site II Ca2+ binding affinity to a cardiac tissue of the individual; and (ii) a vector encoding a ribonucleotide reductase (RR) complex to a cardiac tissue of the individual.

In one aspect, the present invention provides a pharmaceutical composition for improving the cardiac function in an individual in need thereof, comprising a vector encoding a cTnC variant having increased site II Ca2+ binding affinity. In one embodiment, the cTnC variant comprises an L48Q amino acid substitution.

In one aspect, the present invention provides a pharmaceutical composition for improving the cardiac function in an individual in need thereof, comprising a vector encoding a cTnC variant having decreased site II Ca2+ binding affinity. In one embodiment, the cTnC variant comprises an L57Q and/or I61Q amino acid substitution.

In certain embodiments of the compositions provided above, the vector comprises an adenoviral vector harboring a nucleic acid encoding for the cTnC variant. In one embodiment, the nucleic acid encoding the cTnC variant further comprises a CMV promoter operably linked to the nucleotide sequence encoding the cTnC variant.

In one aspect, the present invention provides a pharmaceutical composition for improving the cardiac function in an individual in need thereof, comprising a vector encoding a ribonucleotide reductase (RR) complex. In one embodiment, the vector comprises a cell harboring a nucleic acid encoding R1 and R2 subunits of the RR complex. In one embodiment, the cell is a cardiomyocyte. In one embodiment, the cardiomyocyte is derived from a pluripotent embroynic step cell (ESC), an induced pluripotent stem cell (iPSC), or a mesenchymal stem cell. In one embodiment, the (iPSC) is derived from a cell harvested from the individual. In one embodiment, the cell harvested from the individual is a skin fibroblast. In one embodiment, the nucleic acid encoding R1 and R2 subunits of the RR complex further comprises a cardiac-specific promoter operably linked to the nucleotide sequence encoding the R1 and/or R2 subunits.

VI. Examples

Example 1

Adult and Neonatal Cell Isolation and Culture. These studies were approved by the University of Washington (UW) Animal Care Committee and conducted in accordance with federal guidelines. Animals were cared for in accordance with US NIH Policy on Humane Care and Use of Laboratory Animals in the Department of Comparative Medicine at UW. Adult rat (Fischer 344) cardiomyocytes (ARCs) were isolated from heart using aortic retrograde perfusion for enzymatic (collagenase/protease) dispersion of cells[10]. Neonatal Rat Cardiomyocytes (NRCs) were isolated by enzymatic dispersion from 1-3-day old newborn Fischer 344 rats as previously described[11].

Example 2

Plasmid design and virus production. We produced HEK293 generated adenoviral vectors expressing histidine-tagged (N-terminal 6-His) L48Q cTnC or WT cTnC from the CMV promoter. Both vectors contained a second expression cassette for green fluorescent protein (GFP) as a transduction reporter protein, and we also expressed a vector for GFP-only. Virus was introduced to cardiomyocytes at ~250 particles per cell.

Recombinant adenovirus containing appropriate cDNA constructs driven by the CMV promoter was used to induce overexpression of L48Q and WT cTnC in transfected cultured adult and neonatal rat cardiomyocytes. A second expression cassette for green fluorescent protein (GFP) was contained in each adenovirus as a reporter protein for successful transduction. Cardiomyocytes were infected with adenovirus containing genes for [L48Q cTnC+GFP] or [WT cTnC+GFP] for 2 days. We achieved nearly 100% transfection efficiency and gene transfer as grossly indicated by green fluorescence with microscopy. This is consistent with previous studies using cardiomyocytes[13]. Cell survival over this period was similar for all groups, including non-transduced control cells, suggesting these viral vectors did not compromise cardiomyocyte viability. Cardiomyocyte numbers and sarcomere lengths are summarized in Table 1. There was no difference in resting sarcomere length between groups, indicating that overexpression of L48Q or WT cTnC expression (+GFP) did not increase calcium independent activation.

TABLE 1

Cell characteristics

| | n | SL (μm) | Cell length (μm) |
|---|---|---|---|
| Non-transduced | 54 | 1.89 ± 0.03 | 85.5 ± 2.4 |
| Control (WT cTnC) | 73 | 1.82 ± 0.02 | 89.8 ± 2.3 |
| L48Q cTnC | 60 | 1.84 ± 0.02 | 91.9 ± 2.9 |

Example 3

Contractile Assessments. In modified Tyrodes buffer at ambient temperature, cell shortening and relaxation of arbitrarily selected stimulated cardiomyocytes was recorded using IonOptix system video microscopy. (IonOptix, Milton, Mass., USA). Calcium transients induced by electrical stimulation were measured in Fura2 loaded cells using IonOptix equipment as described[12]. Fura2 fluorescence was measured using an IonOptix spectrophotometer (Stepper Switch) attached to a fluorescence microscope. Emitted Fura2 fluorescence was collected by the 40× objective, passed through a 510 nm filter and detected by a photomultiplier tube.

Figure 1:
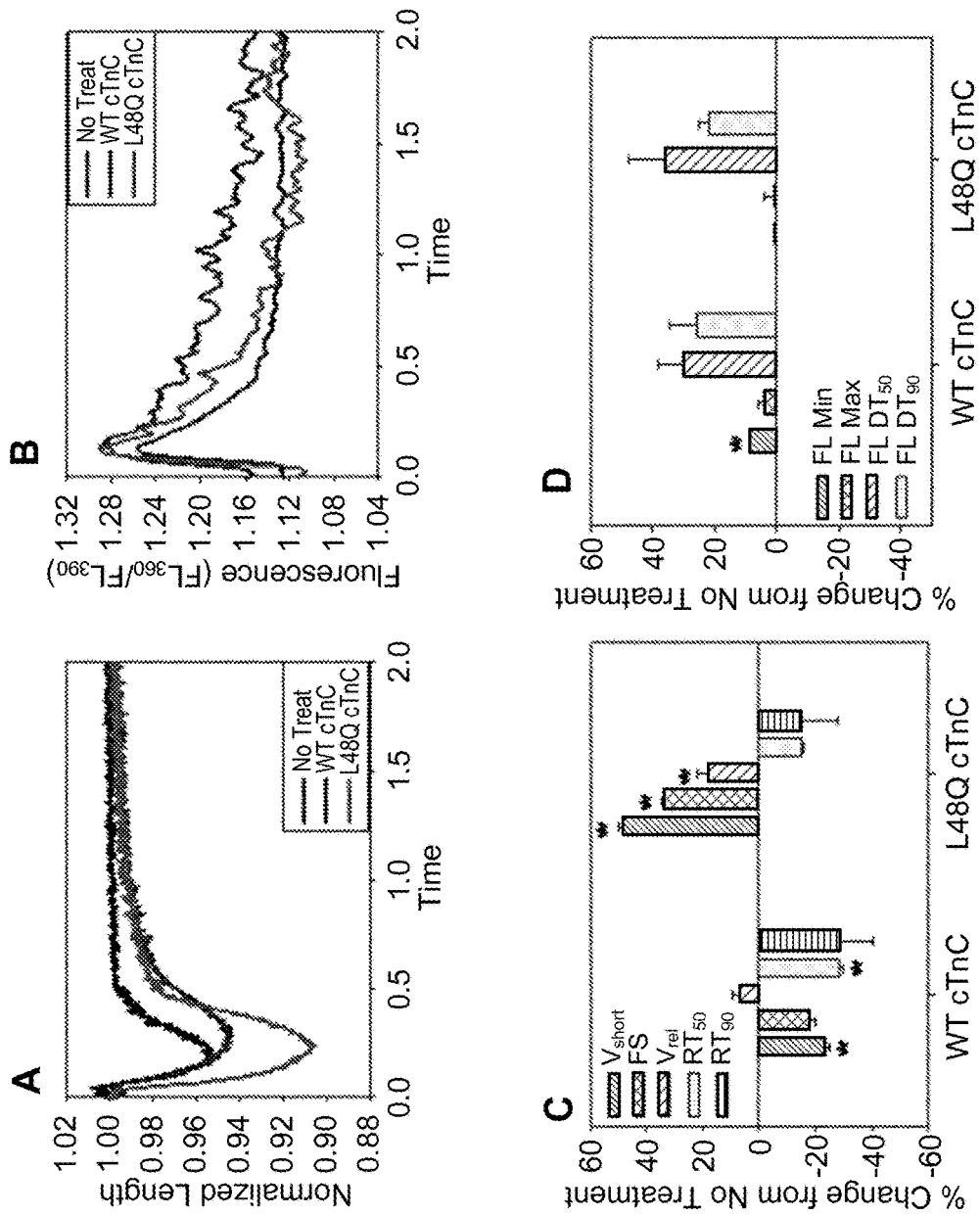
FIG. 1. Representative cell length traces (A) and $Ca^{2+}$ transients (B, Fura-2 fluorescence) of non-treated (black), WT cTnC+GFP (blue), and L48Q cTnC+GFP (red) transduced cardiomyocytes. Percentage change in contractile (C) and $Ca^{2+}$ transient (D) properties of WT cTnC+GFP and L48Q cTnC+GFP transduced myocytes, stimulated at 0.5 Hz, as compared to non-treated myocytes. $V_{short}$=velocity of shortening; FS=fractional shortening; $V_{rel}$=maximal relaxation velocity; $RT_{50,90}$=time to 50% and 90% relaxation, respectively; FL=fluorescence; $DT_{50,90}$=time to 50% and 90% Ca2+ decay, respectively *$p<0.05$ as compared to No Treatment, †=$p<0.05$ as compared to WT cTnC.

The effects of L48Q cTnC expression on extent and rate of stimulated shortening-relengthening and $Ca^{2+}$ release-reuptake of adult rat cardiomyocytes was determined using video length-detection and fluorescence photometry, respectively (IonOptix). FIG. 1A shows representative shortening traces, and FIG. 1B shows representative $Ca^{2+}$ transients (Fura2 fluorescence), for non-treated (black), WT cTnC+GFP (blue), and L48Q cTnC+GFP (red) transduced cardiomyocytes. The data for all measurements at 0.5 Hz stimulation are summarized in Table 2. WT cTnC+GFP overexpression significantly slowed the rate of contraction, but did not have a significant effect on fractional shortening (FS) as compared to non-treated cardiomyocytes. Whether this slowing is due to GFP or overexpression of cTnC was not assessed, although GFP has been reported to have a deleterious effect[14] or no effect[12,15] on contractility of GFP. In either case, expression of L48Q was more than able to overcome potential inhibition with significantly increased rate and extent of shortening as compared to WT cTnC transduced and non-transduced cardiomyocytes. There was no difference in maximal relaxation rate or the times to 50% and 90% relaxation between groups at 0.5 Hz stimulation frequency. The $Ca^{2+}$ transient was also little affected by WT or cTnC overexpression, except that WT cTnC transduced cardiomyocytes had a slight, non-significant (p=0.55) elevation in minimal $Ca^{2+}$. This had no effect on resting SL or maximal $Ca^{2+}$ release. FIG. 1C illustrates the % differences in rate and extent of shortening, relaxation rate, and time to 50% and 90% relaxation and FIG. 1D illustrates the % difference in $Ca^{2+}$ transient properties, including minimal and maximal $Ca^{2+}$, and the time to 50% and 90% $Ca^{2+}$ decay. There was no significant effect from either WT cTnC+GFP or L48Q cTnC+GFP on maximal $Ca^{2+}$, indicating that enhanced contractility with L48Q cTnC was primarily due to increased myofilament responsiveness to activating $Ca^{2+}$.

TABLE 2

Contractile and $Ca^{2+}$ transient values for 0.5 Hz stimulation.

| | Fractional Shortening (%) | Maximal Shortening Rate (μm/s) | Maximal Relaxation Rate (μm/s) | $RT_{50}$ (ms) | $RT_{90}$ (ms) | Minimal $Ca^{2+}$ (Fura ratio units) | Maximal $Ca^{2+}$ (Fura ratio units) | $DT_{50}$ (ms) | $DT_{90}$ (ms) |
|---|---|---|---|---|---|---|---|---|---|
| Non-transduced | 6.6 ± 0.4 | 77.7 ± 4.4 | 65.6 ± 5.7 | 105 ± 13 | 287 ± 30 | 1.1 ± 0.02 | 1.23 ± 0.02 | 171 ± 19 | 534 ± 54 |
| Control (WT cTnC) | 5.4 ± 0.4 | 59.4 ± 4.2* | 61.2 ± 7.1 | 135 ± 15 | 369 ± 42 | 1.19 ± 0.03 | 1.28 ± 0.03 | 222 ± 21 | 669 ± 65 |
| L48Q cTnC | 8.9 ± 0.5*† | 115.1 ± 7.0*† | 77.1 ± 8.9 | 121 ± 12 | 330 ± 36 | 1.11 ± 0.02 | 1.24 ± 0.03 | 232 ± 15 | 650 ± 47 |

\* = p < 0.05 as compared to No Treat,
† = p < 0.05 as compared to WT cTnC,
‡ = p < 0.05 as compared to 0.5 Hz for all groups.

Example 4

Figure 2:
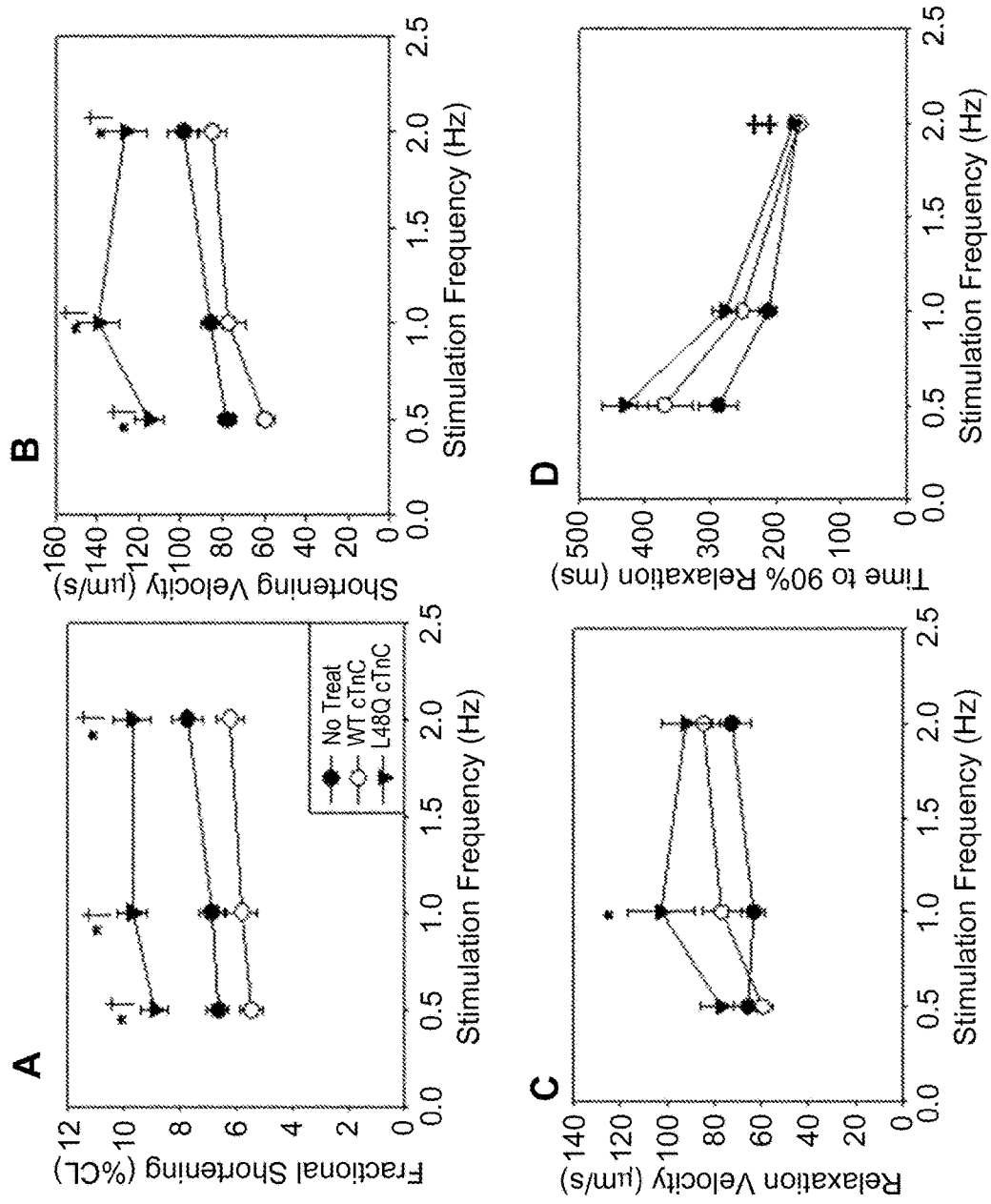
FIG. 2. Effect of stimulation frequency on contractile properties. L48Q cTnC transduced myocytes (closed triangles) respond similarly to stimulation frequency as WT cTnC transduced (open circles) and non-treated myocytes (closed circles) but show elevated fractional shortening (A) and shortening velocity (B) at all frequencies. Relaxation velocity (C) and time to 90% relaxation (D) are also similar between groups, with time to relaxation shortening as stimulation frequency increases. *=$p<0.05$ as compared to No Treat, †=$p<0.05$ as compared to WT cTnC, ‡=$p<0.05$ as compared to 0.5 Hz for all groups FIG. 3. Effect of stimulation frequency on $Ca^{2+}$ handling properties. L48Q cTnC transduced myocytes (closed triangles) respond similarly to stimulation frequency as WT cTnC transduced (open circles) and non-treated myocytes (closed circles) in minimal (A) and maximal (B) fluorescence. As with cardiomyocyte relaxation, $Ca^{2+}$ transient decay time to 50% (C) and 90% (D) is shortened with increased stimulation frequency. *=$p<0.05$ as compared to No Treat, †=$p<0.05$ as compared to WT cTnC, ‡=$p<0.05$ as compared to 0.5 Hz for all groups.
Figure 3:
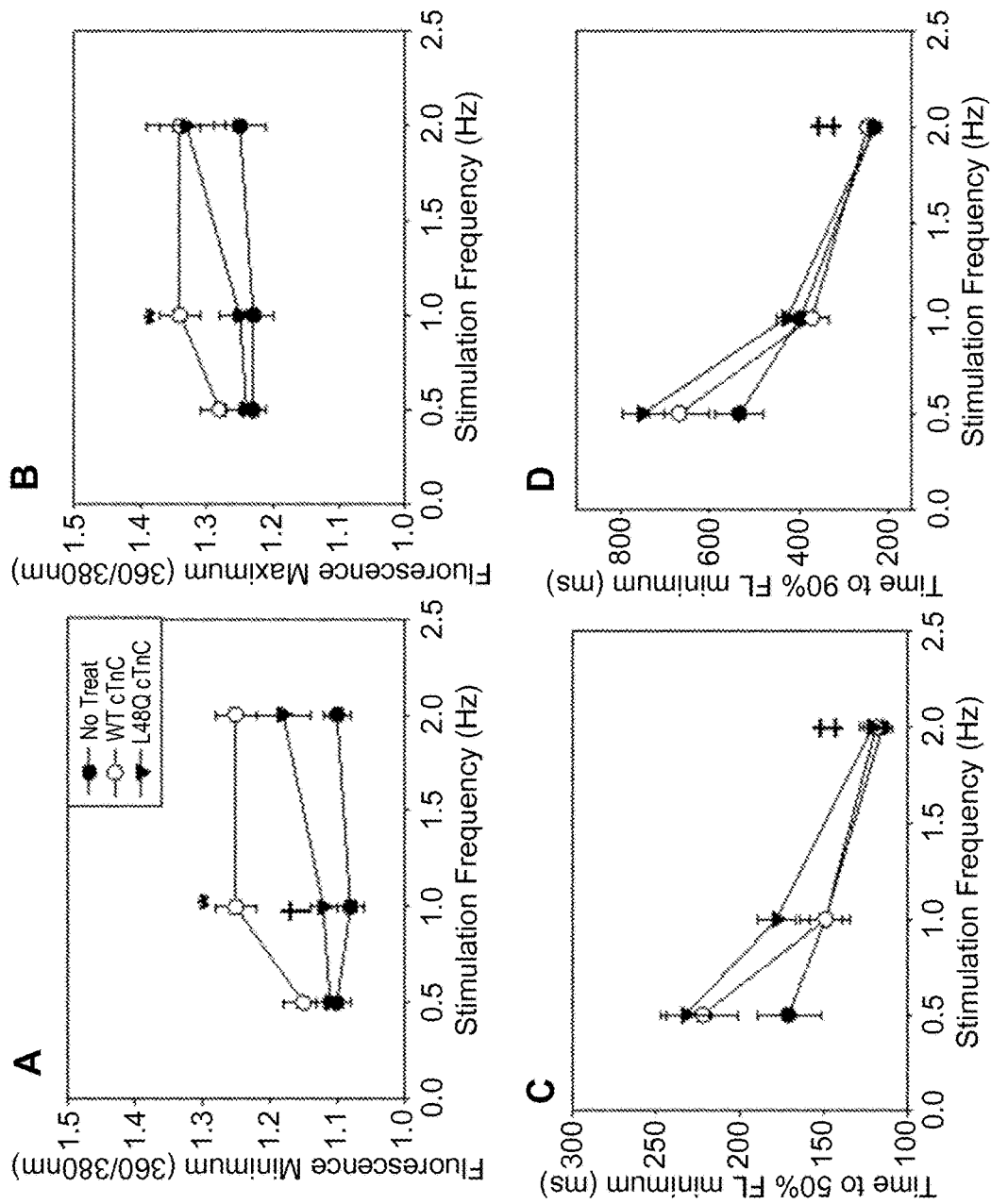

Because changes in heart rate are a normal physiological adaptation to systemic demand, it is important to determine whether L48Q cTnC overexpression affects normal cellular response to increased stimulation frequency. FIG. 2 summarizes the effect of increased stimulation frequency (0.5 to 1 to 2 Hz) on fractional shortening (2A), shortening velocity (2B), relaxation velocity (2C), and time to 90% relaxation (2D). The contractile response to stimulation frequency was similar between groups, and L48Q cTnC transduced cardiomyocytes maintained functional potentiation at all frequencies. Importantly, increased pacing frequency is associated with a positive lusitropic effect, shortening the time to 90% relaxation in all groups. There was little difference in non-transduced myocytes vs. WT cTnC transduced myocytes, but relaxation velocity was actually increased in L48Q cTnC myocytes at 1 Hz and 2 Hz stimulation. The effect of stimulation frequency on $Ca^{2+}$ transients was also assessed, and is summarized in FIG. 3 for minimal $Ca^{2+}$ (3A), maximal $Ca^{2+}$ (3B) and time to 50% (3C) and 90% (3D) $Ca^{2+}$ decay. As with contraction, there was no difference in $Ca^{2+}$ transient behavior with increased stimulation frequency between non-transduced and L48Q cTnC transduced myocytes. WT cTnC transduced cardiomyocytes had a slight increase in minimal and maximal $Ca^{2+}$ at 1 Hz, as compared to non-transduced and L48Q cTnC transduced myocytes, but the times to 50% and 90% relaxation were similar between groups at all stimulation frequencies.

Figure 4:
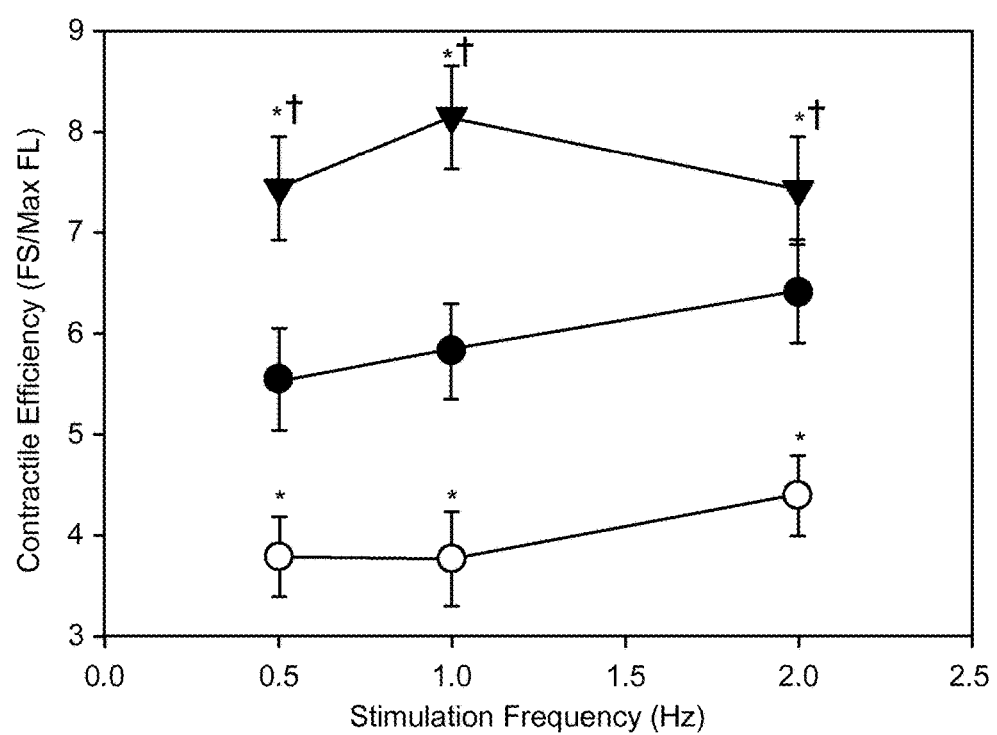
FIG. 4. Contractile efficiency as assessed as fractional shortening divided by maximal fura fluorescence (peak $Ca^{2+}$) indicates L48Q cTnC transduced cardiomyocytes (closed triangles) are significantly more sensitive to $Ca^{2+}$ at all stimulation frequencies, while WT cTnC transduced cardiomyocytes (open circles) are less responsive to $Ca^{2+}$ as compared to non-treated cardiomyocytes (closed circles). *=$p<0.05$ as compared to No Treat, †=$p<0.05$ as compared to WT cTnC.

Since there was little difference between groups in minimal and maximal $Ca^{2+}$, changes in contractility can best be explained by a change in myofilament responsiveness to activating $Ca^{2+}$. This is illustrated in FIG. 4 as contractile efficiency, defined here as cardiomyocyte fractional shortening divided by maximal fura2 fluorescence (peak $Ca^{2+}$). Cardiomyocytes expressing L48Q cTnC had significantly higher contractile efficiency than non-transduced or GFP transduced cardiomyocytes at all stimulation frequencies. Interestingly, there was a significant difference in contractile efficiency at all frequencies between WT cTnC and non-transduced myocytes, which may indicate that L48Q cTnC-induced contractile potentiation is underestimated. Results for 1 Hz and 2 Hz stimulation are summarized in Table 3 and Table 4, respectively.

TABLE 3

Contractile and $Ca^{2+}$ transient values for 1 Hz stimulation.

| | Fractional Shortening (%) | Maximal Shortening Rate (μm/s) | Maximal Relaxation Rate (μm/s) | $RT_{50}$ (ms) | $RT_{90}$ (ms) | Minimal $Ca^{2+}$ (Fura ratio units) | Maximal $Ca^{2+}$ (Fura ratio units) | $DT_{50}$ (ms) | $DT_{90}$ (ms) |
|---|---|---|---|---|---|---|---|---|---|
| Non-transduced | 6.9 ± 0.4 | 85.1 ± 5.2 | 63.2 ± 4.8 | 97 ± 7 | 211 ± 13 | 1.08 ± 0.02 | 1.23 ± 0.03 | 149 ± 10 | 398 ± 24 |
| Control (WT cTnC) | 5.8 ± 0.6 | 76.9 ± 8.3 | 63.8 ± 8.9 | 108 ± 13 | 251 ± 26 | 1.26 ± 0.03* | 1.34 ± 0.03* | 149 ± 15 | 373 ± 38 |
| L48Q cTnC | 9.7 ± 0.5*† | 139.4 ± 10.3*† | 102.5 ± 14.7*† | 124 ± 9 | 276 ± 19 | 1.12 ± 0.02 | 1.25 ± 0.03 | 178 ± 11 | 428 ± 24 |

\* = p < 0.05 as compared to No Treat,
† = p < 0.05 as compared to WT cTnC.

TABLE 4

Contractile and $Ca^{2+}$ transient values for 2 Hz stimulation.

| | Fractional Shortening (%) | Maximal Shortening Rate (μm/s) | Maximal Relaxation Rate (μm/s) | $RT_{50}$ (ms) | $RT_{90}$ (ms) | Minimal $Ca^{2+}$ (Fura ratio units) | Maximal $Ca^{2+}$ (Fura ratio units) | $DT_{50}$ (ms) | $DT_{90}$ (ms) |
|---|---|---|---|---|---|---|---|---|---|
| Non-transduced | 7.7 ± 0.6 | 98.4 ± 7.7 | 72.5 ± 8.0 | 84 ± 4 | 165 ± 7 | 1.10 ± 0.02 | 1.25 ± 0.04 | 115 ± 6 | 234 ± 11 |
| Control (WT cTnC) | 6.2 ± 0.5 | 84.6 ± 7.0 | 63.0 ± 7.0 | 85 ± 6 | 164 ± 10 | 1.26* ± 0.03 | 1.34 ± 0.03* | 119 ± 7 | 248 ± 14 |
| L48Q cTnC | 9.7 ± 0.6*† | 126.4 ± 10.4*† | 92.1 ± 10.3*† | 92 ± 6 | 172 ± 9 | 1.18 ± 0.04 | 1.33 ± 0.06 | 121 ± 8 | 233 ± 14 |

\* = p < 0.05 as compared to No Treat,
† = p < 0.05 as compared to WT cTnC.

Example 5

Figure 5:
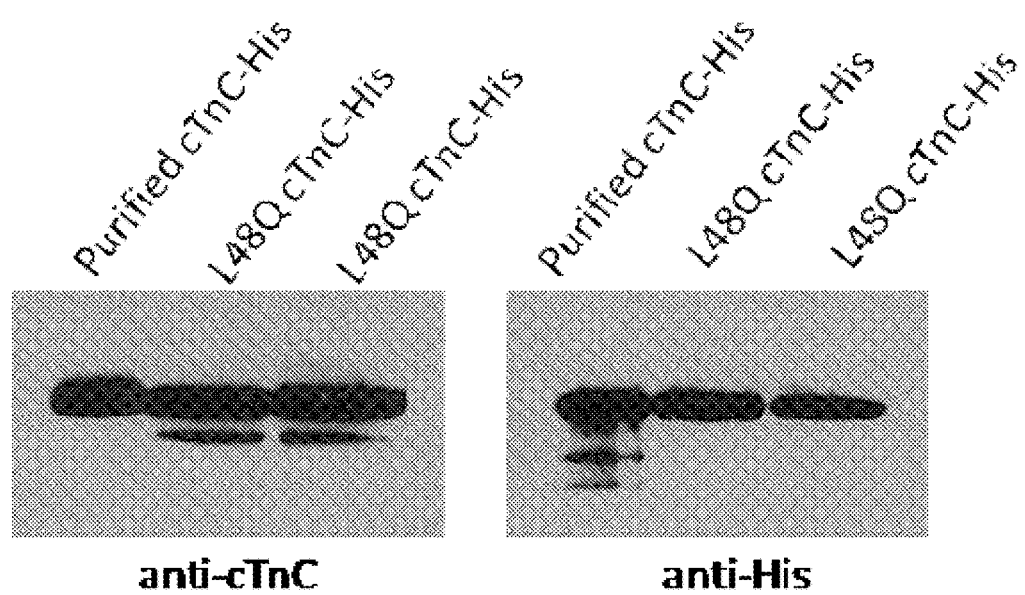
FIG. 5. Western blots of WT and L48Q cTnC-His transduced neonatal cardiomyocytes probed with anti-cTnC (A) show total cTnC myofilament content, while those probed with anti-His (B) show L48Q cTnC incorporation into thin filaments. Densitometry indicated L48Q cTnC replaced 58±7% of native cTnC.

To determine the level of L48Q cTnC incorporation into myofilaments cultured neonatal cardiomyocytes were infected with adenoviral constructs containing genes for [L48Q cTnC+GFP] or [WT cTnC+GFP] 48 hours, or left untreated. As with adult cardiomyocytes, cell survival over this period was qualitatively similar for all groups, suggesting viral vectors did not compromise in vitro cardiomyocyte viability. Successful gene transfer was grossly indicated by green fluorescence (GFP) of infected cardiomyocytes with microscopy. Over-expression of WT or L48Q cTnC and incorporation into thin filaments was demonstrated by western blot analysis of purified myofibrils from transduced myocytes probed with anti-cTnC (Santa Cruz Biotechnology, Santa Cruz, Calif.) for total cTnC content or anti-His (Novagen, Gibbstown, N.J.) for transduced protein content. To assess the approximate level of myofilament incorporation of transduced cTnC, western blot bands from transduced myocyte myofibrils were quantified by densitometry to compare total cTnC content vs. His-tag cTnC (transduced protein) content. Western blot densitometric calibration curves were generated from known quantities of cTnC and cTnC-His. FIG. 5 shows a representative example of this experiment for two cell batches, replacing ~70% (middle lanes) and 56% (right lanes) of native cTnC (FIG. 5A) with the indicated transduced cTnC-His (FIG. 5B), and compared against purified cTnC-His of known concentration (left lanes). Three batches of myocytes were run in duplicate, and averaged results indicated replacement of 58±7% of native cTnC with L48Q cTnC.

Example 6

Data Processing and Statistical Analysis. Velocity of shortening was examined using non linear regression analysis fit to a single, three parameter decaying exponential using the equation: $y=y_0+ae^{-bx}$. Relaxation was assessed by measuring the time to 50%, 90% and 100% relaxation ($RT_{50}$, $RT_{90}$, and $RT_{100}$, respectively) and by fitting to a single, three parameter exponential using the equation: $y=y_0+a(1-e^{-bx})$. Statistical differences were determined by ANOVA. Differences at the p-value <0.05 were considered statistically significant. Data displayed as mean±S.E.M.

Example 7

Adult and Neonatal Cell Isolation and Culture. These studies were approved by the University of Washington (UW) Animal Care Committee and conducted in accordance with federal guidelines. Animals were cared for in accordance with US NIH Policy on Humane Care and Use of Laboratory Animals in the Department of Comparative Medicine at UW. Adult rat (Fischer 344) cardiomyocytes (ARCs) were isolated from heart using aortic retrograde perfusion for enzymatic (collagenase/protease) dispersion of cells[13]. Neonatal Rat Cardiomyocytes (NRCs) were isolated by enzymatic dispersion from 1-3-day old newborn Fischer 344 rats as previously described[14].

Example 8

Plasmid design and virus production. HEK293 cells were used to generate adenoviral vectors[15] expressing Rrm1 or Rrm2 from the CMV promoter. Both vectors contained a second expression cassette for green fluorescent protein (GFP) as a transduction reporter protein, and we also expressed a vector for GFP-only. Virus was introduced to cardiomyocytes at ~250 particles per cell.

Transfection with recombinant adenovirus containing appropriate cDNA constructs driven by the CMV promoter was used to induce overexpression of muscle ribonucleotide reductase 1 (Rrm1) and 2 (Rrm2) in cultured adult and neonatal rat cardiomyocytes. Each adenovirus also contained a second expression cassette for green fluorescent protein (GFP), which was used as a reporter protein identifying successful transduction. Cardiomyocytes were infected with adenovirus containing genes for [Rrm1+GFP and Rrm2+GFP] or [GFP] for 2 days. Successful gene transfer, grossly indicated by green fluorescence with microscopy, indicated nearly 100% transfection efficiency. This is consistent with previous studies using cardiomyocytes[17]. Cell survival over this period was similar for all groups, including non-transduced control cells, suggesting these viral vectors did not compromise cardiomyocyte viability. Cardiomyocyte numbers and sarcomere lengths are summarized in Table 5. There was no difference in resting sarcomere length between groups, indicating that overexpression of Rrm1+Rrm2 (or GFP) did not increase calcium independent activation.

TABLE 5

| Cell characteristics | | | |
|---|---|---|---|
|  | n | SL (μm) | Cell length (μm) |
| Non-transduced | 51 | 1.88 ± 0.03 | 85.1 ± 3.6 |
| Control (GFP) | 50 | 1.84 ± 0.03 | 85.3 ± 3.2 |
| R1R2 (GFP) | 52 | 1.82 ± 0.02 | 85.2 ± 3.5 |

Example 9

Contractile Assessments. In modified Tyrodes buffer at ambient temperature, cell shortening and relaxation of arbitrarily selected stimulated cardiomyocytes was recorded using IonOptix system video microscopy. (IonOptix, Milton, Mass., USA). Calcium transients induced by electrical stimulation were measured in Fura2 loaded cells using IonOptix equipment as described[16]. Fura2 fluorescence was measured using an IonOptix spectrophotometer (Stepper Switch) attached to a fluorescence microscope. Emitted Fura2 fluorescence was collected by the 40× objective, passed through a 510 nm filter and detected by a photomultiplier tube.

The effects of Rrm1+Rrm2 overexpression on extent and rate of stimulated shortening-relengthening of adult rat cardiomyocytes was determined using video length-detection (IonOptix). FIG. 6a shows representative shortening traces, and FIG. 6b shows representative Ca2+ transients (Fura2 fluorescence), for non-treated (black), GFP-only (green), and Rrm1+Rrm2 (red) transduced cardiomyocytes. The data for all measurements at 0.5 Hz is summarized in Table 6. A deleterious effect of GFP on contractility has been previously reported[18], while others have seen no effect[16,19]. While GFP did not appear to act as a contractile inhibitor in this study, it did slow the 90% relaxation time, which was accompanied by a slower 50% and 90% decay of the Ca2+ transient (FIG. 6c, Table 5). Whether this effect was due to increased SERCA activity, or to faster cycling crossbridges that lead to shortening induced thin filament inactivation and Ca2+ release from troponin C, is a subject for future investigation. Regardless, cardiomyocytes transduced with Rrm1+Rrm2 (+GFP) had a significantly greater magnitude and rate of shortening vs. non-transduced cardiomyocytes and GFP-only transduced controls). This is illustrated in FIG. 6c, which shows % differences in rate and extent of shortening, relaxation rate, and time to 50% and 90% relaxation. Rrm1+Rrm2 overexpression increased the rate of relaxation and decreased the time to 50% relaxation, and this effect may be somewhat underestimated due to the presence of GFP. FIG. 6d illustrates the % difference in Ca2+ transient properties, including minimal and maximal Ca2+, and the time to 50% and 90% Ca2+ decay. There was no significant effect from either GFP or Rrm1+Rrm2+GFP on minimal and maximal Ca2+, indicating that enhanced contractility with Rrm1+Rrm2 was primarily due to increased myofilament responsiveness to activating Ca2+. Interestingly, Rrm1+Rrm2 overexpression did speed Ca2+ resequestration as indicated by a reduction the time to 50% and 90% decay, which may, in part, explain the increased maximal rate of cardiomyocyte relaxation.

cytes, except that time to 90% relaxation is longer at 0.5 Hz in GFP-only myocytes. The effect of stimulation frequency on Ca2+ transients was also assessed, and is summarized in FIG. 8 for minimal Ca2+ (8a), maximal Ca2+ (8b) and time to 50% (8c) and 90% (8d) Ca2+ decay ($DT_{50}$, $DT_{90}$). As with contraction, there was no difference in Ca2+ transient behavior with increased stimulation frequency between non-transduced and Rrm1+Rrm2 transduced myocytes. GFP-only transduced cardiomyocytes had a slight increase in minimal Ca2+ at 2 Hz, and an increase in maximal Ca2+ at 1 Hz and 2 Hz, as compared to non-transduced myocytes, but the times to 50% and 90% decay were similar. As at 0.5 Hz, the times to 50% and 90% decay were decreased (faster decay) in Rrm1+Rrm2 transduced myocytes at both 1 and 2 Hz.

TABLE 6

Contractile and Ca2+ transient values for 0.5 Hz stimulation.

| | Fractional Shortening (%) | Maximal Shortening Rate (μm/s) | Maximal Relaxation Rate (μm/s) | $RT_{50}$ (ms) | $RT_{90}$ (ms) | Minimal $Ca^{2+}$ (Fura ratio units) | Maximal $Ca^{2+}$ (Fura ratio units) | $DT_{50}$ (ms) | $DT_{90}$ (ms) |
|---|---|---|---|---|---|---|---|---|---|
| Non-transduced | 6.2 ± 0.4 | 61.1 ± 4.4 | 46.8 ± 6.5 | 208 ± 28 | 330 ± 59 | 1.10 ± 0.02 | 1.22 ± 0.04 | 246 ± 26 | 666 ± 74 |
| Control (GFP) | 5.5 ± 0.5 | 56.5 ± 4.4 | 37.5 ± 4.3 | 202 ± 25 | 518 ± 42* | 1.12 ± 0.03 | 1.25 ± 0.04 | 297 ± 24 | 893 ± 63* |
| R1R2 (GFP) | 8.9 ± 0.5* | 109.5 ± 8.7* | 117.9 ± 13.1* | 113 ± 7*† | 265 ± 23† | 1.14 ± 0.02 | 1.23 ± 0.03 | 153 ± 10*† | 435 ± 34*† |

*= p < 0.05 as compared to No Treat,
†= p < 0.05 as compared to GFP,
‡ = p < 0.05 as compared to 0.5 Hz for all groups.

Example 10

It is important to determine whether Rrm1+Rrm2 overexpression affects normal cellular response to increased stimulation frequency, as changes in heart rate are a normal physiological adaptation to systemic demand. FIG. 7 summarizes the effect of increased stimulation frequency (0.5 to 1 to 2 Hz) on fractional shortening (7a), shortening velocity (7b), relaxation velocity (7c), and time to 90% relaxation (7c). The contractile response to stimulation frequency was similar between groups, and Rrm1+Rrm2 transduced cardiomyocytes maintained functional potentiation at all frequencies. Importantly, increased pacing frequency is associated with a positive lusitropic effect, shortening the time to 90% relaxation in all groups. There was little difference in non-transduced myocytes vs. GFP-only transduced myo- Since there was little difference between groups in minimal and maximal Ca2+, changes in contractility can best be explained by a change in myofilament responsiveness to activating Ca2+. This is illustrated in FIG. 9 as contractile efficiency, defined here as cardiomyocyte fractional shortening divided by maximal fura2 fluorescence (peak Ca2+). Cardiomyocytes expressing Rrm1+Rrm2 had significantly higher contractile efficiency than non-transduced or GFP transduced cardiomyocytes at all stimulation frequencies. There was no difference in contractile efficiency between GFP only or non-transduced myocytes except at 2 Hz, which can be primarily be attributed to increased maximal Ca2+ in GFP only myocytes with no increase in fractional shortening, reducing efficiency. Results for 1 Hz and 2 Hz stimulation are summarized in Table 7 and Table 8, respectively.

TABLE 7

Contractile and Ca2+ transient values for 1 Hz stimulation.

| | Fractional Shortening (%) | Maximal Shortening Rate (μm/s) | Maximal Relaxation Rate (μm/s) | $RT_{50}$ (ms) | $RT_{90}$ (ms) | Minimal $Ca^{2+}$ (Fura ratio units) | Maximal $Ca^{2+}$ (Fura ratio units) | $DT_{50}$ (ms) | $DT_{90}$ (ms) |
|---|---|---|---|---|---|---|---|---|---|
| Non-transduced | 6.2 ± 0.4 | 61.9 ± 5.7 | 41.0 ± 5.5 | 191 ± 21 | 317 ± 27 | 1.07 ± 0.03 | 1.24 ± 0.04 | 191 ± 13 | 478 ± 23 |
| Control (GFP) | 6.9 ± 0.6 | 63.2 ± 6.4 | 39.7 ± 4.7 | 156 ± 15 | 365 ± 25 | 1.23 ± 0.03 | 1.39 ± 0.04 | 206 ± 11 | 511 ± 27 |
| R1R2 (GFP) | 10.7 ± 0.9*† | 126.8 ± 9.2*† | 150.2 ± 4.2*† | 110 ± 12* | 209 ± 22*† | 1.18 ± 0.03 | 1.27 ± 0.03 | 103 ± 9*† | 262 ± 20*† |

*= p < 0.05 as compared to No Treat,
†= p < 0.05 as compared to GFP,
‡ = p < 0.05 as compared to 0.5 Hz for all groups.

TABLE 8

Contractile and Ca2+ transient values for 2 Hz stimulation.

| | Fractional Shortening (%) | Maximal Shortening Rate (μm/s) | Maximal Relaxation Rate (μm/s) | $RT_{50}$ (ms) | $RT_{90}$ (ms) | Minimal $Ca^{2+}$ (Fura ratio units) | Maximal $Ca^{2+}$ (Fura ratio units) | $DT_{50}$ (ms) | $DT_{90}$ (ms) |
|---|---|---|---|---|---|---|---|---|---|
| Non-transduced | 6.9 ± 0.5 | 85.3 ± 6.7 | 61.6 ± 7.0 | 92 ± 5 | 174 ± 7 | 1.09 ± 0.02 | 1.24 ± 0.04 | 117 ± 6 | 237 ± 10 |
| Control (GFP) | 5.7 ± 1.0 | 55.3 ± 8.9 | 34.3 ± 6.1 | 113 ± 10 | 251 ± 43 | 1.28 ± 0.06 | 1.45 ± 0.08 | 141 ± 10 | 277 ± 27 |
| R1R2 (GFP) | 10.1 ± 0.8*† | 131.2 ± 12.3*† | 98.3 ± 7.7*† | 96 ± 8 | 166 ± 11 | 1.17 ± 0.04 | 1.26 ± 0.04 | 96 ± 7* | 182 ± 11* |

* = p < 0.05 as compared to No Treat,
† = p < 0.05 as compared to GFP,
‡ = p < 0.05 as compared to 0.5 Hz for all groups.

Example 11

To verify increased RR mRNA, RR protein, and dATP production in Rrm1+Rrm2 transduced cells, neonatal rat cardiomyocytes were collected and processed for RT-PCR, western blotting and HPLC analysis of intracellular [ATP] and [dATP]. Neonatal cardiomyocytes were used to achieve high enough cell density for accurate nucleotide content analysis, as intracellular [dATP] is known to be in the pM range. Similar to adult cardiomyocytes, neonatal cardiomyocyte contractility was significantly increased with R1R2 overexpression. Interestingly, as neonatal cardiomyocytes have been used to study the effects of cellular engraftment following myocardial infarction14, improved contractility in these cells may be another mechanism to improve cardiac function following an infarct. Rrm1 and Rrm2 mRNA was significantly increased following adenoviral transfection. Concomitant with this, FIGS. 10a and 10b illustrate that Rrm1 and Rrm2 transduced cardiomyocytes had greater than 24-fold and 46-fold increased Rrm1 and Rrm2 protein content, respectively. GAPDH was used as a loading control. FIG. 10c illustrates that Rrm1+Rrm2 transduced cardiomyocytes had ~10-fold increased cellular [dATP] as compared to GFP transduced cardiomyocytes (an increase to 0.35 nmol/mg protein). While this is robust, since [dATP] normally comprises less than 0.2% of total adenine triphosphate nucleotide, this increase in [dATP] represents only ~1-1.5% of the total adenine nucleotide pool. This suggests that only a small amount of dATP is required to significantly increase cardiomyocyte contractility.

Example 12

Data Processing and Statistical Analysis. Velocity of shortening and Ca2+ decay were examined using non linear regression analysis fit to a single, three parameter decaying exponential using the equation: $y=y_0+ae^{-bx}$. Relaxation velocity and Ca2+ rise were assessed by fitting to a single, three parameter exponential using the equation: $y=y_0+a(1-e^{-bx})$. Relaxation and Ca2+ decay were also assessed by measuring the time to 50% ($RT_{50}$) and 90% ($RT_{90}$) relaxation. Statistical differences were determined by ANOVA, with Student-Newman-Keuls as a post-hoc pairwise test (SigmaPlot 11). Differences at p-value <0.05 were considered statistically significant. Data is displayed as mean±s.e.m.

Example 13

In order to study molecular mechanisms of cardiac thin filament regulation of contraction and relaxation, we developed and characterized several cTnC variants. As summarized in Table 9, 1) when included in whole cTn complexes they bind Ca2+(in solution) with affinities (KA) in the order: L48Q>WT>L57Q>I61Q [KA=kon/koff], (measured via steady-state spectroscopy, 2) whole cTn Ca2+ dissociation rates (koff), (measured with stopped-flow spectroscopy) increased in the same order as KA, and 3) this correlates well with decreasing Ca2+ sensitivity (pCa50) of force when variants are exchanged into skinned cardiac trabeculae.

TABLE 9

Ca2+ binding affinity (KA) and dissociation rates (koff)
in solution, pCa50 of trabeculae force with cTnC variants

| cTnC-cTn | $K_A$ (μM) | $k_{off}$ (s$^{-1}$) | pCa$_{50}$ Force |
|---|---|---|---|
| cTnC$^{C355}$ | 0.1 ± 0.03 | 29.7 ± 0.5 | 5.25 ± 0.08 |
| L48Q cTnC$^{C355}$ | 0.08 ± 0.01 | 7.3 ± 0.1* | 5.63 ± 0.08 |
| L57Q cTnC$^{C355}$ | 0.3 ± 0.01 | 51.8 ± 2.1 | 4.93 ± 0.06 |
| I61Q cTnC$^{C355}$ | 0.5 ± 0.01 | 76.8 ± 9.5 | 4.77 ± 0.05 |

Adenoviral vectors (AV) were created for each variant and transfected cultured adult rat cardiomyocytes (~250 viral particles/cell), identified by co-expression of GFP. Shortening and intracellular Ca2+ transient data are summarized in Table 10. The data (0.5 Hz stimulation) show magnitude and rate of shortening decreased in the order L48Q>WT>L57Q>I61Q, the same order as for solution Ca2+ affinities and Ca2+ sensitivity of skinned cardiac muscle. All cTnC variants in AV constructs contained a C-terminal Histidine tag, allowing SDS-PAGE and western blot analysis for quantitative assessment of the amount of incorporation into myofilaments. This level usually ranges from 40-60% with the AV load we typically use. Interestingly, L48Q cTnC had no effect on Ca2+ transient amplitude, suggesting enhanced shortening results solely from increased myofilament Ca2+ sensitivity. In contrast, L57Q and I61Q cTnC reduced shortening/relaxation performance and reduced Ca2+ transient baseline and amplitude. The simultaneous reduction in shortening, Ca2+ transient amplitude and +kFL suggests myofilament-SR interplay after only 48 hours in culture.

TABLE 10

Shortening and Ca2+ transient data for cells transfected with AV-c TnC variants (48 hrs).

| | | | MECHANICS | | | Ca$^{2+}$ TRANSIENT | | |
|---|---|---|---|---|---|---|---|---|
| AV-c TrC | n | SL | % Shorten | k$_{shorten}$ (μm s$^{-1}$) | RT$_{90}$ (ms) | Amplitude | +k FL (s$^{-1}$) | RT$_{90}$ (ms) |
| GFP only | 50 | 1.84 ± 0.03 | 5.5 ± 0.4 | 56.5 ± 4.4 | 222 ± 25 | 1.27 ± 0.04 | 3.0 ± 0.2 | 833 ± 63 |
| WT | 43 | 1.72 ± 0.02 | 6.4 ± 0.4 | 59.4 ± 4.2 | 134 ± 15* | 1.28 ± 0.03 | 2.2 ± 0.2 | 669 ± 65* |
| L48Q | 54 | 1.84 ± 0.02 | 8.9 ± 0.5*† | 115.1 ± 7.0* | 151 ± 12* | 1.24 ± 0.03 | 3.3 ± 0.3† | 750 ± 47* |
| L57Q | 17 | 1.70 ± 0.04 | 2.1 ± 0.4*† | 27.8 ± 5.3*† | 112 ± 24*† | 1.11 ± 0.04*† | 2.0 ± 0.4* | 607 ± 87 |
| I61Q | 17 | 1.60 ± 0.04 | 2.0 ± 0.4*† | 23.0 ± 5.1*† | 135 ± 23* | 1.0 ± 0.05*† | 1.4 ± 0.6*† | 574 ± 90* |

†= Significantly different (p < 0.05) vs. WT cTnC.
*= Significantly different (p < 0.05) vs. GFP only.

From the data provided in Table 9 and Table 10, we determined that cTnC variants which increase/decrease Ca2+ sensitivity of force in skinned cardiac muscle also increase/decrease the magnitude and rate of contraction in cultured cardiomyocytes. Interestingly, both L57Q and I61Q cTnC reduce contractility with concomitant decreases in the Ca2+ transient, whereas L48Q cTnC increases contractility without altering Ca2+ transient amplitude or slowing relaxation (Table 10). This occurred even though the variants only partially replaced native proteins in cardiomyocyte thin filaments, demonstrating cTnC variants can have substantial impact on myofilament contraction and influence SR function without completely replacing native cTnC. These heterogeneous populations of native and variant species also mimic variable penetration of mutations in animal models and human disease, and will likely be similar to incorporation profiles in in vivo cardiac studies.

Shortening and Ca2+ transients were reduced in cardiomyocytes from hearts infarcted (4 weeks) by permanent ligation of the left descending coronary artery (FIG. 11). The impaired contractile behavior may result primarily from reduced Ca2+ transients (Table 11). Importantly, L48Q cTnC expression rescued both shortening and Ca2+ transient amplitude of these cardiomyocytes (FIG. 11, Table 11), in contrast to normal cardiomyocytes where only shortening was enhanced. This suggests L48Q cTnC expression affects not only myofilament Ca2+ sensitivity of contraction, but can also affect SR function in failing myocardium. This is likely due to myofilament incorporated cTnC and not cytosolic pools of cTnC, as transfection with AV-WT cTnC did not alter contractile or Ca2+ transient properties (data not shown).

Changes in contractility and Ca2+ transients occurred in culture without a stimulation history, as adult cardiomyocytes were quiescent until assessment (48-72 hours), suggesting altered Ca2+ transients may result from changes in post-translational modification (phosphorylation) of SR and/or sarcolemmal proteins, as opposed to altered protein content. To demonstrate the importance of stimulation history, we compared shortening and Ca2+ transient amplitude of unstimulated (quiescent) vs. chronically stimulated (1 Hz) cardiomyocytes (FIG. 17) and found 45% greater shortening, 28% greater Ca2+ transient amplitude and >50% faster Ca2+ transient rise (+kFL) and decay (kDecay) for the stimulated cells 30 hours after plating.

Example 14

Gene delivery via AAV6+cardiac-specific promoter. Production of rAAV6 vectors will be as previously described[39]. Vectors for WT and L48Q cTnC (AAV6-WT cTnC, AAV6-L48Q cTnC respectively) have already been produced, and vectors for I61Q and L57Q cTnC are in production. Briefly, plasmids will be produced with recombinant AAV genomes containing a cardiac specific promoter (cTnT455, provided by Dr. Steven Hauschka, Univ. of Washington) and C-terminal c-Myc tag. cTnC variant transgene expression (with a mCherry fluorescent reporter) cassettes are co-transfected into HEK293 cells with a packaging/helper plasmid pDGM6 by CaPO4 precipitation methodology. Vectors are collected from culture, freeze-thawed, and the supernatant collected. Affinity purification uses a HiTrap heparin column (GE Healthcare, Piscataway, N.J.). The virus is concentrated on a sucrose gradient (40%), spun at 27,000 rpm (18 hours, 4° C.), and resolubilized in Hanks balanced solution. Vector genomes are determined relative to plasmid standards using a SV40 poly adenylation region oligonucleotide 32P end-labeled probe with Southern blot hybridization and confirmed by qPCR.

FIG. 12 demonstrates the first use of the AAV6-L48Q cTnC systemically injected (intraocular) into 3 mice each at low (L; 0.6×10$^{12}$) and high (H; 1.2×10$^{12}$) viral particle dose.

TABLE 11

Effect of L48Q on contraction and CA2+ transients of cardiomyocytes from infarcted hearts.

| | | | MECHANICS | | | Ca$^{2+}$ TRANSIENT | | |
|---|---|---|---|---|---|---|---|---|
| AV-c TnC | n | SL | % Shorten | k$_{Shorten}$ (μm s$^{-1}$) | RT$_{60}$ (ms) | Amplitude | + kFL (s$^{-1}$) | RT$_{90}$ (ms) |
| GFP only | 41 | 1.81 ± 0.03 | 3.9 ± 0.5 | 38.0 ± 4.6 | 343 ± 49 | 1.19 ± 0.02 | 2.3 ± 0.3 | 834 ± 61 |
| L48Q | 33 | 1.87 ± 0.03 | 9.3 ± 0.8* | 90.6 ± 7.0* | 182 ± 17* | 1.29 ± 0.06* | 3.7 ± 0.6* | 827 ± 72 |

Echocardiography indicated a ~20% increase in left ventricular (LV) ejection fraction compared with uninjected (UN) controls two weeks after injection, and a 30-40% increase at 3 weeks. While sham and AAV6 control injections need to be performed to confirm this result, systemic injections with control AV vectors have not altered LV function. Myofibrils from one AAV6 L48Q cTnC-myc transfected mouse (and uninjected control) were separated by SDS-PAGE and western blots were probed with anti-cTnC. The presence of myc-tag caused slower migration of cTnC (FIG. 13), and the ratio of cTnC-myc to native cTnC was densitometrically determined to be ~40% (similar to that seen with adenovirus and transgenic animals, below).

Example 15

Gene delivery via Adenoviruses (AV). AV vectors are more effective in culture so, for some experiments, we will continue to use them for cTnC variant transfection in cardiomyocytes. AV vectors are produced by HEK293 cells with the reporter protein GFP expressed as a separate cassette in the same virus for identifying transduced cells (FIG. 14). These vectors regularly results in 40-60% replacement of native cTnC in myofibrils of cultured cardiomyocytes. This level is similar to that achieved for the L48Q and I61Q cTnC inducible mice from the Molkentin group (below).

Example 16

Use of transgenic L48Q and I61Q cTnC mice. Transgenic mice were developed that express wild type (WT), L48Q or I61Q cTnC. All constructs utilize an inducible cardiac specific α-myosin heavy chain (α-MHC) promoter[40], and contain a single 3' flag epitope tag previously shown not to affect myocyte structure or function[41]. The percent replacement of native cTnC with flag tagged cTnC was assessed for each line by western blot of whole heart lysates using both a cTnC specific monoclonal antibody (Abcam, 1A2 clone) and an anti-flag antibody (Sigma).

As the flag epitope causes a slower mobility cTnC band (FIG. 15), the ratio of transgenic cTnC to native cTnC was determined by densitometry. The proportion of flag tagged cTnC to total cTnC represents the % replacement. The highest expressing lines for each construct had ~40-50% replacement, similar to the expected replacement for inherited cardiomyopathy patients. Additionally, we have shown that this % replacement of native cTnC with variant cTnC is sufficient to produce increased Ca2+ sensitivity in skinned preparations and increased shortening in intact myocytes. We will confirm this using titration ratios (WT:mutant) in skinned trabeculae and cultured cardiomyocytes to compare with animal models. The flag antibody also provides evidence of the robust expression of the transgene in double transgenic mice (DTG, TTA+ and cTnC+) but also show a slight leak of the inducible α-MHC promoter in mice that are positive for the transgene alone.

Example 17

Use of transgenic R92W/L cTnT mice. The mutations are analogous to those found in human cardiomyopathy patients. Heterozygous mice incorporate ~50% (range 35-70%) of the cTnT variant into myofilaments and experience mild hypertrophy. Skinned cardiac tissue from these mice have increased Ca2+ sensitivity (0.3-0.4 pCa units) at both short (1.9 µm) and long (2.3 µm) sarcomere lengths (SL)[15]. Cultured cardiomyocytes have shorter resting SL, a decreased rate of shortening and relaxation, and decreased Ca2+ transient amplitude and rate of rise/fall at 2 months. This improves somewhat by 6 months suggesting adaptation. The altered Ca2+ dynamics is associated with increased SR load and phosphorylation of Ser16, 17 of phospholamban (PLB).

Example 18

Preparation of infarcted hearts. Myocardial infarction is achieved by permanent ligation of the left descending coronary artery. This typically results in an infarct zone measuring ~30-35% of the left ventricular free wall cross-section area (10-15% of total LV area) with reduced fractional shortening and increased cavity dilation via echo-cardiography (FIG. 16A-C), and loss of responsiveness to increased pre-load via working heart measurements (FIG. 6D).

Example 19

We will use cultured adult cardiomyocytes, cultured trabeculae and myofibril preparations to study the influence of cTnC variants on contraction and SR function. While cultured cardiomyocytes provide detailed information on SR function during shortening/relaxation cycles, cells do not experience external strain as in the heart. Cultured trabeculae allow measures of isometric force and shortening under load, along with monitoring Ca2+ transients. We will use small, thin trabeculae with few cell layers (in depth) to maximize diffusion and avoid signal variations due to fluoroprobe penetration and diffusion gradients within the preparation. Isolated myofibril mechanics measurements will allow detailed study of contraction and relaxation kinetics during maximal and sub-maximal Ca2+ activation and with varying (controllable) and quantifiable levels of cTnC variants incorporated into myofibril thin filaments. Table 12 summarizes experiments for this aim, including the preparation, varying stimulation history (24-48 hrs. transfection with AV vectors), conditions to be tested and measures made at the end of stimulation history.

TABLE 12

Summary of experimental preparations and procedures

| PREPARATIONS | STIM HISTORY | PROTOCOLS | MEASUREMENTS | LAB |
|---|---|---|---|---|
| Single cardiomyocytes | 0, 1, 10, 30 min 1, 6, 12, 24 hrs | ±α or β-adrenergic vary($Ca^{2+}$)$_{ext}$ (0.5-6 mM) ± CB Inhibitors | shortening & $Ca^{2+}$ transients (0.5-3 Hz) SR function(release, reuptake, load, sparks) | Regnier Santana |
| Trabeculae (Intact) | 0, 1, 10, 30 min 1, 12, 24 hrs | ±α or β-adrenergic vary($Ca^{2+}$)$_{ext}$ (0.5-6 mM) ± CB Inhibitors | Isometric Force (0.5-3 Hz) | Regnier |
| Trabeculae (Skinned) | | vary($Ca^{2+}$)$_i$ ± PKA, PKC, CB Inhibitors | pCa vs. Force, $k_{TR}$, Rest Stiffness | Regnier |
| Myofibrils | | vary($Ca^{2+}$)$_i$ ± PKA, PKC, CB Inhibitors varying ATP, ADP, PI, pH | $k_{ACT}$, $k_{TR}$, $k_{REL}$ | Regnier |

As outlined in Table 12, following transfection of cultured adult rat cardiomyocytes with AV vectors for WT, L48Q, L57Q, or I61Q cTnC, we will measure contractility and Ca2+ transients of unstimulated cells vs. cells with stimulation history. Short term 1 Hz stimulation histories (0-30 min) will provide information on acute adaptive responses of myofilaments and SR function, associated with rapid adrenergic responses, while longer stimulation (1-24 hrs) yields information about longer term adaptive response, including transcriptional regulation (determined from real time PCR (RT-PCR)) of myofilament, SR, sarcolemmal proteins and associated kinases. Initial experiments will allow us to determine whether stimulation histories alter contraction, Ca2+ cycling behavior, and adrenergic responsiveness. We will then independently study these effects under the following experimental conditions.

We will vary extracellular [Ca2+]([Ca2+]$_{ext}$) to determine potential effects on Ca2+ induced Ca2+ release (CICR), and use myofilament crossbridge (CB) inhibitors (BDM, blebbistatin) to determine the influence of contractile mechanics on SR function. We will use α-(phenylephrine) or β-adrenergic (isoproterenol) challenge to determine if the response is dependent on cTnC variants and its interaction with cTnI. CB inhibitors and adrenergic agonists will be removed prior to contractile and Ca2+ transient measurements.

For shortening and Ca2+ transient measurements, cardiomyocytes will be loaded with fura-2 AM and contraction/relaxation at 0.5, 1, 2 and 3 Hz will be monitored using video microscopy (IonOptix, Milton, Mass.). For measures of SR function, (Co—I), global [Ca2+]$_i$ will be imaged in isolated cardiomyoctyes loaded with membrane-permeant acetoxymethyl-ester form of rhod-2 or fluo-4 using a Nikon swept field confocal system coupled with a Nikon x60 lens (NA=1.4), as previously described[42]. Measurements will include the amplitude and frequency of localized Ca2+ release events (sparks) from ryanodine receptors (RyR), macroscopic Ca2+ release and reuptake behavior and SR Ca2+ load using caffeine-induced SR Ca2+ depletion, all routinely done in the Santana lab[42-46]. FIG. 18 shows example Ca2+ transient traces (rhod-2) demonstrating L48Q cTnC slightly speeds RT90 and decay rate (τ) compared with WT cTnC. The corresponding data is summarized in Table 13.

TABLE 13

Ca2+ transient (rhod-2 fluorescence) amplitude and kinetics (1 Hz stim.) for uninfected (NA), vs. AV infection with WT and L48Q cTnC.

| AV-cTnC | n | Amplitude | Time to peak (ms) | RT$_{50}$ (ms) | Decay τ (ms) |
|---|---|---|---|---|---|
| NA | 7 | 1.74 ± 0.20 | 19.0 ± 0.77 | 637 ± 33 | 322 ± 28* |
| WT | 6 | 1.39 ± 0.14 | 10.5 ± 1.4 | 693 ± 19 | 400 ± 25 |
| L48Q | 10 | 1.50 ± 0.16 | 19.5 ± 1.1 | 562 ± 38* | 293 ± 18* |

Example 20

Experiments with Cultured and Skinned Trabeculae: We will determine how cTnC variants affect contraction under external load and at varied sarcomere lengths (SL), as occurs in vivo. Thin (<120 μm diameter, ~50 μm depth) cardiac trabeculae will be cultured as reported by Adler et al.[47] and by Janssen et al.[48] following transfection with AV vectors for all cTnC variants.

Initial experiments will determine the period of transfection that results in optimal cTnC mutant incorporation into thin filaments. Significant protein production occurs within 24 hours of AV transfection in cultured cardiomyocytes, as indicated by GFP signal, and we expect similar results with trabeculae. Contraction and Ca2+ transients will be measured following 1 Hz stimulation histories (Table 12). Preparations will be loaded with fura-2, and mounted between a force transducer and linear motor in an oxygenated perfusion chamber containing stimulating electrodes[49-51]. For stimulation periods <60 minutes, fura-2 loading will be done prior to initiation of the stimulation protocol. Isometric twitch force and Ca2+ transients, and their SL dependence (Frank-Starling relationship, SL=1.9 vs. 2.2 μm), will be measured under the same protocols as for cultured cardiomyocytes (see above). We will use a standard Krebs-Henseleit solution, 95/5% O2/CO2 and 37° C.[48]. Steady contractile properties have previously been maintained for 24-36 hours[52] at 0.2-0.5 Hz stimulation, and we expect little difficulty in extending this to 48+ hours.

To obtain detail about how myofilament contraction is affected by cTnC variants at controlled, sub-maximal levels of Ca2+ we will chemically demembranate (skin) transduced trabeculae following the stimulation protocol. We will measure pCa vs. force and the rate of force redevelopment (kTR) and loaded shortening at long and short SL. In complimentary experiments skinned trabeculae will be exchanged with mixtures of cTnC variants and WT cTnC to determine the critical level of variant incorporation (into thin filaments) that affects contraction. cTnC variant incorporation into myofilaments will be quantified (see below).

Example 21

Experiments with Myofibrils: Myofilament relaxation is an important component of normal cardiac function; ventricles must relax rapidly following systole to allow sufficient diastolic filling. This important process is often altered in pathological conditions. Relaxation is difficult to assess in skinned trabeculae that have large diffusion distances. Myofibril preparations, however, have small diffusion distances that allow rapid solution switching and force measurements on the ms time scale, allowing assessment of cTnC variants on myofibril activation and relaxation, independent of intact cell Ca2+ transients. In separate experiments, following the stimulation protocol, myofibril preparations will be made from minced cardiac muscle transfected with cTnC variants to measure Ca2+ dependence of the rate of force development (kact) and kTR, and the slow (kREL,slow) and fast (kREL,fast) rates of relaxation. Examples of how recombinant WT, L48Q and I61Q cTnC exchanged into rat cardiac myofibrils affect these parameters is shown FIG. 19. Panel B shows a small, but significant increase in kREL, slow and 50% relaxation time with L48Q cTnC. This appears at odds with the data in cultured cardiomyocytes (Table 10). The apparent difference could be explained by 1) isometric vs. unloaded conditions, 2) different amounts and time course of activating Ca2+, 3) differences in % cTnC incorporated into myofibrils, 4) differences in myofilament phosphorylation or 5) differences in ADP, Pi or pH that are known to affect relaxation kinetics. In myofibril studies we can independently vary [ATP], [ADP], [P$_i$], [Ca2+], pH and phosphorylation of myofilament proteins (PKA, PKC, phosphatases, etc.), all conditions that vary in the heart and are difficult to control in intact cardiac preparations. A significant strength of this technique is that force development and relaxation are studied in the same protocol, providing measures that have relevance for the isovolumetric (isometric) phases of cardiac systole (kact) and diastole (kREL).

Example 22

Protein Profiling: Changes in contractile function, Ca2+ transients, SR spark activity and/or Ca2+ load under all conditions will be correlated with abundance and phosphorylation of myofilament proteins (cTnI, cTnT, MLC-2, cMyBP-C and Tm), SR proteins (PLB, RyR), and sarcolemmal proteins (PMCA, L-type Ca2+ channel) from high-density cell cultures matching the protocol conditions in Table 12. Changes in protein expression will be determined using RT-PCR and Western blot analysis. SR protein fractions will be prepared according to published methods[53-56]. Analysis of cTnC variant incorporation will be made via Western blots of myofibril preparations from transfected cells. Identification of transduced proteins is possible due to a c-terminal histidine tag (His-tag) on cDNA for AV vectors; AAV6 vectors contain a C-terminal c-myc tag for the same purpose. SDS-PAGE provides protein stoichiometry and western blots are probed using cTnC vs. His-tag or c-myc antibodies for ratiometric analysis (example as in FIG. 20). Changes in phosphorylation will be determined using Pro-Q diamond (with Sypro Ruby stain for protein content) and western blot analysis. FIG. 21 shows that myofilament protein phosphorylation does not did not differ for WT vs. I61Q cTnC transfected cardiomyocytes, suggesting reduced shortening with I61Q cTnC (Table 10) results from changes in troponin Ca2+ binding and SR Ca2+ release. For site specific serine and threonine residue phosphorylation, we can send samples for mass spectrometry analysis.

Example 23

The systematic set of studies outlined in Examples 19 to 22 will produce detailed information on how altered cardiac thin filament Ca2+ binding influences contractile and Ca2+ homeostasis under a variety of conditions, and how responses may be mediated through post-translational modification (phosphorylation) of proteins. We expect that there is a direct relationship between alterations in myofilament Ca2+ binding and the regulation of Ca2+ homeostasis in cardiomyocytes. A few expected results and potential hypotheses are:

L48Q cTnC: L48Q cTnC increased myofilament Ca2+ sensitivity (Table 9) and shortening with little effect on Ca2+ transients of quiescent cardiomyocytes (Table 10), while 24 hrs of 1 Hz stimulation increased both and also sped Ca2+ transient decay (FIG. 17). This suggests stimulation may primarily effect sarcolemmal and SR Ca2+ behavior in vitro, while L48Q cTnC primarily affects myofilament behavior. Thus, we expect stimulation history to affect SR function (Ca2+ loading, CICR, etc.) with concomitant increases in force and shortening, perhaps via SR/sarcolemmal protein phosphorylation. For example, increased Ca2+ transient amplitude and re-sequestration following stimulation history could be due to increased phosphorylation of RyR and PLB, respectively[57,58]. As such, we expect β-adrenergic stimulation to affect unstimulated cells more than those with stimulation history. We expect crossbridge (CB) inhibition to reduce SR function similar to that seen with I61Q cTnC, which also reduces contractility (FIG. 11; Table 10). Combined, this would suggest a hypothesis that mechanical behavior (or Ca2+ buffering capacity) of myofilaments affects SR function during stimulated contraction, as opposed to electrical stimulation of SR Ca2+ release per se. If so, CB inhibition should affect loaded contractions of intact trabeculae more than unloaded cardiomyocytes, as CB numbers increase with load. As L48Q cTnC had little effect on Ca2+ transients, we expect little or no change in SR function, myofilament or SR protein content, or phosphorylation of unstimulated cells. This may differ with stimulation history and in intact trabeculae due to greater myofilament Ca2+ sensitivity and greater CB activity.

I61Q & L57Q cTnC: L57Q and I61Q cTnC decreased myofilament Ca2+ sensitivity, shortening and Ca2+ transient amplitude of quiescent cardiomyocytes (Table 10). This supports the previously stated hypothesis (previous paragraph) that myofilament activity can drive changes in SR function (as also seen with stimulation history). Results will help determine specific mechanistic changes resulting in reduced Ca2+ transients. For example, reduced SR Ca2+ release with L57Q or I61Q cTnC would suggests reduced RyR phosphorylation, resulting from reduced kinase activity or enhanced phosphatase activity. Alternatively, these cTnC variants may drive changes in SR Ca2+ loading (via reduced PLB phosphorylation), which would also reduce Ca2+ transient amplitude. If so, β-adrenergic stimulation would have a greater effect on increasing SR function and Ca2+ transients in I61Q or L57Q cTnC transfected cells compared to WT or L48Q cTnC. We expect higher stimulation frequencies (2-3 Hz vs. 0.5 Hz during measurements) to increase contractility by enhancing CICR and Ca2+ binding to thin filaments, which may in turn alter SR loading and function. It will be interesting to see if stimulation history (1 Hz) provides a similar effect. We expect increasing $[Ca2+]_{ext}$ will ameliorate effects of L57Q or I61Q cTnC on Ca2+ transients and SR function by strengthening the CICR mechanism.

Relaxation: We expect relaxation of intact trabeculae to be affected by cTnC variants, although relaxation was little affected in cultured cardiomyocytes. This is because contraction in cultured cardiomyocytes is unloaded, while trabeculae will undergo isometric contraction. Thus cTnC Ca2+ binding properties could have a more prominent effect during loaded contractions, where relaxation kinetics are primarily determined by crossbridge cycling rates, and ATP hydrolysis substrate/product conditions that change in ischemia[59-64]. If twitch relaxation is affected by cTnC variants we expect relaxation rates (especially kREL,slow) of submaximal (Ca2+) activated myofibrils to be similarly affected. Myofibril experiments will also allow us to determine if relaxation changes are due to myofilament behavior and not SR function.

Example 24

We will study acute and chronic effects of cTnC variants on cardiac function using AAV6-cTnC vectors and transgenic mice. To determine the response to acute changes in myofilament function we will transfect normal adult mice via tail vein or intraocular orbit injection of AAV6-cTnC variants (WT, L48Q, L57Q, or I61Q) with a cardiac specific promoter (cTnT455). Parallel experiments will be performed with the L48Q cTnC and I61Q cTnC transgenic mice by repressing the MHC promoter until adulthood. Additional studies will be done with mice without repression of the promoter to determine the effects of these cTnC variants on normal cardiac development and function. To limit the scope of this aim, we will focus studies primarily on adult mice. However, we will do echocardiographic assessments at 1, 2, 3 and 6 months of age to determine onset and progression of any changes in function. Some animals will be stressed via β-adrenergic stimulation with isoproterenol. Following echocardiography some animals will undergo hemodynamic measurements using Millar catheter protocols, others will be euthanized and hearts dissected for working heart protocols or for intact or skinned trabeculae preparations, cultured cardiomyocytes or myofibril preparations.

Example 25

Echocardiography. In vivo cardiac function assessments will be made non-invasively with echocardiography.

Parasternal long axis images will be used to determine flow velocity across the left ventricular outflow tract and the outflow tract cross sectional area (CSA), to calculate stroke volume (SV=CSA×time velocity integral (area of the aortic flow velocity)) and cardiac output (CO=SV×heart rate)[65]. Short axis 2-D views at the mid-ventricular (papillary muscle) level will be used to generate M-mode measurements of the left ventricular end-systolic (LVESD) and end-diastolic (LVEDD), anterior and posterior wall (PW) dimensions. These will be used to calculate percent fractional shortening [(LVEDD−LVESD)/LVEDD×100%] and left ventricular wall mass [1.05(IVS thickness+LVEDD+PW thickness)][66,67]. Quality control will be achieved by determining intra-observer and inter-observer variability for a single reader during two different sessions and two blinded readers obtaining measurements for several images.

Example 26

In Vivo Physiology. Real-time assessment of cardiac contractility, and alterations in the Frank-Starling & pressure-volume relations will be made using miniaturized impedance/micromanometer catheters (Millar Instruments). Hemodynamic parameters will include heart rate, end diastolic and systolic pressures, +dP/dt, −dP/dt, slope of stroke work (SW) vs. end diastolic volume (EDV), and the time constant of ventricular pressure decay. These work-performing parameters can be better compared with in vitro working heart (see below), trabeculae and myofibril measurements in studying the dynamics of contraction/relaxation parameters of mouse hearts under similar pre- and after-loads.

Example 27

In Vitro Working Heart. Following echocardiography, at the endpoint of animal experiments, some hearts will be excised and mounted on a working heart apparatus (Experimetria) for assessment of pump performance and ability to respond to varying pre- and after-loads (±isoproterenol), which is more difficult to assess in vivo. These hearts will then be processed for morphological and histological analysis. FIG. 16D shows decreased response (power output) to preload in infarcted rat hearts as compared to normal heart.

Example 28

Trabeculae, Cardiomyocytes and Myofibrils. Following endpoint echocardiography, some hearts will be excised and ventricles will be prepared for 1) dissection of intact or skinned trabeculae, 2) cardiomyocytes in culture, or 3) myofibril preparations. Experimental measurements will be conducted as described above.

Example 29

Morphological and Histological Analysis: Some dissected hearts, including those used for in vitro working heart measurements, will be taken for gravimetric analysis, fixed, embedded and stained (H&E, Masson's Trichrome, Picrosirius Red) according to well-established procedure[27,68]. Sections will be evaluated for signs of hypertrophy (cellular and ventricular) and dilation. To assess potential fibrosis, % collagen area will be quantified from images under circular polarized light by number of picrosirius red-positive pixels as a % of total pixels. Serial sections of transduced hearts will be analyzed using ImageJ for quantification of percent mCherry (or myc-tag) positive cells to correlate with changes in in vivo and in vitro function following AAV6-cTnC variant treatment.

Example 30

The systematic set of studies outlined in Examples 24 to 29 will produce detailed information about short and long term cardiac adaptation to mutations that affect myofilament Ca2+ sensitivity of contraction in vivo where intrinsic adaptation is subject to constant paracrine and hormonal fluctuations. We expect that cTnC variants that alter Ca2+ sensitivity of myofilaments will have different acute vs. chronic effects on cardiac function, SR function and myofilament/SR protein profile. Whereas heart failure is associated with down-regulation of β-adrenergic responsiveness, (and up-regulation of PKC expression and target phosphorylation[69-71], we expect I61Q cTnC may increase β-adrenergic mediated effects in the short term in an attempt to increase cardiac pump function. Similarly, increased cardiac contractility with L48Q cTnC (FIG. 12) may lead to decreased β-adrenergic responsiveness. Additionally, we may find a blunting of the Frank-Starling mechanism of increased pump (in vivo) and cardiac tissue contraction (in vitro) in the short term with L48Q cTnC as contractile activation is markedly improved, requiring less CB contribution to thin filament activation[72]. For I61Q cTnC, the Frank-Starling mechanism may remain intact, but pump function overall is likely to be reduced. In transgenic animals, these affects may be abrogated via longer term adaptations of SR protein content and/or phosphorylation that compensate for changes in myofilament contractility.

We will also directly test whether altered myofilament Ca2+ sensitivity per se can produce a hypertrophic or dilated ventricular functional and morphological phenotype. We hypothesize this will not occur with relatively short exposure to AAV6-cTnC transduction, but may occur to some extent as transgenic mice with L48Q cTnC (hypertrophy) and I61Q (dilation) age. We expect to see differences in SR/sarcolemmal and myofilament protein phosphorylation profiles for each of these cTnC variant exposure histories.

Example 31

We will study the effect of L48Q cTnC on infarcted hearts and I61Q (or L57Q) cTnC on young and adult mice with the R92W/L cTnT mutations. Infarcted Hearts. To determine if L48Q cTnC can improve cardiac function following myocardial infarct we will transfect mice with AAV6-L48Q cTnC at 3-7 days post-infarct surgery, following echocardiography to characterize extent of functional deficit. Initial echocardiographic assessments will be made 1, 2, 4 and 8 weeks post-transfection to determine the best time points to study gains in function. We will also do vector dose studies to determine optimal treatment regimens and correlate this with measures of L48Q cTnC incorporation into myofibrils (shown above). The low dose ($0.6 \times 10^{12}$) injected into normal mice (FIG. 12) was quite effective at increasing ejection fraction. In some animals, we will then measure in situ hemodynamic properties via Millar catheter experiments (as described above). Additional animals will be used for in vitro studies on working heart, intact and skinned trabeculae, cultured cardiomyocytes and isolated myofibrils. As above, we will determine which preparations are the most instructive and focus the majority of measurements on them to limit the number of animals required for these studies. To determine if L48Q cTnC prevents loss of left ventricular function, a separate set of animals will be transfected with AAV6-L48Q cTnC prior to infarct surgery. Some dissected hearts, including those used for in vitro working heart measurements, will be taken for gravimetric analysis, fixed, embedded and stained, and evaluated for signs of hypertrophy and fibrosis (as described above). Serial sections of infarcted hearts will be analyzed using ImageJ to quantitate infarct size and % mCherry positive cells, to correlate with altered in vivo and in vitro function following AAV6-L48Q cTnC transfection.

Example 32

R92W/L cTnT Transgenic Mice. R92W/L cTnT mice will be transfected with AAV6-I61Q (or L57Q) cTnC at age one month to determine if these variants reduce or eliminate the functional phenotype reported at two months, including depressed cardiac function, increased myofilament Ca2+ sensitivity and reduced SR function (associated with PLB ser16, 17 phosphorylation[58-73]. R92W hearts undergo early (2 month) induction of cardiomyopathic markers (atrial natriuretic factor, α-skeletal actin) compared with later induction (10 month) with R92L, so we will also transfect 5-6 month old R92L mice to determine if the later treatment reduces or eliminates the late stage mild hypertrophy in R92L mice. Echocardiographic analysis will be made at the established timepoint (FIG. 12) where stable expression and incorporation of I61Q (or L57Q) cTnC into myofilaments has occurred. Some mice will be followed bi-monthly to one year of age to determine if effects of AAV6 treatment on cardiac function persist. At the endpoint of measurements, some animals will be used for in situ hemodynamic measurements (as described above), and others used for in vitro studies on working heart, intact and skinned trabeculae, cultured cardiomyocytes and isolated myofibrils as described above.

Example 33

Echocardiographic Strain Analysis. In addition to M-mode measures, current echocardiographic transducers provide resolution sufficient for advanced functional assessments. This includes measurements of systolic and diastolic segmental strain and strain rates that provide in vivo correlates to in vitro measurements, providing additional functional parameters on ventricular wall compliance and (proper) wall motion. This will be instructive for studying the influence of cTnC variants on normal, infarcted hearts, and R92W/L HCM hearts. Strain represents the change in length from the original unstressed dimension of the myocardium by lengthening, compression, or shortening[77,78] and strain rate measures the change in dimension over time between the two points of interest. Speckle tracking assigns unique grayscale speckles generated by ultrasound beams, whose unique patterns are followed by software to calculate strain and strain rates based on the velocity of speckle movement during one cardiac cycle[79,80]. An example speckle tracking study (FIG. 22) shows systolic and diastolic heart function in hyperglycemic mice. Since speckle tracking is acquired using short axis views as in traditional echocardiography, no additional studies will be required.

We expect that increasing Ca2+ sensitivity of myofilaments (L48Q cTnC) will increase cardiac performance of infarcted hearts, and slow the progression of heart failure. This may occur by lessening chronic β-adrenergic stimulation. If so, we expect to see a time dependent difference in the balance of parasympathetic and sympathetic tone reflected in α- and β-adrenergic mediated protein phosphorylation between L48Q cTnC transduced vs. untreated infarcted hearts.

For the R92W cTnT mice, we expect I61Q cTnC transduction at 1 month will at least partially abrogate the deleterious effects of R92W cTnT seen at 2 months of age, ultimately resulting in increased cardiac performance. This may result from altered phosphorylation of SR proteins (such as PLB) and SR Ca2+ load that have been shown to occur in the adaptive response of these mice as they age (58). Similarly, we expect later I61Q cTnC transduction (at 5-6 months of age) of R92L cTnC mice to also alter phosphorylation of SR proteins, improving function and slowing the hypertrophic response.

Example 34

The effect of elevated R1R2 and [dATP] on stimulated contraction of cultured adult rat cardiomyocytes was characterized. Adenoviral (AV) Vectors. R1R2 over-expression was induced by transduction of cardiomyocytes for ~48 hours with AV vectors (~250 particles/cell), driven by the CMV promoter that express either the R1 or R2 subunit and a 2nd expression cassette for green fluorescent protein (GFP). We also produced a GFP-only AV vector as a transduction/reporter control. To determine the extent of R1R2 over-expression, neonatal rat cardiomyocytes were transduced with AV vectors under identical conditions and protein levels determined with western blot analysis. R1 (FIG. 23A) and R2 (FIG. 23B) were increased 24-fold and 46-fold, respectively, with GAPDH as a loading control. HPLC analysis indicates this increased cellular [dATP] ~10-fold (0.35 nmol/mg protein) over GFP transduced cardiomyocytes (FIG. 23C). This was consistent (range 8-12-fold) across multiple cell batches for this AV particle load. While this effect is robust, since [dATP] normally comprises >0.2% of the total adenine triphosphate nucleotide, the elevated [dATP] still represents only ~1-1.5% of the adenine nucleotide pool. This suggests only a small amount of dATP is required to significantly increase cardiomyocyte contractility.

Example 35

R1R2 over-expression enhances cardiomyocyte contractility. Example traces (FIG. 24) show that AV-R1R2 transduction resulted in much greater cardiomyocyte shortening (A) with no increase in maximal intracellular Ca2+(B; Fura-2), using video length detection and fluorescence imaging (IonOptix). Data for >50 cells (each condition) stimulated at 0.5 Hz (25° C.) are summarized in Table 14, which shows AV-R1R2 transfection increased shortening ~50% and the rate of shortening and relaxation by ~100%, without affecting Ca2+ transient amplitude or basal levels. This suggests enhanced contraction is primarily due to an effect on myofilaments. While R1R2 over-expression did not alter the Ca2+ transient magnitude, the time to 50% (DT50) and 90% (DT90) decay shortened, suggesting enhanced SR Ca2+ reuptake or Na+/Ca2+ exchanger (NCX)-mediated efflux. These results were consistent at 1 and 2 Hz stimulation as well.

TABLE 14

R1R2 over-expression enhances cardiomyocyte contractility.

| Table 1 | Fractional Shortening (%) | Maximal Shortening Rate (μm/s) | Maximal Relaxation Rate (μm/s) | $RT_{50}$ (ms) | $RT_{90}$ (ms) | Minimal $Ca^{2+}$ (Fura ratio) | Maximal $Ca^{2+}$ (Fura ratio) | $DT_{50}$ (ms) | $DT_{90}$ (ms) |
|---|---|---|---|---|---|---|---|---|---|
| Non transduced | 6.2 ± 0.4 | 61.1 ± 4.4 | 46.8 ± 5.5 | 208 ± 28 | 330 ± 59 | 1.10 ± 0.02 | 1.22 ± 0.04 | 246 ± 26 | 665 ± 74 |
| Control (GFP) | 5.5 ± 0.5 | 56.5 ± 4.4 | 37.5 ± 4.3 | 202 ± 25 | 518 ± 42* | 1.12 ± 0.00 | 1.25 ± 0.04 | 297 ± 2.4 | 893 ± 63* |
| R1R2 (GFP) | 8.9 ± 0.5* | 109.6 ± 8.7* | 117.9 ± 13.1* | 113 ± 7*† | 265 ± 23† | 1.14 ± 0.02 | 1.23 ± 0.03 | 163 ± 10*† | 435 ± 34*† |

\* = p < 0.05 compared to No Treat,
† = p < 0.05 compared to GFP,
‡ = p < 0.05 compared to 0.5 Hz for all groups.

Example 36

R1R2 over-expression 'rescues' contractility of cardiomyocytes from infarcted hearts. Myocardial infarction was induced in adult rats by ligation of the left descending coronary artery. Four weeks later, adult rat cardiomyocytes were cultured and then transfected with either AV-R1R2 or AV-GFP for 48 hours. Loss of function was confirmed via in vivo echocardiography prior to cell isolation (FIG. 34). FIG. 25 shows that compared with control cells (no infarct), cardiomyocytes from infarcted hearts had reduced shortening magnitude (A) and velocity (B), increased relaxation time (C) and a reduced Ca2+ transient amplitude (D).

These effects were rescued by AV-R1R2 transduction (Infarct+R1R2). Interestingly, R1R2-over-expression had no effect on Ca2+ transient magnitude in normal cardiomyocytes, but increased magnitude to control levels in infarcted cells. This suggests that R1R2 over-expression has a significant effect on SR Ca2+ storage and/or release in infarcted cells, and the mechanism behind this action warrants more detailed investigation, as proposed below.

Example 37

Figure 26A:
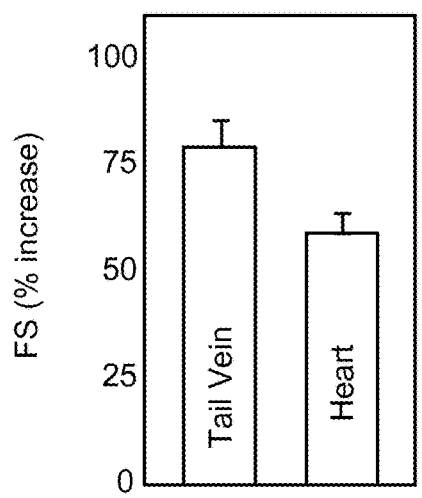
Figure 26B:
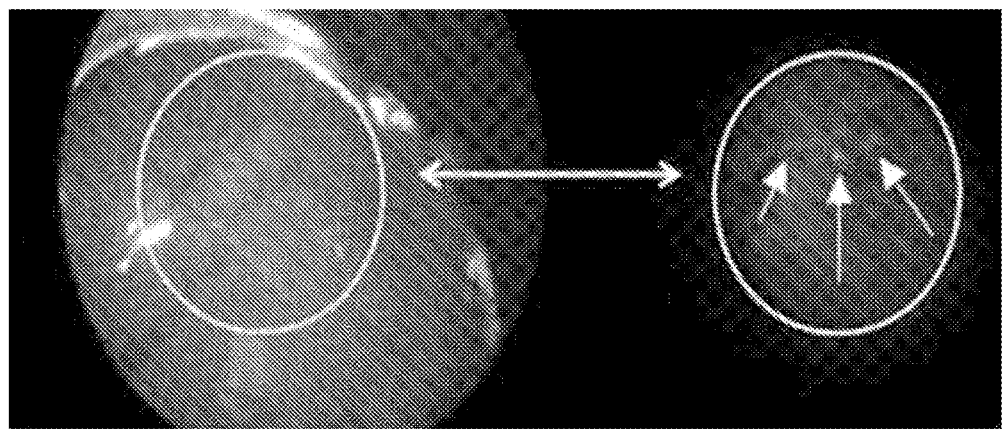

In vivo Studies. To determine how R1R2 over-expression affects cardiac function, we transfected C57/B16 mice by either tail vein or direct cardiac injections of adenoviruses—AV-R1R2(+GFP) or AV-GFP (only; control) (4-6 for each group). FIG. 26A shows that both methods resulted in increased left ventricular (LV) fractional shortening (FS) compared with control at 4 days post-injection. This increase was due to reduced LV inner diameter during systole, with no change for diastole, suggesting greater ventricular contraction (not ventricular dilation). FIG. 26B shows an injected LV, with the magnified region (right side) demonstrating localized transduction area (arrows) indicated by green fluorescence (from GFP). Significantly, even though small portions of hearts were transduced by direct injections, there was a large global increase in function (FIG. 26A, right bar).

We will determine in additional studies whether heart rate and/or stroke volume are affected. For the proposed studies, we will use FVB/N mice for all experiments, which is the background strain for the TG-R1R2 mice. We will also determine if there are long-term structural adaptations. Initial studies indicate that there are no gross cardiac morphological differences (heart weight:body weight ratio and ventricular thickness and mass are similar), but cellular hypertrophy, myofibrillar density, etc., have yet to be determined.

Example 38 dATP Diffusion through Myocardium May Increase Effectiveness of AAV6-R1R2 Transduction. With direct AV-R1R2 injections, it was surprising to observe large increases in FS despite a small area of AV-R1R2 transduction (<1% LV volume was GFP+). This suggests a small population of cardiomyocytes were over-expressing R1R2, and the resultant dATP had diffused through gap junctions into non-transduced cells, resulting in a more global increase in contractility. The diffusion of ATP through gap junctions has been reported by others[33, 34]. To test this idea, we injected fluorescein-tagged dATP into cultured hESC cardiomyocytes and saw diffusion over time into surrounding cells (FIG. 35A, B). Post-fix cell staining was connexin43 positive, which is evidence for gap junction coupling. We are continuing these studies to provide quantitative analysis of diffusion and to demonstrate that blocking gap junctions also blocks the transfer of dATP. We have also co-cultured AV-R1R2 transduced (dATP donor) human embryonic stem cell derived cardiomyocytes (hESC-CMs) and non-transduced (recipient) hESC-CMs. Non-transduced cells were dissociated and co-cultured with one of the virally transduced cohorts. At 48 hours following transduction, the co-cultures were imaged and contractile parameters were assessed by video microscopy (IonOptix,). FIG. 35C shows both AV-R1R2-transduced myocytes ("dATP donor cells", blue trace) and the GFP-null myocytes that were co-cultured with them ("WT dATP recipient cells", red trace) had significantly greater cell shortening than those in either AV-GFP-transduced myocytes ("control donor cells", green trace) or their GFP-null partners ("control recipient cells", black trace). This demonstrates R1R2-over-expressing dATP donor cells can enhance the contractile properties of coupled recipient cardiomyocytes. The data thus far are sufficiently compelling to suggest significant improvement in cardiac function may not require a high degree of R1R2 transduction of cells/tissue throughout the heart.

Example 39

Preliminary ex vivo heart function. Isovolumic contractile function was recorded during Langendorff perfusion for one WT and one TG-R1R2 mouse heart. LV pressure development was increased with increases in LV volume for both WT and TG-R1R2 hearts, indicative of normal Frank-Starling responsiveness. However, LV pressure development was elevated in the TG-R1R2 heart at all LV volumes (FIG. 28A), confirming increased pump function that was indicated by increased FS in TG-R1R2 animals (FIG. 27).

LV pressure development was slightly blunted in the TG-R1R2 heart in response to an increase in [Ca2+] from 2 mM to 4 mM (FIG. 28B) but remained elevated over the WT heart for the time course duration.

Example 40

31P NMR data. Simultaneously with the functional measurements, myocardial high energy phosphate content (phosphocreatine, ATP, and $P_i$) was determined by 31P NMR spectroscopy during baseline perfusion and with high [Ca2+] challenge. NMR spectra (FIG. 29) are shown for the WT (A) and the TG-R1R2 (B) hearts. In these spectra, the bottom trace is at baseline, the middle trace is at 10 minutes, and the top trace is 20 minutes, after onset of high [Ca2+] challenge. Importantly, ATP:heart weight ratio at baseline was the same between the WT and TG-R1R2 hearts (FIG. 29C, inset) and did not change throughout the high [Ca2+] challenge. While the phosphocreatine (PCr) to ATP ratio (FIG. 29C) was slightly lower at baseline in the TG-R1R2 mouse, there was no difference after high [Ca2+] challenge. This was primarily due to a decrease in the PCr/ATP ratio in the WT mouse, while in the TG-R1R2 mouse the PCr/ATP ratio was maintained. This is especially interesting in that the TG-R1R2 heart generated much higher LV pressures than the WT heart, even at 20 minutes post high [Ca2+] challenge, where the PCr/ATP ratios match. We will confirm and expand on these observations for acute and chronic R1R2 over-expression, and following myocardial infarction +/−R1R2 over-expression.

Example 41

Tissue specific targeting with AAV6 constructs. Tissue specificity was assessed using alkaline phosphatase driven by various gene promoters in AAV6 constructs. Table 15 compares two cardiac specific promoters (creatine kinase 7 (CK7) and cardiac troponin T (cTnT455)) to the non-specific cytomegalovirus (CMV) promoter, with values normalized to CK7 in the tibialis anterior (TA). Most importantly, cTnT455 leads to high expression in the heart, but little to no expression in other tissue. This specificity greatly reduces potential for effects of R1R2 over-expression in non-cardiac tissues.

dATP has no affect on mouse aortic smooth muscle force development. To begin studying potential systemic effects of elevated dATP, we collaborated with Dr. Frank Brozovich (Mayo Clinic) to determine if dATP affects mouse aortic smooth muscle contraction. FIG. 30A shows that back to back contractions in skinned muscle strips did not differ for dATP vs. ATP as the contractile substrate, and the data for multiple experiments is summarized in FIG. 30B. Additionally, control measurements demonstrated that dATP did not change the level of myosin light chain phosphorylation, which controls smooth muscle myosin binding to actin (data not shown).

TABLE 15

R1R2 over-expression enhances cardiomyocyte contractility.

| Table 2 | CK7 | CMV | cTnT455 |
|---|---|---|---|
| TA | 1 | 3.1 | 0 |
| Heart | 1.9 | 5.1 | 1.6 |
| Lung | 0.02 | 0.09 | 0.01 |
| Liver | 0.02 | 0.09 | 0.004 |
| Aorta | 0.01 | 0.13 | 0.005 |

Example 42

AAV6-R1R2 for Cardiac-Specific Targeting. We used rAAV6 vectors to acutely increase cardiac levels of R1R2 (and [dATP]). Production of rAAV6 vectors was as previously described[24]*. Briefly, plasmids are produced with recombinant AAV genomes containing a cardiac specific promoter (cTnT455). R1R2 transgene expression cassettes are co-transfected into HEK293 cells with a packaging/helper plasmid pDGM6 by CaPO4 precipitation methodology. Vectors are collected from culture, freeze-thawed, and the supernatant collected. Affinity purification uses a HiTrap heparin column (GE Healthcare, Piscataway, N.J.). The virus is concentrated on a sucrose gradient (40%), spun at 27,000 rpm (18 hours, 4° C.), and resolubilized in Hanks balanced solution. Vector genomes are determined relative to plasmid standards using a SV40 poly adenylation region oligonucleotide 32P end-labeled probe with Southern blot hybridization and confirmed by qPCR.

Selection of the cardiac targeting construct was assessed using alkaline phosphatase driven by various gene promoters in AAV6 constructs. Table 15 compares two striated muscle specific promoters (creatine kinase 7 (CK7) and cardiac troponin T (cTnT455)) to the non-specific cytomegalovirus (CMV) promoter, with values normalized to CK7 in the tibialis anterior (TA). Most importantly, cTnT455 leads to high expression in the heart, but little to

TABLE 15

Comparison of CK7, CMV, and cTnT455 promoters

| Table 3 | CK7 | CMV | cTnT455 |
|---|---|---|---|
| TA | 1 | 3.1 | 0 |
| Heart | 1.9 | 5.1 | 1.6 |
| Lung | 0.02 | 0.09 | 0.01 |
| Liver | 0.02 | 0.09 | 0.004 |
| Aorta | 0.01 | 0.13 | 0.005 | no expression in other tissue, thus greatly reducing potential for effects of R1R2 over-expression in non-cardiac tissues. FIG. 36A shows preliminary western blot evidence for this, where heart tissue from a AAV6-R1R2$^{cTnT455}$ injected (4.5 $e^{13}$) mouse expressed high R1 & R2 subunits compared to control mouse heart. Note that upper bands are non-specific staining, with arrows pointing to R1 and R2 protein (identified by molecular weight markers (not shown)). Importantly R1 & R2 expression in lung was extremely low in comparison with heart and was not changed in skeletal muscle. This is demonstrated in FIG. 36 for heart tissue from non-injected (B) vs. AAV6-alkaline phosphatase (purple; C) injected mice[36], suggesting AAV6-R1R2$^{cTnT455}$ should provide stable, long-term R1R2 over-expression. Stable AAV6 transgene expression has also been shown to persist for 12+ weeks in rat[37] and at least 6+ months in dogs[38].

Thus, we have begun studies to determine the relationship between AAV6-R1R2$^{cTnT455}$ injection dose, time course and stability of increased LV pump function, cardiac tissue R1R2 levels and [dATP]. FIG. 37 shows the effect of 3 vector doses, i.e. 1.5 $e^{13}$, 4.5 $e^{13}$, and 1.35 $e^{14}$ AAV6-R1R2$^{cTnT455}$ vector genomes or saline (control) injected into 3 month old mice (n=6 per group) on LV function. LV fractional shortening (FS) is significantly increased at the high dose after one week and at all doses after two weeks, with equivalent effects by 6 weeks. The magnitude increase in FS is ~25-50%, indicating the effect achievable with relatively low vector dose.

Example 43

Transgenic R1R2 over-expression Mice (TG-R1R2). We will utilize bi-transgenic mice that over-express both subunits (Rrm1 & Rrm2) of RR. FIG. 32 demonstrates over-expression of both subunits in cardiac muscle, with densitometric calculation values for these TG-R1R2 mice that are 33.7±7.6 (Rrm1) and 23.7±3.4 (Rrm2) fold greater than corresponding values for wild type (WT) mice[25,26]*. Note that for Rrm2 the upper band (*) is non-specific. The endogenous Rrm2 protein is not detectable in WT tissue, but in TG-R1R2 mice it appears as the band below the background band. While dATP levels for cardiac tissue have not yet been assessed [dATP] is increased ~10-fold in skeletal muscle which had corresponding 3.3±2.1 (Rrm1) and 35.7±11.1 (Rrm2) fold increases in the enzyme subunits. Interestingly, this magnitude of increase in dATP is similar to what we have determined for cardiomyocytes transfected with AV-R1R2 in culture (FIG. 23). Preliminary echocardiography of these TG-R1R2 mice at 6-8 months of age (measured on 3 successive weeks) revealed an average >50% increase in fractional shortening (FS) and a 15% reduction in diastolic LV inner diameter (LVIDd). As shown in FIG. 27, these differences (from WT controls) are similar in magnitude to values for the preliminary AV-R1R2 injection experiments.

Example 44

We will determine the acute effects of elevated cellular R1R2 and [dATP] on cardiac function. We expect that acute R1R2 over-expression (via AAV6-R1R2 vectors) will increase [dATP] in mouse hearts, resulting in increased systolic and diastolic function. This will be reflected in 1) increased cardiomyocyte and myofibril contraction with faster relaxation (due in part to increased crossbridge cycling kinetics), 2) an increase in basal cardiac metabolism without compromising energetic reserves, and 3) no change or a decrease in action potential duration (due to enhanced Ca2+ sequestration).

We will transfect normal adult FVB/N mice via tail vein or intraocular orbit injection with AAV6-R1R2 vectors with the cardiac specific promoter cTnT455 (as described above) with sham injections and with AAV6 containing only cTnT455 as controls. Following injection, echocardiography will be performed weekly (out to 6 weeks) to determine the optimal (maximal effect) time point for further assessments. Initial studies will characterize cardiac function in vivo with echocardiography, followed by in situ hemodynamic measures, or ex vivo using Langendorff perfused hearts for energetic studies and a working heart apparatus to assess pump performance. At selected time-points, other mice will be euthanized and hearts dissected for intact or skinned trabeculae preparations, isolated cardiomyocytes, myofibril preparations, protein analysis, and (immuno)histology. These measurements will provide detailed molecular mechanisms for alterations in cardiac function with acute R1R2 over-expression.

Example 45

Multi-scale mechanical measurements of whole organ. Echocardiography (GE Vivid7) will be done on all animals. Parasternal long axis images will be used to determine flow velocity across the left ventricular (LV) outflow tract and the outflow tract cross sectional area (CSA), to calculate stroke volume (SV=CSA×time velocity integral (area of the aortic flow velocity)) and cardiac output (CO=SV×heart rate)[31]*. Short axis 2-D views at the mid-ventricular (papillary muscle) level will be used to generate M-mode measurements of LV end-systolic (LVESD) and end-diastolic (LVEDD), anterior and posterior wall (PW) dimensions. These will be used to calculate fractional shortening [(LVEDD−LVESD)/LVEDD×100%] and LV wall mass [1.05(IVS thickness+LVEDD+PW thickness)][32,33]*. Some animals will undergo real-time assessment of cardiac contractility (Frank-Starling & pressure-volume relations) using miniaturized impedance/micromanometer catheters (Millar Instruments). Measures will include heart rate, end diastolic and systolic pressures, +dP/dt, −dP/dt, pressure recruitable stroke work (i.e., slope of stroke work (SW) vs. end diastolic volume (EDV)), end-systolic pressure-volume relationship and the time constant (Tau) of ventricular pressure decay. These parameters can be compared with in vitro working heart measurements, trabeculae and myofibril measurements in studying the dynamics of loaded cardiac contraction/relaxation. Both protocols will be performed in the absence/presence of dobutamine to assess potential changes in adrenergic responsiveness with acute R1R2 over-expression. Other animals will undergo in vitro Neely working heart measurements (Experimentria), free of potentially confounding hormonal fluctuations, to provide further information on preload/afterload, and adrenergic, responsiveness. Hearts will then be taken for gravimetric analysis, fixed, embedded and stained (H&E, Masson's Trichrome, Picrosirius Red) according to well-established procedures[27,68]*. Sections will be evaluated for hypertrophy, dilation, and fibrosis[11,34]*. Serial sections of hearts will undergo immunohistochemistry to assess R1R2 expression and percent transduced cardiomyocytes to correlate with in vivo and in vitro function.

Example 46

Multi-scale mechanical measurements of trabeculae, cardiomyocytes and myofibrils. For different groups of mice, following endpoint echocardiography, hearts will be excised and ventricles will be prepared for either 1) dissection of intact or skinned trabeculae, 2) cardiomyocytes in culture, or 3) myofibril preparations.

Trabeculae. We will determine how R1R2 over-expression affects contraction of intact trabeculae under external load at varied sarcomere lengths (SL), as occurs in vivo. Thin (<120 μm diameter, ~50 μm depth) trabeculae will be mounted between a force transducer and linear motor in an oxygenated perfusion chamber containing stimulating electrodes[35-37]*. Isometric twitch force, twitch kinetics and Ca2+ transients (fura-2), and their SL dependence (Frank-Starling relationship, SL=1.9 vs. 2.2 μm) will be measured under the same protocols as for isolated cardiomyocytes, with a standard Krebs-Henseleit solution, 95/5% $O_2/CO_2$ at 37° C. 38. Demembranated trabeculae will be used to assess steady-state myofilament contraction, with fine control of [Ca2+], [dATP], and [ATP], to determine if acute R1R2 over-expression alters myofilament contraction independent of [dATP], via protein isoform or phosphorylation changes.

Isolated Adult Ventricular Cardiomyocytes. Isolated mouse cardiomyocytes allow for high throughput, simultaneous assessments of contraction cycles and SR function at varied stimulation frequencies[7]*. As such, cardiomyocyte Ca2+ transients (fura-2) and shortening/relaxation (length and sarcomere length) will be monitored at 0.5, 1, 2 and 3 Hz using video microscopy (IonOptix, Milton, Mass.). We will measure before and after 1) varying extracellular

[Ca2+]([Ca2+] ext), to assess Ca2+ induced Ca2+ release (CICR), 2) myofilament crossbridge inhibitors (BDM, blebbistatin, etc.), to determine the influence of contractile activity on SR function, and 3) adrenergic challenge (α-(phenylephrine) or β(isoproterenol)), to determine if responsiveness (shortening, Ca2+ release/reuptake) is altered. Detailed methods to measure action potential (AP) properties, CICR, SR Ca2+ ATPase (SERCA), NCX, and plasmalemmal Ca2+ ATPase function are as described below.

Myofibrils. The kinetics of contractile activation and relaxation are important in determining normal cardiac function. During systole, rapid ventricular pressure development is critical for effective blood ejection (working stroke), and during diastole ventricles must relax rapidly to allow sufficient ventricular filling. These properties are often altered in cardiac disease. The ms timescale kinetics of myofiber contraction and relaxation are difficult to assess in skinned trabeculae, where large diffusion distances slow [Ca2+] equilibration during solution changes. Myofibril preparations have small diffusion distances, allowing rapid solution switching and force measurements, independent of intact cell Ca2+ transients. This approach has been used previously[39,40]* and new instrumentation allows for measuring single myofibril force development and relaxation in a single protocol (FIG. 33). These measures are relevant for isovolumetric (isometric) phases of systole (kact) and diastole (kREL). Importantly we can monitor both the slow (kREL, slow) and rapid (kREL, fast) phases of relaxation. The kREL, slow and duration (tREL, slow) are thought to reflect crossbridge detachment rates[41]* which previous studies show is faster with dATP 1, 5. Thus, we will compare activation and relaxation kinetics between AAV6-R1R2 transfected and control hearts using either ATP or dATP (or varied ATP:dATP ratios). ATP-only myofibril experiments allow us to assess if R1R2 over-expression alters myofilament contractile properties per se, while measures with dATP will allow determination of the crossbridge component of faster relaxation seen with R1R2 over-expression in cardiomyocytes vs. control cells. Myofibril studies also allow independent control of [ADP], [Pi], [Ca2+], pH and myofilament protein phosphorylation (kinases, phosphatases), all conditions that vary in the heart, correlate with metabolic behavior, but are difficult to control in intact cardiac preparations.

Example 47

Electrophysiological Measurements and Ca2+ Handling. Electrophysiology will be assessed in cells maintained at 37° C. and stimulated between 1-5 Hz using routine techniques[34,42-48]*. APs will be recorded as previously described, using a HEKA EPC-10 amplifier operated in current-clamp mode. (The EPC-10 has a true voltage-follower circuit similar to a classic microelectrode amplifier[49,50]*). To prevent dialysis of intracellular nucleotides, we will use the perforated patch-technique (which allows the passage of monovalent ions but not molecules larger than ~200 daltons[51]*) and will include a dye in the pipette solution to notify us if whole-cell rupture occurs (after Strauss et al.[52]*). AP parameters to be assessed include upstroke velocity, APD (at 50, 70, and 90% repolarization), AP amplitude, maximum diastolic potential, and frequency of after-depolarizations. For $[Ca2+]^i$ imaging experiments, cells will be loaded with fura-2 or fluo-4-AM, and then imaged using either an Ionoptix CCD-based system or a Zeiss LSM5 10 META confocal system operated in line-scan mode. Calibration of fluorescence signals will be performed using either the "pseudo-ratio"[53]* or Fmax[54]* methods. Note that the whole-cell $[Ca2+]_i$ transient is comprised of Ca2+ influx, the subsequent activation of SR Ca2+ release (i.e., Ca2+ sparks), and Ca2+ clearance mechanisms (primarily NCX and SERCA). Thus, to understand the mechanisms underlying changes in the $[Ca2+]_i$ transient, one must examine these fluxes separately. Ca2+ influx via the L-type Ca2+ current (ICa) will be measured under voltage-clamp, using Na+-free solutions to eliminate NCX function[55]*. To look for effects on SR Ca2+ release, we will use two standard methods: 1) simultaneous measurements of voltage-dependent ICa and $[Ca2+]_i$ transients to determine the EC-coupling gain factor[56,57] and 2) fast confocal imaging of localized release events (i.e., Ca2+ sparks)[57]*. SR Ca2+ load will be measured using the caffeine technique[58,59]*. To screen for effects on NCX or SR Ca2+ ATPase function, we will use standard inhibitors and conditions to isolate each flux and examine the kinetics of AP- and caffeine-induced [Ca2+]i transient, and NCX currents[57,60-62]*.

Example 48

Myocardial Energy Metabolism. Metabolism and contraction will be simultaneously assessed using multi-nuclear NMR spectroscopy in isolated perfused hearts as previously described[63,64]*.

NMR spectroscopy. Excised mouse hearts will be perfused at constant pressure (80 mm Hg) at 37° C. as previously described[63]*. A water-filled balloon will be inserted into the LV, adjusted to an end-diastolic pressure of 5-10 mm Hg, and used to record LV pressure and heart rate. Isovolumic contractile function will be calculated as LV developed pressure times heart rate (rate-pressure product; RPP). MVO2 is determined by measuring coronary flow rate and the PO2 difference between perfusate and pulmonary outflow tract effluent. To elicit high contractile performance, the perfusate [CaCl2] will be increased from 2 to 4 mM. $^{31}P$ NMR spectra will be collected at baseline and during high workload challenge for 25 minutes, then freeze clamped with liquid nitrogen cooled Wollenberger tongs. Relative oxidation of carbon substrates will be determined for mitochondria by perfusing hearts with 13C-labeled substrates followed by freeze-clamping. 13C NMR spectroscopy and isotopomer analysis will be performed using tissue extracts as previously described[63,64]*.

HPLC Calibration of 31P NMR Spectra. Freeze-clamped tissues will be used to determine the myocardial content of ATP by HPLC as reported previously[65]*. Myocardial ATP content obtained by HPLC is converted to [ATP] assuming an intracellular water content of 0.48 mL/g and a protein content of 0.15 g/g blotted wet tissue. Values will be used to calibrate ATP peak areas in baseline $^{31}P$ NMR spectra for the respective groups. The area of the γ-ATP peak obtained under baseline conditions will be set to 100% and used as the reference value for all peaks in all 31P NMR spectra.

Mitochondrial Biogenesis and Function. Mitochondrial respiration assays will be performed using isolated mitochondria and permeablized myofibers or myocytes with pyruvate/malate (Complex I), succinate (Complex II) and palmitoyl-carnitine in the presence or absence of ADP, respiratory uncoupler (FCCP) and a variety of inhibitors[66,67]*. ATP synthesis rate in beating hearts will be assessed using $^{31}P$ NMR magnetization transfer and compared to the estimation by $MVO_2$[63]*. Mitochondria density will be assessed by EM images, and the activity or expression of key mitochondrial enzymes/proteins, (citrate synthase, COX, aconitase and VDAC) will be determined. The mtDNA content and its replication as well as the transcriptional mechanisms involved in mitochondrial biogenesis will be determined as described[68*].

Myofilament and SR Protein Profiling. Changes in contractile function, Ca2+ transients, SR spark activity and/or Ca2+ load under all conditions will be correlated with isoform, abundance and phosphorylation of myofilament proteins (cTnI, cTnT, MLC-2, cMyBP-C and Tm), SR proteins (PLB, RyR), and sarcolemmal proteins (NCX, PMCA, L-type Ca2+ channel). Changes in mRNA and protein expression will be determined using RT-PCR and western blot analysis. SR protein fractions will be prepared according to published methods[53-56]. If electrophysiological measurements indicate changes, we can assess ion channels with specific antibodies. Analysis of R1R2 expression will be made via western blots (FIG. 23) or immunohistochemistry and correlated with experimental endpoints. Specificity of the cTnT455 promoter will be assessed by determining R1R2 expression in non-cardiac tissues such as skeletal muscle and lung. Phosphorylation will be profiled using Pro-Q diamond (with Sypro Ruby protein stain) and western blot analysis. For site specific serine and threonine residue phosphorylation, we can perform mass spectrometry.

Example 49

These systematic studies outlined in Examples 43 to 48 will produce detailed multi-scale information on how short-term R1R2 over-expression and increased [dATP] influences contractile properties, and Ca2+ and energetic homeostasis. We expect relatively low doses of AAV6-R1R2 may be sufficient to potentiate function at all levels of mechanical assessment. We expect these mice will maintain or have enhanced cardiac β-adrenergic responsiveness. This could occur if enhanced myocardial function (via [dATP]) reduces need for β-adrenergic drive. Furthermore, we expect this adaptation to be more prominent at longer time points (3-4 weeks), following the peak of R1R2 over-expression, then decline as transduction decays. The peak of adaptation may approach the long-term changes we expect in TG-R1R2 animals. Functional effects of post-translational protein modifications, resulting from increased [dATP], will be assessed in cellular/subcellular assays using ATP as the substrate. This could result in increased myofilament Ca2+ sensitivity (demembranated trabeculae), increased kinetics of activation and relaxation (myofibrils), and increased kinetics of Ca2+ reuptake (intact trabeculae/cardiomyocytes). However, we don't expect the Frank-Starling relationship to be blunted either in vivo or in vitro with R1R2 over-expression, as indicated by the preliminary results (FIG. 28). We expect R1R2 over-expression to increase twitch force in intact cardiac trabeculae, indicative of increased Ca2+ sensitivity, and similar to the increase in fractional shortening observed in isolated cardiomyocytes. Likewise, we expect the Ca2+ transient to be of similar magnitude to untreated trabeculae, but there may be faster Ca2+ decay in R1R2 over-expressing trabeculae, and a concomitant increase in force relaxation. Demembranated trabeculae from R1R2 over-expressing myocardium may exhibit small increases in Ca2+ sensitivity even with ATP as the contractile substrate, which would reflect a decrease in sympathetic tone and subsequently lower phosphorylation of cardiac troponin I and myosin binding protein-C. We expect no overt changes in Ca2+ handling other than a faster Ca2+ transient decay, similar to that observed in in vitro AV-R1R2 transfected cardiomyocytes. Faster Ca2+ transient decay may arise from 1) increased sarcomere shortening coupled with faster crossbridge detachment leading to progressively increased thin filament Ca2+ dissociation, thus making Ca2+ available for re-sequestration sooner than in control myocytes, and 2) changes to Ca2+ handling proteins (SERCA:phospholamban ratio, phospholamban and/or plasma membrane Ca2+ ATPase phosphorylation), or Ca2+ ATPase pumps using dATP as an energetic substrate, that increase Ca2+ sequestration. We do not expect large changes in metabolic behavior with acute R1R2 over-expression, based, in part, on preliminary data (FIG. 29), where steady state high energy phosphate content is minimally affected in the TG-R1R2 heart despite increased contractile function.

Example 50

We will determine the chronic effects of elevated cellular R1R2 and [dATP] on cardiac function. We expect that TG-R1R2 mice will adapt to increased systolic function with decreased β-adrenergic drive, and diastolic function will be maintained by adaptation of Ca2+ handling mechanisms. This will be reflected in 1) increased cardiomyocytes contraction with minimal change in relaxation, 2) an adaptation of cardiac metabolism so it is not elevated over wild type controls, 3) no change in excitation-contraction coupling, and 4) increased responsiveness to β-adrenergic stimulation.

To study chronic R1R2 over-expression, we will employ a bi-transgenic mouse model (TG-R1R2) that expresses high levels of both ribonucleotide reductase subunits throughout life. We will begin by studying adult mice at 6 months of age. To determine progression of altered function and/or adaptation over time young mice will be monitored with echocardiography up to 6 months of age. From these measures we will determine earlier time points to study. At these time points, we will make all the experimental assessments as outlined above. These multi-scale measurements will provide detailed molecular mechanisms for adaptations in cardiac function with chronic R1R2 over-expression, as well as comparisons with experiments described above.

These studies will provide detailed information about long term cardiac adaptation to R1R2 over-expression in vivo where intrinsic adaptation is subject to constant paracrine and hormonal fluctuations. We expect R1R2 over-expression may increase β-adrenergic responsiveness through adaptation to greater baseline contractility, which does not occur with short-term R1R2 over-expression. Blunting of the Frank-Starling relationship is not expected either in vivo or in vitro with R1R2 over-expression, as indicated by preliminary results (FIG. 28) and because SL dependence of contractile activation is maintained with dATP[3*]. Cardiac output may be maintained by decreased heart rate (less β-adrenergic drive) to compensate for increased stroke volume (due to dATP). We also don't expect to find a hypertrophic or dilated ventricular functional and morphological phenotype in TG-R1R2 mice, and preliminary evidence suggests this does not occur. We expect SR Ca2+ loading to be maintained, such that increased LV function is primarily from enhanced myofilament activity. If SR Ca2+ pump activity is chronically increased, resulting in faster Ca2+ transient decay, it should result in shorter APD. We expect energetic reserves (PCr, ATP) to be maintained and a similar, but elevated response to high Ca2+ challenge and that mitochondrial function will be slightly elevated by increased myosin utilization of ATP and dATP. In summary we expect an elevated baseline function, but maintenance of ability to respond to increased demand, with minimal adaptation of Ca2+ handling and energetic homeostasis.

Example 51

We will determine the effects of elevated cellular R1R2 and [dATP] on cardiac function of infarcted hearts. Acute R1R2 over-expression and increased [dATP] are expected to improve cardiac performance and, at least temporarily, halt progression to heart failure in infarcted hearts. Promising preliminary evidence, where AV-R1R2 transduction rescued the depressed contractile and Ca2+ transient behavior of cultured cardiomyocytes from infarcted rat hearts (FIG. 25), suggests this may be possible. Increasing the contractile capacity of myofilaments should improve cardiac function, thus reducing chronic β-adrenergic signaling and PKC-mediated phosphorylation associated with progression to heart failure. It will be interesting to see if a temporary gain in function (via one dose of AAV6-R1R2) will lead to adaptations that allow sustained improvement. It is also known that the failing heart is "energy-starved"[69]*. Numerous clinical studies have shown heart failure is worsened by energy costly therapies, such as adrenergic receptor agonists, and improved by energy saving therapies such as ACEI and beta-blockade. It is critically important that increasing dATP does not negatively impact myocardial energetics. Thus, it is exciting that preliminary data showed no change of high energy phosphate content at higher contractile function. We will determine whether this is the case for infarcted hearts where impaired energy metabolism has been repeatedly observed.

We will study the effects of acute R1R2 over-expression on infarcted hearts using AAV6-R1R2. Myocardial infarction is achieved by permanent ligation of the left descending coronary artery. In rats, this typically results in infarct zones measuring ~20-35% of the LV free wall cross-section area (10-15% of total LV area) with reduced fractional shortening, systolic and diastolic ventricular dilation (FIG. 34A-C) and loss of responsiveness in working hearts to increased pre-load (FIG. 34D).

Data from an in vivo study supports earlier studies with cultured cardiomyocytes. In the study, rats were directly injected in the heart with AAV6-R1R2 (as described above) on the fifth day post-infarct. Echocardiography was performed (up to 8 weeks) post-transduction and the results shown in FIG. 38. At one week after injection, FS was already improved and by 2 weeks, FS was the same for the infarct+vector as it was for sham operated (no infarct) hearts. This recovery persisted to 8 weeks, when we stopped the experiment, demonstrating the improvement in cardiac function in infarcted hearts with administration of AAV6-R1R2.

To determine if acute R1R2 over-expression helps prevent loss of LV function, separate animals will be transfected with AAV6-R1R2 1-2 weeks prior to infarct surgery. For both protocols, some mice or rats will be taken for in situ hemodynamic properties via Millar catheter experiments (see above). Additional animals will be used for in vitro studies on working heart, intact and skinned trabeculae, cultured cardiomyocytes and isolated myofibrils. As outlined above, we will determine which preparations are the most instructive and focus the majority of measurements on them to limit the number of animals required for these studies. Some dissected hearts will be weighed, fixed, embedded and stained, and evaluated for hypertrophy and fibrosis (as above). Serial sections will undergo immunohistochemistry to assess R1R2 expression and penetrance to correlate with changes in in vivo and in vitro function.

We expect that R1R2 over-expression and increased [dATP] will improve cardiac performance of infarcted hearts at the selected time point for analysis. Response to high Ca2+ challenge, β-adrenergic stimulation and increasing pre-loads will be improved. In vitro Neely working heart measurements of the hearts assessed in FIG. 38 showed a loss of pre-load responsiveness of hearts (heart failure) that have been infarcted (no treatment), but a recovery of pre-load responsiveness of the infarcted hearts receiving the vectors to the level of control, uninfarcted hearts, thereby demonstrating a restoration of cardiac function. See FIG. 39, where power is given in units of g·cm/min. The effect may have occurred by lessening chronic β-adrenergic stimulation (which can be assessed by monitoring plasma hormones). This should be reflected in the multi-scale analysis as improved 1) Ca2+ transients, 2) myofilament contraction and relaxation magnitude and kinetics, and 3) energetic profile. We would also expect to see a difference between treated and untreated hearts in α- and β-adrenergic mediated cardiomyocyte protein phosphorylation.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

REFERENCES

1. De tombe P P. Altered contractile function in heart failure. Cardiovascular Research. 1998; 37(2):367-380.
2. Rubart M, Zipes D P. Mechanisms of sudden cardiac death. J Clin Invest. 2005; 115(9):2305-2315.
3. Sabbah H N. Biologic rationale for the use of beta-blockers in the treatment of heart failure. Heart Fail Rev. 2004; 9(2):91-97.
4. Kass D A, Solaro R J. Mechanisms and use of calcium-sensitizing agents in the failing heart. Circulation. 2006; 113(2):305-315.
5. Wyskovsky W, Hauptner R, Suko J. Drug-induced calcium release from heavy sarcoplasmic reticulum of skeletal muscle. Biochim. Biophys. Acta. 1988; 938:89-96.
6. MacGowan G A. The myofilament force-calcium relationship as a target for positive intropic therapy in congestive heart failure. Cardiovasc Drugs Ther. 2005; 19(3): 203-210.
7. Moreno-Gonzalez A, Fredlund J, Regnier M. Cardiac troponin C (TnC) and a site I skeletal TnC mutant alter Ca2+ versus crossbridge contribution to force in rabbit skeletal fibres. J Physiol. 2005; 562(Pt 3):873-884.
8. Tikunova S B, Davis J P. Designing calcium sensitizing mutations in the regulatory domain of cardiac troponin C. J Biol Chem. 2004; 279(34):35341-35352.
9. Kreutziger K L, Piroddi N, Tesi C, Poggesi C, Regnier M. Cooperative activation and tension kinetics in cardiac muscle are strongly modulated by calcium binding kinetics of troponin C. Journal of Molecular and Cellular Cardiology. 2010; In press.

10. Santana L F, Kranias E G, Lederer W J. Calcium sparks and excitation-contraction coupling in phospholamban-deficient mouse ventricular myocytes. J Physiol. 1997; 503(1):21-29.
11. Moreno-Gonzalez A, Korte F S, Dai J, Chen K Y, Ho B, Reinecke H, Murry C E, Regnier M. Cell therapy enhances function of remote non-infarcted myocardium. Journal of Molecular and Cellular Cardiology. 2009; 47(5):603-613.
12. Herron T J, Vandenboom R, Fomicheva E, Mundada L, Edwards T, Metzger J M. Calcium-independent negative inotropy by beta-myosin heavy chain gene transfer in cardiac myocytes. Circ Res. 2007; 100(8):1182-1190.
13. Badrian B, Bogoyevitch M A. Changes in the transcriptional profile of cardiac myocytes following green fluorescent protein expression. DNA Cell Biology. 2007; 26(10):727-736.
14. Nishimura S, Nagai S, Sata M, Katoh M, Yamashita H, Saeki Y, Nagai R, Sugiura S. Expression of green fluorescent protein impairs the force-generating ability of isolated rat ventricular cardiomyocytes. Mol Cell Biochem. 2006; 286(1-2):59-85.
15. Herron T J, Devaney E, Mundada L, Arden E, Day S, Guerrero-Serna G, Turner I, Westfall M V, Metzger J M. Ca2+-independent positive molecular inotropy for failing rabbit and human cardiac muscle by alpha-myosin motor gene transfer. Faseb J. 2010; 24(2):415-424.
16. Feest E R, Tu A, Luo C, Nowakowski S G, Regnier M. Effect of varying mutant troponin C content on contractile properties of striated muscle. Biophys. J. 2009; 96(3): 228a.
17. Norman C, Rall J A, Tikunova S B, Davis J P. Modulation of the rate of cardiac muscle contraction by troponin C constructs with various calcium binding affinities. Am J Physiol Heart Circ Physiol. 2007; 293:H2580-H2587.
18. Baudenbacher F, Schober T, Pinto J R, Sidorov V Y, Hilliard F, Solaro R J. Myofilament Ca2+ sensitization causes susceptibility to cardiac arrythmia in mice. Journal of Clinical Investigation. 2008; 118(12):3893-3903.
19. Solaro R J, Gambassi G, Warshaw D M, Keller M R, Spurgeon H A, Beier N. Stereoselective actions of thiadiazinones on canine cardiac myocytes and myofilaments. Circ Res. 1993; 73(6):981-990.
20. White J, Lee J A, Shah N, Orchard C H. Differential effects of the optical isomers of EMD 53998 on contraction and cytoplasmic Ca2+ in isolated ferret cardiac muscle. Circ Res. 1993; 73(1):61-70.
21. Korte F S, Dai J, Weiss R, Vaziri C, Murry C E, Regnier M. Overexpression of cardiomyocyte ribonucleotide reductase (RR) increases contraction without affecting relaxation in adult cardiomyocytes from normal and infarcted hearts. Journal of Muscle Research and Cell Motility. 2010:abstract.
22. Lim C C, Yang H, Yang M, Wang C K, Shi J, Berg E A, Pimental D R, Gwathmey J K, Hajjar R J, Helmes M, Costello C E, Huo S, Liao R. A novel mutant cardiac troponin C disrupts molecular motions critical for calcium binding affinity and cardiomocyte contractility. Biophys. J. 2008; 94:3577-3589
23. Fentzke R C, Buck S H, Patel J R, Lin H, Wolska B M, Stojanovic M O, Martin A F, Solaro R J, Moss R L, Leiden J M. Impaired cardiomyocyte relaxation and diastolic function in transgenic mice expressing slow skeletal troponin I in the heart. J. Physiol. Lond. 1999; 517(1):143-157.
24. Preetha N, Yiming W, Helmes M, Fukuda N, Siegfried L, Granzier H. Restoring force development by titin/connectin and assessment of Ig domain unfolding. Journal of Muscle Research and Cell Motility. 2005; 26(307-317).
1. Ganguly P K, Pierce G N, Dhalla K S, Dhalla N S. Defective sarcoplasmic reticular calcium transport in diabetic cardiomyopathy. American Journal of Physiology. 1983; 244:E528-E535.
2. Sabbah H N. Biologic rationale for the use of beta-blockers in the treatment of heart failure. Heart Fail Rev. 2004; 9(2):91-97.
3. LeWinter M M. Functional consequences of sarcomeric protein abnormalities in failing myocardium. Heart Fail Rev. 2005; 10(3):249-257.
4. Palmer B M. Thick filament proteins and performance in human heart failure. Heart Fail Rev. 2005; 10(3):187-197.
5. Rubart M, Zipes D P. Mechanisms of sudden cardiac death. J Clin Invest. 2005; 115(9):2305-2315.
6. Regnier M, Rivera A J, Chen Y, Chase P B. 2-deoxy-ATP enhances contractility of rat cardiac muscle. Circ. Res. 2000; 86(12):1211-1217.
7. Regnier M, Martin H, Barsotti R J, Rivera A J, Martyn D A, Clemmens E. Cross-bridge versus thin filament contributions to the level and rate of force development in cardiac muscle. Biophys J. 2004; 87(3): 1815-1824.
8. Adhikari B B, Regnier M, Rivera A J, Kreutziger K L, Martyn D A. Cardiac length dependence of force and force redevelopment kinetics with altered cross-bridge cycling. Biophys J. 2004; 87(3):1784-1794.
9. Clemmens E W, Regnier M. Skeletal regulatory proteins enhance thin filament sliding speed and force by skeletal HMM. J Muscle Res Cell Motil. 2004; 25(7):515-525.
10. Schoffstall B, Clark A, Chase P B. Positive inotropic effects of low dATP/ATP ratios on mechanics and kinetics of porcine cardiac muscle. Biophys. J. 2006; 91(6):2216-2226.
11. Kashlan O B, Cooperman B S. Comprehensive model for allosteric regulation of mammalian ribonucleotide reductase: refinements and consequences. Biochemistry. 2003; 42(6):1696-1706.
12. Kashlan O B, Scott C P, Lear J D, Cooperman B S. A comprehensive model for the allosteric regulation of mammalian ribonucleotide reductase. Functional consequences of ATP- and dATP-induced oligomerization of the large subunit. Biochemistry. 2002; 41(2):462-474.
13. Santana L F, Kranias E G, Lederer W J. Calcium sparks and excitation-contraction coupling in phospholamban-deficient mouse ventricular myocytes. J Physiol. 1997; 503(1):21-29.
14. Moreno-Gonzalez A, Korte F S, Dai J, Chen K Y, Ho B, Reinecke H, Murry C E, Regnier M. Cell therapy enhances function of remote non-infarcted myocardium. Journal of Molecular and Cellular Cardiology. 2009; 47(5):603-613.
15. He T C, Zhou S, Da Costa L T, Yu J, Kinzler K W, Vogelstein B. A simplified system for generating recombinant adenoviruses. Proc Natl Acad Sci USA. 1998; 95:2509-2514.
16. Herron T J, Vandenboom R, Fomicheva E, Mundada L, Edwards T, Metzger J M. Calcium-independent negative inotropy by beta-myosin heavy chain gene transfer in cardiac myocytes. Circ Res. 2007; 100(8):1182-1190.
17. Badrian B, Bogoyevitch M A. Changes in the transcriptional profile of cardiac myocytes following green fluorescent protein expression. DNA Cell Biology. 2007; 26(10):727-736.

18. Nishimura S, Nagai S, Sata M, Katoh M, Yamashita H, Saeki Y, Nagai R, Sugiura S. Expression of green fluorescent protein impairs the force-generating ability of isolated rat ventricular cardiomyocytes. Mol Cell Biochem. 2006; 286(1-2):59-85.
19. Herron T J, Devaney E, Mundada L, Arden E, Day S, Guerrero-Serna G, Turner I, Westfall M V, Metzger J M. Ca2+-independent positive molecular inotropy for failing rabbit and human cardiac muscle by alpha-myosin motor gene transfer. Faseb J. 2010; 24(2):415-424.
20. Regnier M, Rivera A J, Chen Y, Chase P B. 2-deoxy-ATP enhances contractility of rat cardiac muscle. Circ Res. 2000; 86(12):1211-1217.
21. Schoffstall B, Clark A, Chase P. Positive inotropic effects of low dATP/ATP ratios on mechanics and kinetics of porcine cardiac muscle. Biophys J. 2006; 91(6):2216-2226.
22. Schoffstall B, Chase P. Increased intracellular [dATP] enhances cardiac contraction in embryonic chick cardiomyocytes. Journal of Cellular Biochemistry. 2008; 104(6):2217-2227.
23. Xu X, Page J L, Surtees J A, Liu H, Lagedrost S, Lu Y, Bronson R, Alani E, Nikitin A Y, Weiss R S. Broad overexpression of ribonucleotide reductase genes in mice specifically induces lung neoplasms. Cancer Res. 2008; 68(8):2652-2660.
24. Regnier M, Lee D M, Homsher E. ATP analogs and muscle contraction: mechanics and kinetics of nucleoside triphosphate binding and hydrolysis. Biophys J. 1998; 74(6):3044-3058.
25. Regnier M, Homsher E. The effect of ATP analogs on posthydrolytic and force development steps in skinned skeletal muscle fibers. Biophys J. 1998; 74(6):3059-3071.
26. Regnier M, Martyn D A, Chase P B. Calcium regulation of tension redevelopment kinetics with 2-deoxy-ATP or low [ATP] in rabbit skeletal muscle. Biophys J. 1998; 74(4):2005-2015.
27. Janssen P M, Periasamy M. Determinants of frequency-dependent contraction and relaxation of mammalian myocardium. J Mol Cell Cardiol. 2007; 43(5):523-531.
28. Bassani J W, Bassani R A, Bers D M. Relaxation in rabbit and rat cardiac cells: species-dependent differences in cellular mechanisms. J Physiol. 1994; 476:279-293.
29. Bers D M. Cardiac excitation-contraction coupling. Nature. 2002; 415:198-205.
30. Luo Y, Davis J P, Smillie L B, Rall J A. Determinants of relaxation rate in rabbit skinned skeletal muscle fibres. J Physiol. 2002; 545(Pt 3):887-901.
31. Luo Y, Davis J P, Tikunova S B, Smillie L B, Rall J A. Myofibrillar determinants of rate of relaxation in skinned skeletal muscle fibers. Adv Exp Med Biol. 2003; 538: 573-581.
32. Piroddi N, Belus A, Scellini B, Tesi C, Giunti G, Cerbai E, Mugelli A, Poggesi C. Tension generation and relaxation in single myofibrils from human atrial and ventricular myocardium. Pflugers Arch. 2007; 454(1):63-73.
33. Tesi C, Piroddi N, Colomo F, Poggesi C. Relaxation kinetics following sudden Ca(2+) reduction in single myofibrils from skeletal muscle. Biophys J. 2002; 83(4): 2142-2151.
34. Edman K A P. The velocity of unloaded shortening and its relation to sarcomere length and isometric force in vertebrate muscle fibers. J. Physiol. Lond. 1979; 291:143-159.
35. Hinken A C, McDonald K S. Inorganic phosphate speeds loaded shortening in rat skinned cardiac myocytes. American Journal of Physiology. 2004; 287:C500-C507.

1. Willott R, Gomes A, Chang A, Parvatiyar M, Pinto J, Potter J. Mutations in Troponin that cause HCM, DCM AND RCM: what can we learn about thin filament function?J Mol Cell Cardiol. 2010; 48(5):882-92.
2. Parvatiyar M, Pinto J, Liang J, Potter J. Predicting cardiomyopathic phenotypes by altering Ca2+ affinity of cardiac troponin C. J Biol Chem. 2010; 285(36):27785-97. PMCID: PMC2934646.
3. Sjaastad I, Wasserstrom J, Sejersted O. Heart failure—a challenge to our current concepts of excitation-contraction coupling. J Physiol. 2003; 546(Pt 1):33-47. PMCID: PMC2342477.
4. DiPaola N, Sweet W, Stull L, Francis G, Schomisch Moravec C. Beta-adrenergic receptors and calcium cycling proteins in non-failing, hypertrophied and failing human hearts: transition from hypertrophy to failure. J Mol Cell Cardiol. 2001; 33(6):1283-95.
5. Minamisawa S, Hoshijima M, Chu G, Ward C, Frank K, Gu Y, et al. Chronic phospholamban-sarcoplasmic reticulum calcium ATPase interaction is the critical calcium cycling defect in dilated cardiomyopathy. Cell. 1999; 99(3):313-22.
6. Kreutziger K L, Piroddi N, Tesi C, Poggesi C, Regnier M. Cooperative activation and tension kinetics in cardiac muscle are strongly modulated by calcium binding kinetics of troponin C. Journal of Molecular and Cellular Cardiology. 2010; Accepted with Revisions.
7. Korte F S, Murry C, Regnier M. Targeting Myofilaments To Improve Cardiomyocyte Contractile Properties in Heart Disease. Molecular Therapy. 2009; 17(S1):914a.
8. The World Health Report 2008: World Health Organization; 2008 Contract No.: Document Number|.
9. Tardiff J. Sarcomeric proteins and familial hypertrophic cardiomyopathy: linking mutations in structural proteins to complex cardiovascular phenotypes. Heart Fail Rev. 2005; 10(3):237-48.
10. Palmiter K, Tyska M, Haeberle J, Alpert N, Fananapazir L, Warshaw D. R403Q and L908V mutant beta-cardiac myosin from patients with familial hypertrophic cardiomyopathy exhibit enhanced mechanical performance at the single molecule level. J Muscle Res Cell Motil. 2000; 21(7):609-20.
11. Blanchard E, Seidman C, Seidman J, LeWinter M, Maughan D. Altered crossbridge kinetics in the alphaMHC403/+ mouse model of familial hypertrophic cardiomyopathy. Circ Res. 1999; 84(4):475-83.
12. Gomes A, Potter J. Molecular and cellular aspects of troponin cardiomyopathies. Ann N Y Acad Sci. 2004; 1015:214-24.
13. Gomes A, Barnes J, Harada K, Potter J. Role of troponin T in disease. Mol Cell Biochem. 2004; 263(1-2): 115-29.
14. Hernandez O, Szczesna-Cordary D, Knollmann B, Miller T, Bell M, Zhao J, et al. F110I and R278C troponin T mutations that cause familial hypertrophic cardiomyopathy affect muscle contraction in transgenic mice and reconstituted human cardiac fibers. J Biol Chem. 2005; 280(44):37183-94.
15. Chandra M, Rundell V, Tardiff J, Leinwand L, De Tombe P, Solaro R. Ca(2+) activation of myofilaments from transgenic mouse hearts expressing R92Q mutant cardiac troponin T. Am J Physiol Heart Circ Physiol. 2001; 280(2):H705-13.
16. Montgomery D, Tardiff J, Chandra M. Cardiac troponin T mutations: correlation between the type of mutation and the nature of myofilament dysfunction in transgenic mice. J Physiol. 2001; 536(Pt 2):583-92. PMCID: PMC2278862.

17. Miller T, Szczesna D, Housmans P, Zhao J, de Freitas F, Gomes A, et al. Abnormal contractile function in transgenic mice expressing a familial hypertrophic cardiomyopathy-linked troponin T (I79N) mutation. J Biol Chem. 2001; 276(6):3743-55.
18. Venkatraman G, Harada K, Gomes A, Kerrick W, Potter J. Different functional properties of troponin T mutants that cause dilated cardiomyopathy. J Biol Chem. 2003; 278(43):41670-6.
19. Venkatraman G, Gomes A, Kerrick W, Potter J. Characterization of troponin T dilated cardiomyopathy mutations in the fetal troponin isoform. J Biol Chem. 2005; 280(18):17584-92.
20. Mirza M, Marston S, Willott R, Ashley C, Mogensen J, McKenna W, et al. Dilated cardiomyopathy mutations in three thin filament regulatory proteins result in a common functional phenotype. J Biol Chem. 2005; 280(31):28498-506.
21. Jideama N, Noland T J, Raynor R, Blobe G, Fabbro D, Kazanietz M, et al. Phosphorylation specificities of protein kinase C isozymes for bovine cardiac troponin I and troponin T and sites within these proteins and regulation of myofilament properties. J Biol Chem. 1996; 271(38):23277-83.
22. Du C, Morimoto S, Nishii K, Minakami R, Ohta M, Tadano N, et al. Knock-in mouse model of dilated cardiomyopathy caused by troponin mutation. Circ Res. 2007; 101(2):185-94.
23. Ahmad F, Banerjee S, Lage M, Huang X, Smith S, Saba S, et al. The role of cardiac troponin T quantity and function in cardiac development and dilated cardiomyopathy. PLoS One. 2008; 3(7):e2642. PMCID: PMC2441440.
24. Bristow M, Ginsburg R, Minobe W, Cubicciotti R, Sageman W, Lurie K, et al. Decreased catecholamine sensitivity and beta-adrenergic-receptor density in failing human hearts. N Engl J Med. 1982; 307(4):205-11.
25. Bristow M, Ginsburg R, Umans V, Fowler M, Minobe W, Rasmussen R, et al. Beta 1- and beta 2-adrenergic-receptor subpopulations in nonfailing and failing human ventricular myocardium: coupling of both receptor subtypes to muscle contraction and selective beta 1-receptor down-regulation in heart failure. Circ Res. 1986; 59(3):297-309.
26. Rockman H, Koch W, Lefkowitz R. Seven-transmembrane-spanning receptors and heart function. Nature. 2002; 415(6868):206-12.
27. Moreno-Gonzalez A, Korte F, Dai J, Chen K, Ho B, Reinecke H, et al. Cell therapy enhances function of remote non-infarcted myocardium. J Mol Cell Cardiol. 2009; 47(5):603-13.
28. Lewinter M, Vanburen P. Myofilament remodeling during the progression of heart failure. J Card Fail. 2002; 8(6 Suppl):S271-5.
29. LeWinter M. Functional consequences of sarcomeric protein abnormalities in failing myocardium. Heart Fail Rev. 2005; 10(3):249-57.
30. LeWinter M, VanBuren P. Sarcomeric proteins in hypertrophied and failing myocardium: an overview. Heart Fail Rev. 2005; 10(3):173-4.
31. Garvey J, Kranias E, Solaro R. Phosphorylation of C-protein, troponin I and phospholamban in isolated rabbit hearts. Biochem J. 1988; 249(3):709-14. PMCID: PMC1148764.
32. Westfall M, Solaro R. Alterations in myofibrillar function and protein profiles after complete global ischemia in rat hearts. Circ Res. 1992; 70(2):302-13.
33. Reiken S, Gaburjakova M, Guatimosim S, Gomez A, D'Armiento J, Burkhoff D, et al. Protein kinase A phosphorylation of the cardiac calcium release channel (ryanodine receptor) in normal and failing hearts. Role of phosphatases and response to isoproterenol. J Biol Chem. 2003; 278(1):444-53.
34. Obayashi M, Xiao B, Stuyvers B, Davidoff A, Mei J, Chen S, et al. Spontaneous diastolic contractions and phosphorylation of the cardiac ryanodine receptor at serine-2808 in congestive heart failure in rat. Cardiovasc Res. 2006; 69(1):140-51.
35. Schwinger R, Bölck B, Münch G, Brixius K, Müller-Ehmsen J, Erdmann E. cAMP-dependent protein kinase A-stimulated sarcoplasmic reticulum function in heart failure. Ann N Y Acad Sci. 1998; 853:240-50.
36. Forissier J, Carrier L, Farza H, Bonne G, Bercovici J, Richard P, et al. Codon 102 of the cardiac troponin T gene is a putative hot spot for mutations in familial hypertrophic cardiomyopathy. Circulation. 1996; 94(12):3069-73.
37. Moolman J, Corfield V, Posen B, Ngumbela K, Seidman C, Brink P, et al. Sudden death due to troponin T mutations. J Am Coll Cardiol. 1997; 29(3):549-55.
38. Watkins H, McKenna W, Thierfelder L, Suk H, Anan R, O'Donoghue A, et al. Mutations in the genes for cardiac troponin T and alpha-tropomyosin in hypertrophic cardiomyopathy. N Engl J Med. 1995; 332(16):1058-64.
39. Blankinship M, Gregorevic P, Allen J, Harper S, Harper H, Halbert C, et al. Efficient transduction of skeletal muscle using vectors based on adeno-associated virus serotype 6. Mol Ther. 2004; 10(4):671-8.
40. Sanbe A, Gulick J, Hanks M, Liang Q, Osinska H, Robbins J. Reengineering inducible cardiac-specific transgenesis with an attenuated myosin heavy chain promoter. Circ Res. 2003; 92(6):609-16.
41. Davis J, Metzger J. Combinatorial effects of double cardiomyopathy mutant alleles in rodent myocytes: a predictive cellular model of myofilament dysregulation in disease. PLoS One. 2010; 5(2):e9140. PMCID: PMC2818843.
42. Navedo M, Takeda Y, Nieves-Cintrón M, Molkentin J, Santana L. Elevated Ca2+ sparklet activity during acute hyperglycemia and diabetes in cerebral arterial smooth muscle cells. Am J Physiol Cell Physiol. 2010; 298(2):C211-20. PMCID: PMC2822492.
43. Navedo M, Nieves-Cintrón M, Amberg G, Yuan C, Votaw V, Lederer W, et al. AKAP150 is required for stuttering persistent Ca2+ sparklets and angiotensin II-induced hypertension. Circ Res. 2008; 102(2):e1-e11.
44. Rodgers B, Interlichia J, Garikipati D, Mamidi R, Chandra M, Nelson O, et al. Myostatin represses physiological hypertrophy of the heart and excitation-contraction coupling. J Physiol. 2009; 587(Pt 20):4873-86. PMCID: PMC2770153.
45. Rossow C, Dilly K, Yuan C, Nieves-Cintrón M, Cabarrus J, Santana L. NFATc3-dependent loss of I(to) gradient across the left ventricular wall during chronic beta adrenergic stimulation. J Mol Cell Cardiol. 2009; 46(2):249-56.
46. Zhu W, Santana L, Laflamme M. Local control of excitation-contraction coupling in human embryonic stem cell-derived cardiomyocytes. PLoS One. 2009; 4(4):e5407. PMCID: PMC2671137.
47. Hancock W, Martyn D, Huntsman L. Ca2+ and segment length dependence of isometric force kinetics in intact ferret cardiac muscle. Circ Res. 1993; 73(4):603-11.
48. Janssen P, Lehnart S, Prestle J, Lynker J, Salfeld P, Just H, et al. The trabecula culture system: a novel technique 48. to study contractile parameters over a multiday time period. Am J Physiol. 1998; 274(5 Pt 2):H1481-8.
49. Monasky M, Varian K, Davis J, Janssen P. Dissociation of force decline from calcium decline by preload in isolated rabbit myocardium. Pflugers Arch. 2008; 456(2): 267-76.
50. Varian K, Raman S, Janssen P. Measurement of myofilament calcium sensitivity at physiological temperature in intact cardiac trabeculae. Am J Physiol Heart Circ Physiol. 2006; 290(5):H2092-7.
51. Varian K, Janssen P. Frequency-dependent acceleration of relaxation involves decreased myofilament calcium sensitivity. Am J Physiol Heart Circ Physiol. 2007; 292 (5):H2212-9.
52. Huntsman L, Rondinone J, Martyn D. Force-length relations in cardiac muscle segments. Am J Physiol. 1983; 244(5):H701-7.
53. Guo T, Cornea R, Huke S, Camors E, Yang Y, Picht E, et al. Kinetics of FKBP12.6 binding to ryanodine receptors in permeabilized cardiac myocytes and effects on Ca sparks. Circ Res. 2010; 106(11):1743-52. PMCID: PMC2895429.
54. Gellen B, Fernindez-Velasco M, Briec F, Vinet L, LeQuang K, Rouet-Benzineb P, et al. Conditional FKBP12.6 overexpression in mouse cardiac myocytes prevents triggered ventricular tachycardia through specific alterations in excitation-contraction coupling. Circulation. 2008; 117(14):1778-86.
55. Backs J, Backs T, Neef S, Kreusser M, Lehmann L, Patrick D, et al. The delta isoform of CaM kinase II is required for pathological cardiac hypertrophy and remodeling after pressure overload. Proc Natl Acad Sci USA. 2009; 106(7):2342-7. PMCID: PMC2650158.
56. Ling H, Zhang T, Pereira L, Means C, Cheng H, Gu Y, et al. Requirement for Ca2+/calmodulin-dependent kinase II in the transition from pressure overload-induced cardiac hypertrophy to heart failure in mice. J Clin Invest. 2009; 119(5):1230-40. PMCID: PMC2673879.
57. Lygren B, Taskén K. Compartmentalized cAMP signalling is important in the regulation of Ca(2+) cycling in the heart. Biochem Soc Trans. 2006; 34(Pt 4):489-91.
58. Guinto P, Haim T, Dowell-Martino C, Sibinga N, Tardiff J. Temporal and mutation-specific alterations in Ca2+ homeostasis differentially determine the progression of cTnT-related cardiomyopathies in murine models. Am J Physiol Heart Circ Physiol. 2009; 297(2):H614-26. PMCID: PMC2724218.
59. Colomo F, Piroddi N, Poggesi C, te Kronnie G, Tesi C. Active and passive forces of isolated myofibrils from cardiac and fast skeletal muscle of the frog. J Physiol. 1997; 500 (Pt 2):535-48. PMCID: PMC1159402.
60. Colomo F, Nencini S, Piroddi N, Poggesi C, Tesi C. Calcium dependence of the apparent rate of force generation in single striated muscle myofibrils activated by rapid solution changes. Adv Exp Med Biol. 1998; 453: 373-81; discussion 81-2.
61. Piroddi N, Tesi C, Pellegrino M, Tobacman L, Homsher E, Poggesi C. Contractile effects of the exchange of cardiac troponin for fast skeletal troponin in rabbit psoas single myofibrils. J Physiol. 2003; 552(Pt 3):917-31. PMCID: PMC2343446.
62. Piroddi N, Belus A, Scellini B, Tesi C, Giunti G, Cerbai E, et al. Tension generation and relaxation in single myofibrils from human atrial and ventricular myocardium. Pflugers Arch. 2007; 454(1):63-73.
63. Belus A, Piroddi N, Scellini B, Tesi C, Amati G, Girolami F, et al. The familial hypertrophic cardiomyopathy-associated myosin mutation R403Q accelerates tension generation and relaxation of human cardiac myofibrils. J Physiol. 2008; 586(Pt 15):3639-44. PMCID: PMC2538824.
64. Stehle R, Solzin J, Iorga B, Poggesi C. Insights into the kinetics of Ca2+-regulated contraction and relaxation from myofibril studies. Pflugers Arch. 2009; 458(2):337-57.
65. Zoghbi W A, Quinones M A. Determination of cardiac output by Doppler echocardiography: a critical appraisal. Herz. 1986; 11(5):258-68.
66. Berry M F, Engler A J, Woo Y J, Pirolli T J, Bish L T, Jayasankar V, et al. Mesenchymal stem cell injection after myocardial infarction improves myocardial compliance. Am J Physiol Heart Circ Physiol. 2006; 290(6):H2196-203.
67. Tanaka N, Dalton N, Mao L, Rockman H A, Peterson K L, Gottshall K R, et al. Transthoracic echocardiography in models of cardiac disease in the mouse. Circulation. 1996; 94(5):1109-17.
68. Stevens K, Kreutziger K, Dupras S, Korte F, Regnier M, Muskheli V, et al. Physiological function and transplantation of scaffold-free and vascularized human cardiac muscle tissue. Proc Natl Acad Sci USA. 2009; 106(39): 16568-73. PMCID: PMC2746126.
69. Walker L, Walker J, Ambler S, Buttrick P. Stage-specific changes in myofilament protein phosphorylation following myocardial infarction in mice. J Mol Cell Cardiol. 2010; 48(6): 1180-6.
70. Wang J, Liu X, Arneja A, Dhalla N. Alterations in protein kinase A and protein kinase C levels in heart failure due to genetic cardiomyopathy. Can J Cardiol. 1999; 15(6): 683-90.
71. Wang X, Dhalla N. Modification of beta-adrenoceptor signal transduction pathway by genetic manipulation and heart failure. Mol Cell Biochem. 2000; 214(1-2): 131-55.
72. Korte F S, Feest E R, Razumova M V, Regnier M. Sarcomere Length Dependent Contractile Activation is Reduced in Rat Trabeculae Exchanged with cTn Containing the L48Q cTnC Variant Independently of Strong Binding Cross-Bridges. Biophysical Journal. 2010; 98(3): 356a.
73. He H, Javadpour M, Latif F, Tardiff J, Ingwall J. R-92L and R-92W mutations in cardiac troponin T lead to distinct energetic phenotypes in intact mouse hearts. Biophys J. 2007; 93(5):1834-44. PMCID: PMC1948064.
74. Rice R, Guinto P, Dowell-Martino C, He H, Hoyer K, Krenz M, et al. Cardiac myosin heavy chain isoform exchange alters the phenotype of cTnT-related cardiomyopathies in mouse hearts. J Mol Cell Cardiol. 2010; 48(5):979-88.
75. Haim T, Dowell C, Diamanti T, Scheuer J, Tardiff J. Independent FHC-related cardiac troponin T mutations exhibit specific alterations in myocellular contractility and calcium kinetics. J Mol Cell Cardiol. 2007; 42(6): 1098-110.
76. Ertz-Berger B, He H, Dowell C, Factor S, Haim T, Nunez S, et al. Changes in the chemical and dynamic properties of cardiac troponin T cause discrete cardiomyopathies in transgenic mice. Proc Natl Acad Sci USA. 2005; 102(50):18219-24. PMCID: PMC1298915.
77. Gilman G, Khandheria B K, Hagen M E, Abraham T P, Seward J B, Belohlavek M. Strain rate and strain: a step-by-step approach to image and data acquisition. J Am Soc Echocardiogr. 2004; 17(9):1011-20.

78. Pislaru C, Abraham T P, Belohlavek M. Strain and strain rate echocardiography. Curr Opin Cardiol. 2002; 17(5): 443-54.
79. Becker M, Bilke E, Kuhl H, Katoh M, Kramann R, Franke A, et al. Analysis of myocardial deformation based on pixel tracking in two dimensional echocardiographic images enables quantitative assessment of regional left ventricular function. Heart. 2006; 92(8):1102-8.
80. Leitman M, Lysyansky P, Sidenko S, Shir V, Peleg E, Binenbaum M, et al. Two-dimensional strain—a novel software for real-time quantitative echocardiographic assessment of myocardial function. J Am Soc Echocardiogr. 2004; 17(10):1021-9.
1.* Regnier M, Rivera A J, Chen Y, Chase P B. 2-deoxy-ATP enhances contractility of rat cardiac muscle. Circ Res. 2000; 86(12):1211-1217.
2.* Regnier M, Martin H, Barsotti R J, Rivera A J, Martyn D A, Clemmens E. Cross-bridge versus thin filament contributions to the level and rate of force development in cardiac muscle. Biophys J. 2004; 87(3): 1815-1824.
3.* Adhikari B B, Regnier M, Rivera A J, Kreutziger K L, Martyn D A. Cardiac length dependence of force and force redevelopment kinetics with altered cross-bridge cycling. Biophys J. 2004; 87(3):1784-1794.
4.* Regnier M, Homsher E. The effect of ATP analogs on posthydrolytic and force development steps in skinned skeletal muscle fibers. Biophys J. 1998; 74(6):3059-3071.
5.* Regnier M, Lee D M, Homsher E. ATP analogs and muscle contraction: mechanics and kinetics of nucleoside triphosphate binding and hydrolysis. Biophys J. 1998; 74(6):3044-3058.
6.* Regnier M, Martyn D A, Chase B P. Calcium regulation of tension redevelopment kinetics with 2-deoxy-ATP or low [ATP] in rabbit skeletal muscle. Biophysical Journal. 1998; 74(4):2005-2015.
7.* Korte F S, Dai J, Buckley K, Feest E R, Murry C E, Regnier M. Upregulation of cardiomyocyte ribonucleotide reductase increases intracellular 2-deoxy-ATP, contractility, and relaxation. Circulation Research. 2011; In Review.
8.* Bristow M R, Ginsburg R, Minobe W, Cubicciotti R S, Sageman W S, Lurie K, Billingham M E, Harrison D C, Stinson E B. Decreased catecholamine sensitivity and beta-adrenergic-receptor density in failing human hearts. N Engl J Med. 1982; 307(4):205-211.
9.* Bristow M R, Ginsburg R, Umans V, Fowler M, Minobe W, Rasmussen R, Zera P, Menlove R, Shah P, Jamieson S. Beta 1- and beta 2-adrenergic-receptor subpopulations in nonfailing and failing human ventricular myocardium: coupling of both receptor subtypes to muscle contraction and selective beta 1-receptor down-regulation in heart failure. Circ Res. 1986; 59(3):297-309.
10.* Rockman H A, Koch W J, Lefkowitz R J. Seven-transmembrane-spanning receptors and heart function. Nature. 2002; 415(6868):206-212.
11.* Moreno-Gonzalez A, Korte F S, Dai J, Chen K Y, Ho B, Reinecke H, Murry C E, Regnier M. Cell therapy enhances function of remote non-infarcted myocardium. Journal of Molecular and Cellular Cardiology. 2009; 47(5):603-613.
12.* Lewinter M M, Vanburen P. Myofilament remodeling during the progression of heart failure. J Card Fail. 2002; 8(6 Suppl):S271-275.
13.* LeWinter M. Functional consequences of sarcomeric protein abnormalities in failing myocardium. Heart Fail Rev. 2005; 10(3):249-257.
14.* LeWinter M, VanBuren P. Sarcomeric proteins in hypertrophied and failing myocardium: an overview. Heart Fail Rev. 2005; 10(3):173-174.
15.* Garvey J L, Kranias E G, Solaro R J. Phosphorylation of C-protein, troponin I and phospholamban in isolated rabbit hearts. Biochem J. 1988; 249(3):709-714.
16.* Westfall M V, Solaro R J. Alterations in myofibrillar function and protein profiles after complete global ischemia in rat hearts. Circ Res. 1992; 70(2):302-313.
17.* Reiken S, Gaburjakova M, Guatimosim S, Gomez A M, D'Armiento J, Burkhoff D, Wang J, Vassort G, Lederer W J, Marks A R. Protein kinase A phosphorylation of the cardiac calcium release channel (ryanodine receptor) in normal and failing hearts. Role of phosphatases and response to isoproterenol. J Biol Chem. 2003; 278(1): 444-453.
18.* Obayashi M, Xiao B, Stuyvers B D, Davidoff A W, Mei J, Chen S R, ter Keurs H E. Spontaneous diastolic contractions and phosphorylation of the cardiac ryanodine receptor at serine-2808 in congestive heart failure in rat. Cardiovasc Res. 2006; 69(1):140-151.
19.* Rubart M, Zipes D P. Mechanisms of sudden cardiac death. J Clin Invest. 2005; 115(9):2305-2315.
20.* Kass D A, Solaro R J. Mechanisms and use of calcium-sensitizing agents in the failing heart. Circulation. 2006; 113(2):305-315.
21.* Edes I, Kiss E, Kitada Y, Powers F M, Papp J G, Kranias E G, Solaro R J. Effects of Levosimendan, a cardiotonic agent targeted to troponin C, on cardiac function and on phosphorylation and Ca2+ sensitivity of cardiac myofibrils and sarcoplasmic reticulum in guinea pig heart. Circ Res. 1995; 77(1):107-113.
22.* Wyskovsky W, Hauptner R, Suko J. Drug-induced calcium release from heavy sarcoplasmic reticulum of skeletal muscle. Biochim. Biophys. Acta. 1988; 938:89-96.
23.* Schoffstall B, Clark A, Chase P B. Positive inotropic effects of low dATP/ATP ratios on mechanics and kinetics of porcine cardiac muscle. Biophys J. 2006; 91(6):2216-2226.
24.* Blankinship M J, Gregorevic P, Allen J M, Harper S Q, Harper H, Halbert C L, Miller A D, Miller D A, Chamberlain J S. Efficient transduction of skeletal muscle using vectors based on adeno-associated virus serotype 6. Mol Ther. 2004; 10(4):671-678.
25.* Xu X, Page J L, Surtees J A, Liu H, Lagedrost S, Lu Y, Bronson R, Alani E, Nikitin A Y, Weiss R S. Broad overexpression of ribonucleotide reductase genes in mice specifically induces lung neoplasms. Cancer Res. 2008; 68(8):2652-2660.
26.* Ylikallio E, Page J L, Xu X, Lampinen M, Bepler G, Ide T, Tyynismaa H, Weiss R S, Suomalainen A. Ribonucleotide reductase is not limiting for mitochondrial DNA copy number in mice. Nucleic Acids Research. 2010; 38(22):8208-8218.
27.* Baudenbacher F, Schober T, Pinto J R, Sidorov V Y, Hilliard F, Solaro R J. Myofilament Ca2+ sensitization causes susceptibility to cardiac arrythmia in mice. Journal of Clinical Investigation. 2008; 118(12):3893-3903.
28.* Solaro R J, Gambassi G, Warshaw D M, Keller M R, Spurgeon H A, Beier N. Stereoselective actions of thiadiazinones on canine cardiac myocytes and myofilaments. Circ Res. 1993; 73(6):981-990.
29.* White J, Lee J A, Shah N, Orchard C H. Differential effects of the optical isomers of EMD 53998 on contraction and cytoplasmic Ca2+ in isolated ferret cardiac muscle. Circ Res. 1993; 73(1):61-70.

30.* Huke S, Knollmann B C. Increased myofilament Ca2+ sensitivity and arrhythmia susceptibility. Journal of Molecular and Cellular Cardiology. 2010; 48(5):824-833.

31.* Zoghbi W A, Quinones M A. Determination of cardiac output by Doppler echocardiography: a critical appraisal. Herz. 1986; 11(5):258-268.

32.* Berry M F, Engler A J, Woo Y J, Pirolli T J, Bish L T, Jayasankar V, Morine K J, Gardner T J, Discher D E, Sweeney H L. Mesenchymal stem cell injection after myocardial infarction improves myocardial compliance. Am J Physiol Heart Circ Physiol. 2006; 290(6):H2196-2203.

33.* Tanaka N, Dalton N, Mao L, Rockman H A, Peterson K L, Gottshall K R, Hunter J J, Chien K R, Ross J, Jr. Transthoracic echocardiography in models of cardiac disease in the mouse. Circulation. 1996; 94(5):1109-1117.

34.* Fernandes S, Naumova A V, Zhu W Z, Laflamme M A, Gold J, Murry C E. Human embryonic stem cell-derived cardiomyocytes engraft but do not alter cardiac remodeling after chronic infarction in rats. Journal of Molecular and Cellular Cardiology. 2010; 49:941-949.

35.* Monasky M M, Varian K D, Davis J P, Janssen P M. Dissociation of force decline from calcium decline by preload in isolated rabbit myocardium. Pflugers Arch. 2008; 456(2):267-276.

36.* Varian K, Raman S, Janssen P. Measurement of myofilament calcium sensitivity at physiological temperature in intact cardiac trabeculae. Am J Physiol Heart Circ Physiol. 2006; 290(5):H2092-2097.

37.* Varian K D, Janssen P M. Frequency-dependent acceleration of relaxation involves decreased myofilament calcium sensitivity. Am J Physiol Heart Circ Physiol. 2007; 292(5):H2212-2219.

38.* Janssen P, Lehnart S, Prestle J, Lynker J, Salfeld P, Just H, Hasenfuss G. The trabecula culture system: a novel technique to study contractile parameters over a multiday time period. Am J Physiol. 1998; 274(5 Pt 2):H1481-1488.

39.* Kreutziger K L, Piroddi N, J. T. M, Tesi C, Poggesi C, Regnier M. Cooperative activation and tension kinetics in cardiac muscle are strongly modulated by calcium binding kinetics of troponin C. Journal of Molecular and Cellular Cardiology. 2011; 50(1):165-174.

40.* Kreutziger K L, Piroddi N, Scellini B, Tesi C, Poggesi C, Regnier M. Thin filament Ca2+ binding properties and regulatory unit interactions alter kinetics of tension development and relaxation in rabbit skeletal muscle. Journal of Physiology. 2008; 586(15):3683-3700.

41.* Belus A, Piroddi N, Tesi C. Mechanism of cross-bridge detachment in isometric force relaxation of skeletal and cardiac myofibrils. Journal of Muscle Research and Cell Motility. 2003; 24(4-6):261-267.

42.* Guo X, Laflamme M A, Becker P L. Cyclic ADP-ribose does not regulate sarcoplasmic reticulum Ca2+ release in intact cardiomyocytes. Circ Res. 1996; 79:147-151.

43.* Laflamme M A, Becker P L. Ca2+-induced current oscillations in rabbit ventricular myocytes. Circ Res. 1996; 78:707-716

44.* Laflamme M A, Becker P L. Do beta 2-adrenergic receptors modulate Ca2+ in adult rat ventricular myocytes?Am J Physiol. 1998; 274:H1308-1314.

45.* Zhu W Z, Santana L F, Laflamme M A. Local control of excitation-contraction coupling in human embryonic stem cell-derived cardiomyocytes. PLoS One. 2009; 4:e5407.

46.* Zhu W Z, Xie Y, Moyes K W, Gold J D, Askari B, Laflamme M A. Neuregulin/erbb signaling regulates cardiac subtype specification in differentiating human embryonic stem cells. Circ Res. 2010; 107:776-786.

47.* Adler E D, Chen V C, Bystrup A, Kaplan A D, Giovannone S, Briley-Saebo K, Young W, Kattman S, Mani V, Laflamme M A, Zhu W Z, Fayad Z, Keller G. The cardiomyocyte lineage is critical for optimization of stem cell therapy in a mouse model of myocardial infarction. Faseb J. 2010; 24:1073-1081.

48.* Xu C, Police S, Hassanipour M, Li Y, Chen Y, Priest C, O'Sullivan C, Laflamme M A, Zhu W Z, Van Biber B, Hegerova L, Yang J, Delavan-Boorsma K, Davies A, Lebkowski J, Gold J D. Efficient generation and cryopreservation of cardiomyocytes derived from human embryonic stem cells. Regenerative Medicine. 2011; 6:53-66.

49.* Magistretti J, Mantegazza M, de Curtis M, Wanke E. Modalities of distortion of physiological voltage signals by patch-clamp amplifiers: a modeling study. Biophys J. 1998; 74(2 Pt 1):831-842.

50.* Magistretti J, Mantegazza M, Guatteo E, Wanke E. Action potentials recorded with patch-clamp amplifiers: are they genuine?Trends Neurosci. 1996; 19(12):530-534.

51.* Akaike N, Harata N. Nystatin perforated patch recording and its applications to analyses of intracellular mechanisms. Jpn J Physiol. 1994; 44(5):433-473.

52.* Strauss U, Herbrik M, Mix E, Schubert R, Rolfs A. Whole-cell patch-clamp: true perforated or spontaneous conventional recordings?Pflugers Arch. 2001; 442(4): 634-638.

53.* Cheng H, Lederer W J, Cannell M B. Calcium sparks: elementary events underlying excitation-contraction coupling in heart muscle. Science. 1993; 262(5134):740-744.

54.* Maravall M, Mainen Z F, Sabatini B L, Svoboda K. Estimating intracellular calcium concentrations and buffering without wavelength ratioing. Biophys J. 2000; 78(5):2655-2667.

55.* Santana L F, Cheng H, Gomez A M, Cannell M B, Lederer W J. Relation between the sarcolemmal Ca2+ current and Ca2+ sparks and local control theories for cardiac excitation-contraction coupling. Circ Res. 1996; 78(1):166-171.

56.* Guo X, Laflamme M A, Becker P L. Cyclic ADP-ribose does not regulate sarcoplasmic reticulum Ca2+ release in intact cardiac myocytes. Circ Res. 1996; 79(1):147-151.

57.* Zhu W Z, Santana L F, Laflamme M A. Local control of excitation-contraction coupling in human embryonic stem cell-derived cardiomyocytes. PLoS ONE. 2009; 4(4):e5407.

58.* Santana L F, Kranias E G, Lederer W J. Calcium sparks and excitation-contraction coupling in phospholamban-deficient mouse ventricular myocytes. J Physiol. 1997; 503 (Pt 1):21-29.

59.* Bassani R A, Bassani J W, Bers D M. Mitochondrial and sarcolemmal Ca2+ transport reduce [Ca2+]i during caffeine contractures in rabbit cardiac myocytes. J Physiol. 1992; 453:591-608.

60.* Bassani J W, Bassani R A, Bers D M. Relaxation in rabbit and rat cardiac cells: species-dependent differences in cellular mechanisms. J Physiol. 1994; 476(2):279-293.

61.* Terracciano C M, Philipson K D, MacLeod K T. Overexpression of the Na(+)/Ca(2+) exchanger and inhibition of the sarcoplasmic reticulum Ca(2+)-ATPase in ventricular myocytes from transgenic mice. Cardiovasc Res. 2001; 49(1):38-47.

62.* Dilly K W, Rossow C F, Votaw V S, Meabon J S, Cabarrus J L, Santana L F. Mechanisms underlying varia- 63.* Luptak I, Balschi J A, Xing Y, Leone T C, Kelly D P, Tian R. Decreased contractile and metabolic reserve in peroxisome proliferator-activated receptor-alpha null hearts can be rescued by increasing glucose transport and utilization. Circulation. 2005; 112(15):2339-2346.

64.* Yan J, Young M E, Cui L, Lopaschuk G D, Liao R, Tian R. Increased glucose uptake and oxidation in mouse hearts prevent fatty acid oxidation but cause cardiac dysfunction in diet-induced obesity. Circulation. 2009; 119(21):2818-2828.

65.* Xing Y, Musi N, Fujii N, Zou L, Luptak I, Hirshman M F, Goodyear L J, Tian R. Glucose metabolism and energy homeostasis in mouse hearts overexpressing dominant negative alpha2 subunit of AMP-activated protein kinase. J. Biol. Chem. 2003; 278(31):28372-28377.

66.* Kuznetsov A V, Veksler V, Gellerich F N, Saks V, Margreiter R, Kunz W S. Analysis of mitochondrial function in situ in permeabilized muscle fibers, tissues and cells. Nat Protoc. 2008; 3(6):965-976.

67.* Boudina S, Sena S, O'Neill B T, Tathireddy P, Young M E, Abel E D. Reduced mitochondrial oxidative capacity and increased mitochondrial uncoupling impair myocardial energetics in obesity. Circulation. 2005; 112(17): 2686-2695.

68.* Karamanlidis G, Nascimben L, Couper G S, Shekar P S, Del Monte F, Tian R. Defective DNA replication impairs mitochondrial biogenesis in human failing hearts. Circ Res. 2010; 106(9):1541-1548.

69.* Neubauer S. The failing heart—an engine out of fuel. N Engl J Med. 2007; 256(11):1140-1151.

1. Regnier M, Rivera A J, Chen Y, Chase P B. 2-deoxy-ATP enhances contractility of rat cardiac muscle. *Circ Res.* 2000; 86(12):1211-1217.

2. Regnier M, Martin H, Barsotti R J, Rivera A J, Martyn D A, Clemmens E. Cross-bridge versus thin filament contributions to the level and rate of force development in cardiac muscle. *Biophys J.* 2004; 87(3):1815-1824.

3. Adhikari B B, Regnier M, Rivera A J, Kreutziger K L, Martyn D A. Cardiac length dependence of force and force redevelopment kinetics with altered cross-bridge cycling. *Biophys J.* 2004; 87(3):1784-1794.

4. Regnier M, Homsher E. The effect of ATP analogs on posthydrolytic and force development steps in skinned skeletal muscle fibers. *Biophys J.* 1998; 74(6):3059-3071.

5. Regnier M, Lee D M, Homsher E. ATP analogs and muscle contraction: mechanics and kinetics of nucleoside triphosphate binding and hydrolysis. *Biophys J.* 1998; 74(6):3044-3058.

6. Regnier M, Martyn D A, Chase B P. Calcium regulation of tension redevelopment kinetics with 2-deoxy-ATP or low [ATP] in rabbit skeletal muscle. *Biophysical Journal.* 1998; 74(4):2005-2015.

7. Korte F S, Dai J, Buckley K, Feest E R, Adamek N, Geeves M A, Murry C E, Regnier M. Upregulation of cardiomyocyte ribonucleotide reductase increases intracellular 2 deoxy-ATP, contractility, and relaxation. *J Mol Cell Cardiol.* 2011; 51(6):894-901.

8. Bristow M R, Ginsburg R, Minobe W, Cubicciotti R S, Sageman W S, Lurie K, Billingham M E, Harrison D C, Stinson E B. Decreased catecholamine sensitivity and beta-adrenergic-receptor density in failing human hearts. *N Engl J Med.* 1982; 307(4):205-211.

9. Bristow M R, Ginsburg R, Umans V, Fowler M, Minobe W, Rasmussen R, Zera P, Menlove R, Shah P, Jamieson S. Beta 1- and beta 2-adrenergic-receptor subpopulations in nonfailing and failing human ventricular myocardium: coupling of both receptor subtypes to muscle contraction and selective beta 1-receptor down-regulation in heart failure. *Circ Res.* 1986; 59(3):297-309.

10. Rockman H A, Koch W J, Lefkowitz R J. Seven-transmembrane-spanning receptors and heart function. *Nature.* 2002; 415(6868):206-212.

11. Moreno-Gonzalez A, Korte F S, Dai J, Chen K Y, Ho B, Reinecke H, Murry C E, Regnier M. Cell therapy enhances function of remote non-infarcted myocardium. *Journal of Molecular and Cellular Cardiology.* 2009; 47(5):603-613.

12. Lewinter M M, Vanburen P. Myofilament remodeling during the progression of heart failure. *J Card Fail.* 2002; 8(6 Suppl):S271-275.

13. LeWinter M. Functional consequences of sarcomeric protein abnormalities in failing myocardium. *Heart Fail Rev.* 2005; 10(3):249-257.

14. LeWinter M, VanBuren P. Sarcomeric proteins in hypertrophied and failing myocardium: an overview. *Heart Fail Rev.* 2005; 10(3):173-174.

15. Garvey J L, Kranias E G, Solaro R J. Phosphorylation of C-protein, troponin I and phospholamban in isolated rabbit hearts. *Biochem J.* 1988; 249(3):709-714.

16. Westfall M V, Solaro R J. Alterations in myofibrillar function and protein profiles after complete global ischemia in rat hearts. *Circ Res.* 1992; 70(2):302-313.

17. Reiken S, Gaburjakova M, Guatimosim S, Gomez A M, D'Armiento J, Burkhoff D, Wang J, Vassort G, Lederer W J, Marks A R. Protein kinase A phosphorylation of the cardiac calcium release channel (ryanodine receptor) in normal and failing hearts. Role of phosphatases and response to isoproterenol. *J Biol Chem.* 2003; 278(1):444-453.

18. Obayashi M, Xiao B, Stuyvers B D, Davidoff A W, Mei J, Chen S R, ter Keurs H E. Spontaneous diastolic contractions and phosphorylation of the cardiac ryanodine receptor at serine-2808 in congestive heart failure in rat. *Cardiovasc Res.* 2006; 69(1):140-151.

19. del Monte F, Harding S, Schmidt U, Matsui T, Kang Z, Matsui T, Guerrero J, Gwathmey J, Rosenzweig A, Hajjar R. Restoration of contractile function in isolated cardiomyocytes from failing human hearts by gene transfer of SERCA2a. *Circulation.* 2000; 100:2308-2311.

20. Miyamoto M, del Monte F, Schmidt U, DiSalvo T, Kang Z, Dec G, Gwathmey J, Rosenzweig A, Hajjar R. Adenoviral gene transfer of SERCA2a improves left-ventricular function in aortic-banded rats in transition to heart failure. *Proceedings of the National Academy of Sciences USA.* 2000; 97:793-798.

21. Kass D A, Solaro R J. Mechanisms and use of calcium-sensitizing agents in the failing heart. *Circulation.* 2006; 113(2):305-315.

22. Rubart M, Zipes D P. Mechanisms of sudden cardiac death. *J Clin Invest.* 2005; 115(9):2305-2315.

23. Edes I, Kiss E, Kitada Y, Powers F M, Papp J G, Kranias E G, Solaro R J. Effects of Levosimendan, a cardiotonic agent targeted to troponin C, on cardiac function and on phosphorylation and Ca2+ sensitivity of cardiac myofibrils and sarcoplasmic reticulum in guinea pig heart. *Circ Res.* 1995; 77(1):107-113.

24. Wyskovsky W, Hauptner R, Suko J. Drug-induced calcium release from heavy sarcoplasmic reticulum of skeletal muscle. *Biochim. Biophys. Acta.* 1988; 938:89-96.

25. Xu X, Page J L, Surtees J A, Liu H, Lagedrost S, Lu Y, Bronson R, Alani E, Nikitin A Y, Weiss R S. Broad overexpression of ribonucleotide reductase genes in mice specifically induces lung neoplasms. *Cancer Res.* 2008; 68(8):2652-2660.

26. Ylikallio E, Page J L, Xu X, Lampinen M, Bepler G, Ide T, Tyynismaa H, Weiss R S, Suomalainen A. Ribonucleotide reductase is not limiting for mitochondrial DNA copy number in mice. *Nucleic Acids Research.* 2010; 38(22):8208-8218.

27. Korte F S, Dai J, Buckley K, Feest E R, Murry C E, Regnier M. Upregulation of cardiomyocyte ribonucleotide reductase increases intracellular 2-deoxy-ATP, contractility, and relaxation. *Circulation Research.* 2011; In Review.

28. McDonald K S, Moss R L. Strongly binding myosin cross-bridges regulate loaded shortening and power output in cardiac myocytes. *Circulation Research.* 2000; 87:768-773.

29. Dobesh D P, Konhilas J P, de Tombe P P. Cooperative activation in cardiac muscle: impact of sarcomere length. *Am J Physiol Heart Circ Physiol.* 2002; 282(3):H1055-1062.

30. Kinoshita Y, Nishigaki K. Unexpectedly general replaceability of ATP in ATP-requiring enzymes. *J Biochem.* 1997; 122(1):205-211.

31. Trumble W R, Sutko J L, Reeves J P. Cardiac sarcolemmal and sarcoplasmic reticulum membrane vesicles exhibit distinctive (Ca—Mg)-ATPase substrate specificities. *J Biol Chem.* 1981; 256(14):7101-7104.

32. Baker A J. Refueling the heart: Using 2-deoxy-ATP to enhance cardiac contractility. *J Mol Cell Cardiol.* 2011; 51(6):883-884.

33. Goldberg G S, Moreno A P, Lampe P D. Gap junctions between cells expressing connexin 43 or 32 show inverse permselectivity to adenosine and ATP. *J Biol Chem.* 2002; 277(39):36725-36730.

34. Kang J, Kang N, Lovatt D, Torres A, Zhao Z, Lin J, Nedergaard M. Connexin 43 hemichannels are permeable to ATP. *J Neurosci.* 2008; 28(18):4702-4711.

35. Blankinship M J, Gregorevic P, Allen J M, Harper S Q, Harper H, Halbert C L, Miller A D, Miller D A, Chamberlain J S. Efficient transduction of skeletal muscle using vectors based on adeno-associated virus serotype 6. *Mol Ther.* 2004; 10(4):671-678.

36. Odom G L, Gregorevic P, Chamberlain J S. Viral-mediated gene therapy for the muscular dystrophies: successes, limitations and recent advances. *Biochim Biophys Acta.* 2007; 1772(2):243-262.

37. Rengo G, Lymperopoulos A, Zincarelli C, Donniacuo M, Soltys S, Rabinowitz J E, Koch W J. Myocardial adeno-associated virus serotype 6-betaARKct gene therapy improves cardiac function and normalizes the neurohormonal axis in chronic heart failure. *Circulation.* 2009; 119(1):89-98.

38. Wang Z, Allen J M, Riddell S R, Gregorevic P, Storb R, Tapscott S J, Chamberlain J S, Kuhr C S. Immunity to adeno-associated virus-mediated gene transfer in a random-bred canine model of Duchenne muscular dystrophy. *Hum Gene Ther.* 2007; 18(1):18-26.

39. Caras I W, Martin D W, Jr. Molecular cloning of the cDNA for a mutant mouse ribonucleotide reductase M1 that produces a dominant mutator phenotype in mammalian cells. *Mol Cell Biol.* 1988; 8(7):2698-2704.

40. Gillis T E, Martyn D A, Rivera A J, Regnier M. Investigation of thin filament near-neighbour regulatory unit interactions during force development in skinned cardiac and skeletal muscle. *J Physiol.* 2007; 580(Pt. 2):561-576.

41. Baudenbacher F, Schober T, Pinto J R, Sidorov V Y, Hilliard F, Solaro R J. Myofilament Ca2+ sensitization causes susceptibility to cardiac arrythmia in mice. *Journal of Clinical Investigation.* 2008; 118(12):3893-3903.

42. Solaro R J, Gambassi G, Warshaw D M, Keller M R, Spurgeon H A, Beier N. Stereoselective actions of thiadiazinones on canine cardiac myocytes and myofilaments. *Circ Res.* 1993; 73(6):981-990.

43. White J, Lee J A, Shah N, Orchard C H. Differential effects of the optical isomers of EMD 53998 on contraction and cytoplasmic Ca2+ in isolated ferret cardiac muscle. *Circ Res.* 1993; 73(1):61-70.

44. Huke S, Knollmann B C. Increased myofilament Ca2+ sensitivity and arrythmia susceptibility. *Journal of Molecular and Cellular Cardiology.* 2010; 48(5):824-833.

45. Zoghbi W A, Quinones M A. Determination of cardiac output by Doppler echocardiography: a critical appraisal. *Herz.* 1986; 11(5):258-268.

46. Berry M F, Engler A J, Woo Y J, Pirolli T J, Bish L T, Jayasankar V, Morine K J, Gardner T J, Discher D E, Sweeney H L. Mesenchymal stem cell injection after myocardial infarction improves myocardial compliance. *Am J Physiol Heart Circ Physiol.* 2006; 290(6):H2196-2203.

47. Tanaka N, Dalton N, Mao L, Rockman H A, Peterson K L, Gottshall K R, Hunter J J, Chien K R, Ross J, Jr. Transthoracic echocardiography in models of cardiac disease in the mouse. *Circulation.* 1996; 94(5):1109-1117.

48. Monasky M M, Varian K D, Davis J P, Janssen P M. Dissociation of force decline from calcium decline by preload in isolated rabbit myocardium. *Pflugers Arch.* 2008; 456(2):267-276.

49. Varian K, Raman S, Janssen P. Measurement of myofilament calcium sensitivity at physiological temperature in intact cardiac trabeculae. *Am J Physiol Heart Circ Physiol.* 2006; 290(5):H2092-2097.

50. Varian K D, Janssen P M. Frequency-dependent acceleration of relaxation involves decreased myofilament calcium sensitivity. *Am J Physiol Heart Circ Physiol.* 2007; 292(5):H2212-2219.

51. Janssen P, Lehnart S, Prestle J, Lynker J, Salfeld P, Just H, Hasenfuss G. The trabecula culture system: a novel technique to study contractile parameters over a multiday time period. *Am J Physiol.* 1998; 274(5 Pt 2):H1481-1488.

52. Kreutziger K L, Piroddi N, J. T. M, Tesi C, Poggesi C, Regnier M. Cooperative activation and tension kinetics in cardiac muscle are strongly modulated by calcium binding kinetics of troponin C. *Journal of Molecular and Cellular Cardiology.* 2011; 50(1):165-174.

53. Kreutziger K L, Piroddi N, Scellini B, Tesi C, Poggesi C, Regnier M. Thin filament Ca2+ binding properties and regulatory unit interactions alter kinetics of tension development and relaxation in rabbit skeletal muscle. *Journal of Physiology.* 2008; 586(15):3683-3700.

54. Belus A, Piroddi N, Tesi C. Mechanism of cross-bridge detachment in isometric force relaxation of skeletal and cardiac myofibrils. *Journal of Muscle Research and Cell Motility.* 2003; 24(4-6):261-267.

55. Guo X, Laflamme M A, Becker P L. Cyclic ADP-ribose does not regulate sarcoplasmic reticulum Ca2+ release in intact cardiomyocytes. *Circ Res.* 1996; 79:147-151.

56. Laflamme M A, Becker P L. Ca2+-induced current oscillations in rabbit ventricular myocytes. *Circ Res.* 1996; 78:707-716
57. Laflamme M A, Becker P L. Do beta 2-adrenergic receptors modulate Ca2+ in adult rat ventricular myocytes? *Am J Physiol.* 1998; 274:H1308-1314.
58. Zhu W Z, Santana L F, Laflamme M A. Local control of excitation-contraction coupling in human embryonic stem cell-derived cardiomyocytes. *PLoS One.* 2009; 4:e5407.
59. Zhu W Z, Xie Y, Moyes K W, Gold J D, Askari B, Laflamme M A. Neuregulin/erbb signaling regulates cardiac subtype specification in differentiating human embryonic stem cells. *Circ Res.* 2010; 107:776-786.
60. Adler E D, Chen V C, Bystrup A, Kaplan A D, Giovannone S, Briley-Saebo K, Young W, Kattman S, Mani V, Laflamme M A, Zhu W Z, Fayad Z, Keller G. The cardiomyocyte lineage is critical for optimization of stem cell therapy in a mouse model of myocardial infarction. *Faseb J.* 2010; 24:1073-1081.
61. Fernandes S, Naumova A V, Zhu W Z, Laflamme M A, Gold J, Murry C E. Human embryonic stem cell-derived cardiomyocytes engraft but do not alter cardiac remodeling after chronic infarction in rats. *Journal of Molecular and Cellular Cardiology.* 2010; 49:941-949.
62. Xu C, Police S, Hassanipour M, Li Y, Chen Y, Priest C, O'Sullivan C, Laflamme M A, Zhu W Z, Van Biber B, Hegerova L, Yang J, Delavan-Boorsma K, Davies A, Lebkowski J, Gold J D. Efficient generation and cryopreservation of cardiomyocytes derived from human embryonic stem cells. *Regenerative Medicine.* 2011; 6:53-66.
63. Magistretti J, Mantegazza M, de Curtis M, Wanke E. Modalities of distortion of physiological voltage signals by patch-clamp amplifiers: a modeling study. *Biophys J.* 1998; 74(2 Pt 1):831-842.
64. Magistretti J, Mantegazza M, Guatteo E, Wanke E. Action potentials recorded with patch-clamp amplifiers: are they genuine? *Trends Neurosci.* 1996; 19(12):530-534.
65. Akaike N, Harata N. Nystatin perforated patch recording and its applications to analyses of intracellular mechanisms. *Jpn J Physiol.* 1994; 44(5):433-473.
66. Strauss U, Herbrik M, Mix E, Schubert R, Rolfs A. Whole-cell patch-clamp: true perforated or spontaneous conventional recordings? *Pflugers Arch.* 2001; 442(4):634-638.
67. Cheng H, Lederer W J, Cannell M B. Calcium sparks: elementary events underlying excitation-contraction coupling in heart muscle. *Science.* 1993; 262(5134):740-744.
68. Maravall M, Mainen Z F, Sabatini B L, Svoboda K. Estimating intracellular calcium concentrations and buffering without wavelength ratioing. *Biophys J.* 2000; 78(5):2655-2667.
69. Santana L F, Cheng H, Gomez A M, Cannell M B, Lederer W J. Relation between the sarcolemmal Ca2+ current and Ca2+ sparks and local control theories for cardiac excitation-contraction coupling. *Circ Res.* 1996; 78(1):166-171.
70. Guo X, Laflamme M A, Becker P L. Cyclic ADP-ribose does not regulate sarcoplasmic reticulum Ca2+ release in intact cardiac myocytes. *Circ Res.* 1996; 79(1):147-151.
71. Zhu W Z, Santana L F, Laflamme M A. Local control of excitation-contraction coupling in human embryonic stem cell-derived cardiomyocytes. *PLoS ONE.* 2009; 4(4):e5407.
72. Santana L F, Kranias E G, Lederer W J. Calcium sparks and excitation-contraction coupling in phospholamban-deficient mouse ventricular myocytes. *J Physiol.* 1997; 503 (Pt 1):21-29.
73. Bassani R A, Bassani J W, Bers D M. Mitochondrial and sarcolemmal Ca2+ transport reduce [Ca2+]i during caffeine contractures in rabbit cardiac myocytes. *J Physiol.* 1992; 453:591-608.
74. Bassani J W, Bassani R A, Bers D M. Relaxation in rabbit and rat cardiac cells: species-dependent differences in cellular mechanisms. *J Physiol.* 1994; 476(2):279-293.
75. Terracciano C M, Philipson K D, MacLeod K T. Overexpression of the Na(+)/Ca(2+) exchanger and inhibition of the sarcoplasmic reticulum Ca(2+)-ATPase in ventricular myocytes from transgenic mice. *Cardiovasc Res.* 2001; 49(1):38-47.
76. Dilly K W, Rossow C F, Votaw V S, Meabon J S, Cabarrus J L, Santana L F. Mechanisms underlying variations in excitation-contraction coupling across the mouse left ventricular free wall. *J Physiol.* 2006; 572(Pt 1):227-241.
77. Luptak I, Balschi J A, Xing Y, Leone T C, Kelly D P, Tian R. Decreased contractile and metabolic reserve in peroxisome proliferator-activated receptor-alpha null hearts can be rescued by increasing glucose transport and utilization. *Circulation.* 2005; 112(15):2339-2346.
78. Yan J, Young M E, Cui L, Lopaschuk G D, Liao R, Tian R. Increased glucose uptake and oxidation in mouse hearts prevent fatty acid oxidation but cause cardiac dysfunction in diet-induced obesity. *Circulation.* 2009; 119(21):2818-2828.
79. Xing Y, Musi N, Fujii N, Zou L, Luptak I, Hirshman M F, Goodyear L J, Tian R. Glucose metabolism and energy homeostasis in mouse hearts overexpressing dominant negative alpha2 subunit of AMP-activated protein kinase. *J. Biol. Chem.* 2003; 278(31):28372-28377.
80. Kuznetsov A V, Veksler V, Gellerich F N, Saks V, Margreiter R, Kunz W S. Analysis of mitochondrial function in situ in permeabilized muscle fibers, tissues and cells. *Nat Protoc.* 2008; 3(6):965-976.
81. Boudina S, Sena S, O'Neill B T, Tathireddy P, Young M E, Abel E D. Reduced mitochondrial oxidative capacity and increased mitochondrial uncoupling impair myocardial energetics in obesity. *Circulation.* 2005; 112(17):2686-2695.
82. Karamanlidis G, Nascimben L, Couper G S, Shekar P S, Del Monte F, Tian R. Defective DNA replication impairs mitochondrial biogenesis in human failing hearts. *Circ Res.* 2010; 106(9):1541-1548.
83. Williams C D, Regnier M, Daniel T L. Axial and radial forces of cross-bridges depend on lattice spacing. *PLoS Comput Biol.* 2010; 6(12):e1001018.
84. Campbell S G, Lionetti F V, Campbell K S, McCulloch A D. Coupling of adjacent tropomyosins enhances cross-bridge-mediated cooperative activation in a markov model of the cardiac thin filament. *Biophys J.* 2010; 98(10):2254-2264.
85. Campbell S G, Howard E, Aguado-Sierra J, Coppola B A, Omens J H, Mulligan L J, McCulloch A D, Kerckhoffs R C. Effect of transmurally heterogeneous myocyte excitation-contraction coupling on canine left ventricular electromechanics. *Exp Physiol.* 2009; 94(5):541-552.
86. Campbell S G, McCulloch A D. Multi-scale computational models of familial hypertrophic cardiomyopathy: genotype to phenotype. *J R Soc Interface.* 2011; 8(64):1550-1561.

87. Chuang J S, Zemljic-Harpf A, Ross R S, Frank L R, McCulloch A D, Omens J H. Determination of three-dimensional ventricular strain distributions in gene-targeted mice using tagged MRI. *Magn Reson Med.* 2010; 64(5):1281-1288.
88. Kerckhoffs R C, Campbell S G, Flaim S N, Howard E J, Sierra-Aguado J, Mulligan L J, McCulloch A D. Multi-scale modeling of excitation-contraction coupling in the normal and failing heart. *Conf Proc IEEE Eng Med Biol Soc.* 2009; 2009:4281-4282.
89. Beeri R, Chaput M, Guerrero J L, Kawase Y, Yosefy C, Abedat S, Karakikes I, Morel C, Tisosky A, Sullivan S, Handschumacher M D, Gilon D, Vlahakes G J, Hajjar R J, Levine R A. Gene delivery of sarcoplasmic reticulum calcium ATPase inhibits ventricular remodeling in ischemic mitral regurgitation. *Circ Heart Fail.* 3(5):627-634.
90. Bott-Flugel L, Weig H J, Knodler M, Stadele C, Moretti A, Laugwitz K L, Seyfarth M. Gene transfer of the pancaspase inhibitor P35 reduces myocardial infarct size and improves cardiac function. *J Mol Med* (Berl). 2005; 83(7):526-534.
91. Prasad K M, Smith R S, Xu Y, French B A. A single direct injection into the left ventricular wall of an adeno-associated virus 9 (AAV9) vector expressing extracellular superoxide dismutase from the cardiac troponin-T promoter protects against myocardial infarction. *J Gene Med.* 2011; 13(6):333-341.
92. Laflamme M A, Chen K Y, Naumova A V, Muskheli V, Fugate J A, Dupras S K, Reinecke H, Xu C, Hassanipour M, Police S, O'Sullivan C, Collins L, Chen Y, Minami E, Gill E A, Ueno S, Yuan C, Gold J, Murry C E. Cardiomyocytes derived from human embryonic stem cells in pro-survival factors enhance function of infarcted rat hearts. *Nat Biotechnol.* 2007; 25(9):1015-1024.
93. Laflamme M A, Zbinden S, Epstein S E, E. M C. Cell-based therapy for myocardial ischemia and infarction: pathophysiological mechanisms. *Annu Rev Pathol Mech Dis.* 2007; 2:307-339.
94. Nussbaum J, Minami E, Laflamme M A, Virag J A, Ware C B, Masino A, Muskheli V, Pabon L, Reinecke H, Murry C E. Transplantation of undifferentiated murine embryonic stem cells in the heart: teratoma formation and immune response. *Faseb J.* 2007; 21(7):1345-1357.
95. Neubauer S. The failing heart—an engine out of fuel. *N Engl J Med.* 2007; 256(11):1140-1151.

Gregorevic P, Blankinship M J, Allen J, Crawford R W, Meuse L, Miller D, Russell D W and Chamberlain J S: Systemic delivery of genes to striated muscles using adeno-associated viral vectors. Nature Med 2004; 10:828-834.

Blankinship M J, Gregorevic P, Allen J M, Harper S Q, Harper H, Halbert C, Miller A D and Chamberlain J S. Efficient transduction of skeletal muscle using vectors based on adeno-associated virus serotype 6. Mol Ther 2004; 10:671-678.

Blankinship M, Gregorevic P and Chamberlain J S: Gene therapy strategies for Duchenne muscular dystrophy utilizing recombinant adeno-associated virus vectors. Mol Ther 2006; 13:241-249.

Salva M Z, Himeda C L, Tai P W, Nishiuchi E, Gregorevic P, Allen J M, Finn E E, Nguyen Q G, Blankinship M J, Meuse L, Chamberlain J S and Hauschka S D: Design of tissue-specific regulatory cassettes for high-level rAAV-mediated expression in skeletal and cardiac muscle. Mol Ther 2007; 15:320-329.

What is claimed is:

1. A pharmaceutical composition comprising a first viral vector comprising a first nucleic acid sequence encoding ribonucleotide reductase subunit R1 and a second viral vector comprising a second nucleic acid sequence encoding ribonucleotide reductase subunit R2, said first nucleic acid sequence and second nucleic acid sequence being operably linked to a cardiac-specific promoter, wherein said cardiac-specific promoter comprises the nucleic acid sequence SEQ ID NO: 1.

2. A pharmaceutical composition comprising cardiomyocytes containing a first expression vector comprising a first nucleic acid sequence encoding ribonucleotide reductase subunit R1 and a second expression vector comprising a second nucleic acid sequence encoding ribonucleotide reductase subunit R2, said first nucleic acid sequence and second nucleic acid sequence being operably linked to a promoter that induces overexpression of R1 and R2, wherein said promoter that induces overexpression of R1 and R2 comprises the nucleic acid sequence SEQ ID NO: 1.

3. The pharmaceutical composition of claim 1, wherein said first and second viral vectors are a single viral vector comprising the first nucleic acid sequence, the second nucleic acid sequence, and the cardiac-specific promoter.

4. The pharmaceutical composition of claim 1, wherein said first and second viral vectors are adeno-associated viral vectors.

5. The pharmaceutical composition of claim 1, wherein at least one of said first and second viral vectors is an adeno-associated virus type 6 (AAV6) vector.

6. The pharmaceutical composition of claim 1, further comprising:
a nucleic acid sequence encoding a cTnC variant having a L48Q amino acid substitution, wherein said cTnC variant has an increased binding affinity for $Ca^{2+}$.

7. The pharmaceutical composition of claim 6, further comprising:
a CMV promoter operably linked to the nucleic acid sequence encoding the cTnC variant.

8. The pharmaceutical composition of claim 1, further comprising:
a nucleic acid sequence encoding a cTnC variant having an amino acid substitution selected from I61Q and L57Q, wherein said cTnC variant has a decreased binding affinity for $Ca^{2+}$.

9. The pharmaceutical composition of claim 8, further comprising:
a CMV promoter operably linked to the nucleic acid sequence encoding the cTnC variant.

10. The pharmaceutical composition of claim 1, wherein the pharmaceutical composition is an injectable to be administered to a subject by at least one of systemic administration, intravenous administration, and intramyocardial injection.

11. The pharmaceutical composition of claim 1, wherein at least one of said first and second viral vectors further comprises a transduction reporter.

12. The pharmaceutical composition of claim 2, wherein said first and second expression vectors are part of a single vector comprising the first nucleic acid sequence encoding R1 and the second nucleic acid sequence encoding R2.

13. The pharmaceutical composition of claim 2, wherein said first and second expression vectors are adeno-associated viral vectors.

14. The pharmaceutical composition of claim 2, wherein at least one of said first and second expression vectors is an adeno-associated virus type 6 (AAV6) vector.

15. The pharmaceutical composition of claim 2, wherein at least one of said first and second expression vectors further comprises a transduction reporter.

16. The pharmaceutical composition of claim 2, wherein said cardiomyocytes are derived from at least one of embryonic stem cells, induced pluripotent stem cells, and mesenchymal stem cells.

17. The pharmaceutical composition of claim 16, wherein said cardiomyocytes are of mammalian origin.

18. The pharmaceutical composition of claim 2, wherein said cardiomyocytes are grafted to the myocardium of a subject.

* * * * *